(12) United States Patent
Knapp et al.

(10) Patent No.: US 7,645,581 B2
(45) Date of Patent: Jan. 12, 2010

(54) DETERMINING NUCLEIC ACID FRAGMENTATION STATUS BY COINCIDENT DETECTION OF TWO LABELED PROBES

(75) Inventors: Michael R. Knapp, Palo Alto, CA (US); Jill M. Baker, Redwood City, CA (US); Andrea W. Chow, Los Altos, CA (US); Anne R. Kopf-Sill, Portola Valley, CA (US); Michael A. Spaid, Mountain View, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 0 days.

(21) Appl. No.: 11/867,626

(22) Filed: Oct. 4, 2007

(65) Prior Publication Data
US 2008/0085521 A1 Apr. 10, 2008

Related U.S. Application Data

(60) Division of application No. 10/845,996, filed on May 14, 2004, now abandoned, which is a continuation-in-part of application No. 10/741,162, filed on Dec. 19, 2003, now abandoned.

(60) Provisional application No. 60/462,384, filed on Apr. 11, 2003, provisional application No. 60/436,098, filed on Dec. 20, 2002, provisional application No. 60/518,431, filed on Nov. 6, 2003.

(51) Int. Cl.
*C12Q 1/68* (2006.01)
*C12P 19/34* (2006.01)

(52) U.S. Cl. .......................... 435/6; 435/91.2
(58) Field of Classification Search ............ 435/6, 435/91.2
See application file for complete search history.

(56) References Cited

U.S. PATENT DOCUMENTS

| | | | |
|---|---|---|---|
| 5,271,724 A | 12/1993 | van Lintel | |
| 5,277,556 A | 1/1994 | van Lintel | |
| 5,375,979 A | 12/1994 | Trah | |
| 5,601,982 A * | 2/1997 | Sargent et al. | 435/6 |
| 5,869,004 A | 2/1999 | Parce et al. | |
| 5,925,517 A | 7/1999 | Tyagi et al. | |
| 5,939,291 A | 8/1999 | Loewy et al. | |
| 5,955,029 A | 9/1999 | Wilding et al. | |
| 5,965,410 A | 10/1999 | Chow et al. | |
| 6,037,130 A | 3/2000 | Tyagi et al. | |
| 6,042,709 A | 3/2000 | Parce et al. | |
| 6,149,870 A | 11/2000 | Parce et al. | |
| 6,171,850 B1 | 1/2001 | Nagle et al. | |
| 6,174,670 B1 | 1/2001 | Wittwer et al. | |
| 6,174,675 B1 * | 1/2001 | Chow et al. | 435/6 |
| 6,235,471 B1 | 5/2001 | Knapp et al. | |
| 6,287,520 B1 | 9/2001 | Parce et al. | |
| 6,303,305 B1 | 10/2001 | Wittwer et al. | |
| 6,303,343 B1 | 10/2001 | Kopf-Sill | |
| 6,391,622 B1 | 5/2002 | Knapp et al. | |
| 6,406,893 B1 | 6/2002 | Knapp et al. | |
| 6,440,706 B1 | 8/2002 | Vogelstein et al. | |
| 6,440,722 B1 | 8/2002 | Knapp et al. | |
| 6,444,461 B1 | 9/2002 | Knapp et al. | |
| 6,482,364 B2 | 11/2002 | Parce et al. | |
| 6,503,718 B2 | 1/2003 | Shuber et al. | |
| 6,586,177 B1 | 7/2003 | Shuber et al. | |
| 6,613,580 B1 | 9/2003 | Chow et al. | |
| 7,081,339 B2 | 7/2006 | Slepnev | |
| 2004/0132034 A1* | 7/2004 | Siemering | 435/6 |
| 2005/0069904 A1 | 3/2005 | Peirson et al. | |

FOREIGN PATENT DOCUMENTS

| | | |
|---|---|---|
| WO | WO-94/05414 A1 | 3/1994 |
| WO | WO-97/02357 A1 | 1/1997 |
| WO | WO-98/00231 A1 | 1/1998 |
| WO | WO01/90415 A | 11/2001 |

OTHER PUBLICATIONS

Bousse, et al., "Electrokinetically Controlled Microfluidic Analysis Systems," Annual Review of Biophysics and Biomolecular Structure, Annual Reviews, Inc., Palo Alto, US (2001), vol. 29, pp. 155-181.
Kopp, et al., "Chemical Amplification: Continuous Flow PCR on a Chip," Science, American Association for the Advancement of Science (1998), vol. 280, pp. 1046-1048.
Lagally, et al., "Single-Molecule DNA Amplification and Analysis in an Integrated Microfluidic Device," Anal. Chem., American Chemical Society, Columbus, US (2001), vol. 73, No. 3, pp. 565-570.
Zazzi, et al., "Nested Polymerase Chain Reaction for the Detection of Human Immunodeficiency Virus Type 1 DNA in Clinical Specimens," Jour. Med Virology, Alan R. Liss, New York, US (1992), vol. 38, No. 3, pp. 172-174.
Rungpragayphan S et al, "High-Throughput, Cloning-Independent Protein Library Construction by Combining Single-Molecule DNA Amplication with in Vitro Expression", Journal of Molecular Biology, Nov. 29, 2001, pp. 395-405, vol. 318, No. 2 , London, GB.
Li et al., Anal. Bioanal. Chem. 374, 269-273 (2002).
Wiesner, Nucleic Acids res. 20(21), 5863-5864 (1992).
Wiesner et al., Biochem. Biophys. Res. Comm. 183(2), 553-559 (1992).

* cited by examiner

*Primary Examiner*—Kenneth R. Horlick
(74) *Attorney, Agent, or Firm*—Cardinal Law Group

(57) ABSTRACT

Methods for determining nucleic acid fragmentation status are provided. A nucleic acid of interest in a reaction mixture is contacted with two or more different probes complementary to sites separated by a point of potential fragmentation. The probes each comprise a detectable marker. The nucleic acid of interest is flowed into a detection region, where two or more coincident detectable marker signals from the probes are detected. Fragmentation status of the nucleic acid of interest is determined, coincident detection of signals from two or more of the different probes indicating the nucleic acid of interest is not fragmented between the probes.

25 Claims, 20 Drawing Sheets

DETERMINING NUCLEIC ACID FRAGMENTATION STATUS BY COINCIDENT DETECTION OF TWO LABELED PROBES

CROSS REFERENCE TO RELATED APPLICATIONS

This Application is a divisional of patent application Ser. No. 10/845,996, "SINGLE MOLECULE AMPLIFICATION AND DETECTION OF DNA LENGTH," filed May 14, 2004, now abandoned, which is a continuation-in-part of patent application Ser. No. 10/741,162, "SINGLE MOLECULE AMPLIFICATION AND DETECTION OF DNA IN A MICROFLUIDIC FORMAT," filed Dec. 19, 2003, now abandoned, which is a regular utility application corresponding to Provisional Patent Application U.S. Ser. No. 60/518,431 "SINGLE MOLECULE AMPLIFICATION AND DETECTION OF DNA IN A MICROFLUIDIC FORMAT" filed Nov. 6, 2003, Provisional Patent Application U.S. Ser. No. 60/462,384 "SINGLE MOLECULE AMPLIFICATION AND DETECTION OF DNA IN A MICROFLUIDIC FORMAT," filed Apr. 11, 2003, and Provisional Patent Application U.S. Ser. No. 60/436,098 "SINGLE MOLECULE AMPLIFICATION AND DETECTION OF DNA IN A MICROFLUIDIC FORMAT," filed Dec. 20, 2002. The subject application claims priority to and benefit of each of these prior applications, which are incorporated herein by reference in their entirety.

STATEMENT AS TO RIGHTS TO INVENTIONS MADE UNDER FEDERALLY SPONSORED RESEARCH AND DEVELOPMENT

Part of the technology for this application was developed under NIST-ATP grant 70NANB8H4000. The Government may have certain rights in this invention.

FIELD OF THE INVENTION

The invention is in the field of single molecule detection, e.g., by amplification of single molecules from complex mixtures, e.g., for disease diagnosis, detection of pathogens, environmental contaminants, or the like. Amplifications can be conducted in high throughput systems, e.g., microfluidic systems, to provide an ability to detect rare molecules in complex samples that are aliquoted into low copy number reaction mixtures, whereby a rare copy nucleic acid of interest is detected, e.g., by amplifying large numbers of aliquots of the complex samples. The methods and systems can determine whether an individual nucleic acids of interest has a given length.

BACKGROUND OF THE INVENTION

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer.

One of the most powerful and basic technologies for nucleic acid detection is nucleic acid amplification. That is, in many typical formats, such as the polymerase chain reaction (PCR), reverse-transcriptase PCR (RT-PCR), ligase chain reaction (LCR), and Q-β replicase and other RNA/transcription mediated techniques (e.g., NASBA), amplification of a nucleic acid of interest precedes detection of the nucleic acid of interest, because it is easier to detect many copies of a nucleic acid than it is to detect a single copy.

PCR, RT-PCR and LCR are in particularly broad use, in many different fields. Details regarding the use of these and other amplification methods can be found in any of a variety of standard texts, including, e.g., Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")) and *PCR Protocols A Guide to Methods and Applications* (Innis et al. eds) Academic Press Inc. San Diego, Calif. (1990) (Innis). Many available biology texts have extended discussions regarding PCR and related amplification methods.

More recently, a number of high throughput approaches to performing PCR and other amplification reactions have been developed, e.g., involving amplification reactions in microfluidic devices, as well as methods for detecting and analyzing amplified nucleic acids in or on the devices. Details regarding such technology is found in the technical and patent literature, e.g., Kopp et al. (1998) "Chemical Amplification: Continuous Flow PCR on a Chip" *Science*, 280 (5366):1046; U.S. Pat. No. 6,444,461 to Knapp, et al. (Sep. 3, 2002) MICROFLUIDIC DEVICES AND METHODS FOR SEPARATION; U.S. Pat. No. 6,406,893 to Knapp, et al. (Jun. 18, 2002) MICROFLUIDIC METHODS FOR NON-THERMAL NUCLEIC ACID MANIPULATIONS; U.S. Pat. No. 6,391,622 to Knapp, et al. (May 21, 2002) CLOSED-LOOP BIOCHEMICAL ANALYZERS; U.S. Pat. No. 6,303,343 to Kopf-Sill (Oct. 16, 2001) INEFFICIENT FAST PCR; U.S. Pat. No. 6,171,850 to Nagle, et al. (Jan. 9, 2001) INTEGRATED DEVICES AND SYSTEMS FOR PERFORMING TEMPERATURE CONTROLLED REACTIONS AND ANALYSES; U.S. Pat. No. 5,939,291 to Loewy, et al. (Aug. 17, 1999) MICROFLUIDIC METHOD FOR NUCLEIC ACID AMPLIFICATION; U.S. Pat. No. 5,955,029 to Wilding, et al. (Sep. 21, 1999) MESOSCALE POLYNUCLEOTIDE AMPLIFICATION DEVICE AND METHOD; U.S. Pat. No. 5,965,410 to Chow, et al. (Oct. 12, 1999) ELECTRICAL CURRENT FOR CONTROLLING FLUID PARAMETERS IN MICROCHANNELS, and many others.

Despite the wide-spread use of amplification technologies and the adaptation of these technologies to truly high throughput systems, certain technical difficulties persist in amplifying and detecting nucleic acids, particularly rare copy nucleic acids. This is particularly true where the amplification reagents amplify a high copy nucleic acid in a given sample in addition to the rare nucleic acid and the two nucleic acids differ by only one or a few nucleotides in the same sample. For example, if a set of primers hybridizes to a high copy nucleic acid, as well as to a low copy nucleic acid in a given sample, the geometric amplification of the high copy nucleic acid proportionately dominates the amplification reaction and it is difficult or impossible to identify the low copy nucleic acid in any resulting population of amplified nucleic acids. Thus, low copy number alleles of a gene can be very difficult to detect, e.g., where a primer set cannot easily be identified that only amplifies the rare nucleic acid (and the practitioner will realize that perfect reagent specificity is rare or non-existent in practice). Amplification of the higher copy number nucleic acids in the sample swamps out any signal from the low copy nucleic acid. In spite of such difficulties, identification of rare copy nucleic acids can be critical to identifying disease or infection in the early stages, as well as in many other applications.

It is worth noting that these problems simply have not been addressed by the prior art. While a few authors have described single copy amplification as a theoretical exercise (e.g., Mullis et al (1986) *Cold Spring Harbor Symp. Quant. Biol.* 51:263-273; Li et al. (1988) *Nature* 335:414-417; Saiki et al (1988) *Science* 239:487-491, and Zhang et al (1992) *Proc. Natl. Acad. Sci. USA* 89:5847-5851), and others have described stochastic PCR amplification of single DNA template molecules followed by CE analysis of products in a microscale device (Lagally et al. (2001) *Anal. Chem.* 73:565-570), none of these prior approaches are suitable for detection of rare copy nucleic acids in samples. That is, none of these approaches are suitable to high throughput automation and the devices in the prior art cannot be adapted to practicably detect rare copy nucleic acids. For example, the device of Lagally et al., id., flowed sample to be amplified into chambers, stopped flow of the system, ran the amplification reaction, manually reconfigured the device to flow amplification products out of the chambers, ran the amplification products out of the chambers for one reaction at a time, and detected the product. This cumbersome process results in few amplification reactions being made and analyzed in any useful time period and required almost continuous user intervention to make the system operate. In addition, none of the prior methods unambiguously determine the length of a nucleic acid of interest from a homogenous mixture, e.g., without additional steps of size selective chromatography.

Another difficulty with amplification methods that is completely unaddressed in the prior art is that it can be quite difficult to perform quantitative analysis on rare nucleic acids. The problems noted above for detection apply to quantitative analysis as well, with the additional problem that quantification is impacted by the presence of high copy number nucleic acids in the sample, even if the rare nucleic acid can be amplified. This is because, even if the amplification is sufficiently specific for detection of the rare nucleic acid, the high copy number of other amplified nucleic acids still has competitive effects on the amplification reaction for reaction components during the amplification reaction. Thus, it is not generally possible to assess accurately the concentration of rare nucleic acids in a sample, particularly where the components of the system have not previously been characterized or purified (it is, of course, somewhat simpler to assess amplification products quantitatively if the materials selected for amplification are already characterized). While amplification of materials that have already been fully characterized is of academic interest, this approach is of little practical value if it cannot be adapted to characterization of unknown materials. For example, the inability to quantify rare nucleic acids limits, e.g., the ability to diagnose disease, to establish disease prognosis and to perform accurate statistical assessments of the nucleic acid of interest.

Sizing of nucleic acids of interest is an area where identification of rare sequences can be of particular interest. For example, in disease states, such as certain cancers and conditions caused by deletion mutations, the length of a nucleic acid of interest in a complex mixture of other nucleic acids can be diagnostic. In U.S. Pat. No. 6,586,177 to Shuber (Jul. 1, 2003) METHODS FOR DISEASE DETECTION, clinical samples are amplified in a multiwell format with two or more primer pairs followed by agarose gel electrophoresis of the amplification reactions to visualize the amplicons. Shuber suggests the assay can be useful to determine proportions of degraded DNA from cells after apoptosis relative to full length DNA from cancer cells in certain clinical samples. However, this method can be nonspecific, slow and labor intensive, fail to confirm separated amplicons were amplified from the same nucleic acid strands (i.e., ambiguous), fail to distinguish between long nucleic acids with marginally different lengths, fail to determine length directly from a homogenous mixture, and fail to detect nucleic acids of interest against a background of other nucleic acids in many complex clinical samples.

In view of the above, a need exists for robust high throughput methods of identifying and quantifying rare nucleic acids of interest in a sample. It would be desirable to have methods and systems that efficiently confirm the length, quantity and proportions of nucleic acids of interest with high resolution and accuracy. The present invention provides these and other features that will be apparent upon review of the following.

SUMMARY OF THE INVENTION

The present invention relates to the surprising discovery that single molecule amplification can be used for the detection and statistical characterization of rare nucleic acids of interest in a sample, e.g., for disease diagnosis (e.g., cancer diagnosis), detection of pathogens, detection of rare environmental nucleic acids, and the like. For example, many individual amplification reactions can be performed on reaction mixtures derived from a sample comprising a rare nucleic acid of interest, where each reaction mixture has few (e.g., 1) or no copies of the rare a nucleic acid of interest, e.g., until the nucleic acid of interest is identified in a reaction mixture. Additional nucleic acids in the sample can also be amplified in low copy number reactions and statistical methods can be used to determine the relative ratio of the nucleic acid of interest to the additional nucleic acid, e.g., to determine relative or absolute concentration of the nucleic acid of interest including proportions of full length and fragmented forms. Desirably, most or all of the steps in the methods herein can be performed in a continuous flow format to greatly speed the rate of the overall method. Alternately, one or more of the steps can be performed in a stopped flow mode, e.g., where the detector is configured to simultaneously scan multiple amplification regions at once (simultaneous detection provides for increased throughput in these embodiments).

High throughput amplification systems such as those embodied in high throughput microfluidic systems are particularly well adapted to performing these methods, which can be used to detect nucleic acids of interest that are present at exceedingly low concentrations in a sample to be analyzed, e.g., by performing many low copy number amplification reactions until the nucleic acid of interest is detected, and/or until enough copies of the nucleic acid of interest are detected that reliable statistical evaluations can be performed. In a related aspect, the invention also provides new ways of determining whether and how many copies of an initial nucleic acid are present in a reaction mixture (or whether the initial nucleic acid is present in a reaction mixture) by considering how far signal from the initial nucleic acid disperses during amplification and comparing the dispersion to expected dispersion arising from thermal diffusivity and/or Taylor Aris dispersion, or related phenomena (or even simply by comparison of the observed dispersion to empirically observed control reactions). This can include monitoring the shape (amplitude, signal width, and/or other signal shape features) of a signal generated from an aliquot comprising the nucleic acid of interest to a predicted or empirically observed signal shape. These shape features of the signal are extremely reproducible, which provides an ability to distinguish signals of interest from background random signal fluctuations. Both the number of molecules in an aliquot and the ability to distinguish signals of interest from background signal fluctuations can be performed by this class of methods. Systems and kits adapted to performing the various methods herein are also a feature of the invention. The nucleic acids that are quantified can be known (e.g., controls) or unknown in composition. They can include experimental nucleic acids (the nucleic acids of primary interest in the experiment at issue) or can be other unknown nucleic acids (e.g., uncharacterized genomic and/or cDNA from a biological sample of interest).

Accordingly, in a first aspect, methods of detecting a nucleic acid of interest are provided. In the methods, a sample comprising the nucleic acid of interest and one or more additional nucleic acid is aliquoted into a plurality of reaction mixtures. At least two of the reaction mixtures are single copy reaction mixtures, each comprising a single copy of the nucleic acid of interest. The plurality of reaction mixtures additionally comprise at least one additional reaction mixture comprising at least one copy of the additional nucleic acid. The plurality of reaction mixtures are subjected to one or more amplification reaction (in this context, the amplification reaction may or may not amplify the nucleic acid of interest, i.e., if the reaction has zero copies of the nucleic acid of interest, it will not be amplified; if it has one or more copy it will). The nucleic acid of interest is detected in one or more of the single copy reaction mixtures. Statistical inferences and mathematical relationships can be determined based on the plurality of results from such analyses. For example, the absolute numbers and/or relative proportions of full length and fragmented nucleic acids of interest in a complex sample can be determined.

In a closely related aspect, the invention includes methods of detecting a low copy nucleic acid of interest in a sample that has one or more higher copy additional nucleic acid that is different from the low copy nucleic acid. The method includes aliquotting the sample into a plurality of reaction mixtures. The mixtures can include a plurality (e.g., about 5, or more, about 10 or more, about 50 or more, about 100 or more, about 150 or more, or about 500 or more) of zero copy reaction mixtures that include zero copies of the nucleic acid of interest and at least one single copy reaction mixture comprising a single copy of the nucleic acid of interest. The zero and single copy reaction mixtures are subjected to an amplification reaction (whether an amplification actually occurs or not). The nucleic acid of interest is then detected in the single copy reaction mixture (this includes the possibility that the nucleic acid of interest is detected in one or in multiple individual single copy reactions). The proportion of zero copy and single copy reaction mixtures can be incorporated into mathematical formulas, along with, e.g., sample dilution data, to determine the concentration of the nucleic acid of interest in a sample, and/or the proportions of the nucleic acid in full length or fragmented forms.

In an additional related class of embodiments, related methods of quantifying a nucleic acid of interest in a sample are provided. In the methods, the sample can be aliquoted into at least 25 reaction mixtures comprising 2 or fewer copies of the nucleic acid of interest each (and generally 1 or fewer). The reaction mixtures can be subjected to one or more amplification reactions. The nucleic acid of interest is then detected in a plurality of the reaction mixtures. In a number of embodiments, statistical evaluations of the nucleic acid of interest are performed based upon the detection of the nucleic acid of interest in the plurality of reaction mixtures. In one class of embodiments, at least 50 or more, at least 75 or more, or at least 100 or more reaction mixtures, comprising the 2 or fewer copies, are subjected to the one or more amplification reactions.

In an additional class of related embodiments, methods of detecting a low copy nucleic acid of interest are provided. In the methods, a sample comprising the low copy nucleic acid of interest is aliquoted into a plurality of reaction mixtures. A plurality of the reaction mixtures contain zero copies of the nucleic acid of interest and at least one of the reaction mixtures comprises at least one copy of the nucleic acid of interest. A plurality of the plurality of zero copy reaction mixtures is subjected to one or more amplification reaction in a microfluidic device comprising at least one microchamber or microchannel. The nucleic acid of interest is determined not to be present in the zero copy reaction mixtures. At least one additional zero copy reaction mixture and the reaction mixture comprising the nucleic acid of interest are subjected to one or more amplification reaction. The nucleic acid of interest is detected in the reaction mixture comprising the nucleic acid of interest. Put another way, the reaction mixtures are amplified and checked for the presence of the nucleic acid of interest in the microfluidic device, at least until the nucleic acid is detected. For a low copy number nucleic acid, this can require a large number of amplification reactions be performed on the zero copy reaction mixtures until the nucleic acid of interest is found.

The invention also provides methods for quantifying a nucleic acid of interest in a sample, e.g., by taking diffusion/dispersion into consideration. In the methods, a sample comprising a copy of the nucleic acid of interest, or a complement thereof, is aliquoted into at least one reaction mixture. The reaction mixture is subjected to at least one amplification reaction, thereby amplifying the copy of the nucleic acid of interest. A shape, volume, width, length, height, area, or the like, in which the nucleic acid of interest, or a signal corresponding thereto, is present is detected. The shape, volume, width, height, length, or area is interpreted to indicate a number of copies of the nucleic acid of interest in the reaction mixture or sample, thereby quantifying the nucleic acid of interest in the sample. Because these shape features of the signal are extremely reproducible, it is straightforward to distinguish signals of interest from background random signal fluctuations. In a related aspect, knowledge of diffusion/dispersion and the reproducibility of these phenomena can be used to reliably distinguish the signal of a one or more target molecule(s) from random baseline system fluctuations. In any case, this interpretation can be performed in any of a variety of ways, e.g., by comparing the shape, volume, width, height, length and/or other signal shape features to predicted values taking thermal diffusivity and/or Taylor-Aris dispersion into account and/or by back calculation from empirically observed values for known reactions performed in the system. It is worth noting that this method is particularly relevant to continuous flow systems, where materials disperse during flow. In quantitation or proportioning of fragmented and unfragmented forms of a nucleic acid of interest, signals can be read in parallel from homogenous mixtures, e.g., by using probes emitting signals at different wavelengths. Quantitation of the two or more forms (lengths) of the nucleic acid can separately be based on interpretation of the same or different signal parameters.

In yet another class of embodiments, high throughput stopped flow methods of detecting rare nucleic acids are provided. For example, methods of detecting a nucleic acid of interest are provided, in which a sample comprising the nucleic acid of interest is aliquoted into a plurality of reaction mixtures. At least two of the reaction mixtures are single copy reaction mixtures, each comprising a single copy of the nucleic acid of interest. The reaction mixtures are flowed throughout a network of microchannels and subjected to one or more amplification reaction under stopped flow conditions in the network of microchannels. The nucleic acid of interest is detected in the single copy reaction mixtures under the stopped flow conditions. Desirably, the detection step can include detection of multiple reaction products simultaneously. For example, a CCD array or appropriate image processor can be used to scan an entire chip (or sub-regions thereof) for "clouds" of signal from amplified products. That is, an entire channel or network of channels can be scanned simultaneously (e.g., at two or more frequencies to detect two or more probes) after amplification and any or all regions where signal arising from amplification can be detected simultaneously (or in more than one pass of the scanner/detector, if desired). Where size detection employs two or more probes with different signals, system software can compare signal locations for coincident (typically indicating a nucleic acid of interest has a given length) and non-coincident signals (typically indicating a nucleic acid of interest is fragmented).

It will be appreciated that the above methods overlap with one another and that many of the above methods can be performed in combination with one another. Similarly, any or all of the above methods can be practiced in a continuous flow format to improve throughput of the relevant method, and/or can use stopped flow in combination with image analysis of multiple regions of (or an entire) microchannel network.

For any or all of the methods herein, the reaction mixture can comprise the nucleic acid of interest and one or a plurality of additional nucleic acids (typically sample native nucleic acids not of interest or control nucleic acids), with the relevant method including detecting the nucleic acid of interest and/or the plurality of additional nucleic acids in the reaction mixture. The methods optionally include adding up the number of nucleic acids of interest, or the plurality of additional nucleic acids, or both, in the reaction mixture or the sample, or both. A ratio of the nucleic acid of interest or the plurality of additional nucleic acids in the reaction mixture to the sum of the nucleic acid of interest and/or the plurality of additional nucleic acids in the reaction mixture or sample can be determined. From this, a concentration or proportion of the nucleic acid of interest in the reaction mixture or sample can be determined. Similarly, the sum of the number of nucleic acids of interest and the plurality of additional nucleic acids can provide an indication of the total number of nucleic acids in the reaction mixture.

For any or all of the methods herein, aliquotting the sample or reaction mixture can comprise diluting the sample into a plurality of reaction containers (e.g., wells in a microtiter plate), and/or flowing the sample into a microfluidic dilution channel or chamber. In microfluidic embodiments, the sample is optionally diluted in the microfluidic dilution channel or chamber (a form of dilution module in the systems of the invention), whereby the sample is aliquoted into multiple diluted aliquots in the microfluidic dilution channel or chamber. Optionally, the part or all of the aliquotting/dilution process can be multiplexed for high throughput, e.g., by flowing a plurality of samples into the device or reaction containers simultaneously. Samples, aliquots, reaction mixtures, etc., can be flowed under pressure (e.g., into the microfluidic device) or via electroosmosis, or by any other available method. For convenience in microfluidic embodiments, the sample can be diluted from a common reaction component reservoir, e.g., comprising some or all of the reaction and/or buffer components for the amplification reactions (e.g., polymerase, primers, locus specific reagents, labels, salts, magnesium, water and/or the like). Alternately, one or more component can be located in one or more additional reservoirs and the components can be mixed prior to amplification. Desirably, any or all of these steps can be practiced in a continuous flow format, or utilizing the stopped flow/simultaneous image analysis methods noted herein.

The concentration of the nucleic acids of interest and/or any additional nucleic acid is optionally low in the methods of the invention, e.g., about 1 molecule per aliquot. For example, the sample can be diluted to a concentration of about 1 molecule of interest per nanoliter or less. Optionally, diluted aliquots are each diluted to the same degree; however, diluted aliquots can also be differentially diluted (e.g., to form a dilution series). The volume of the aliquots can be quite low to keep reagent costs low, e.g., in microfluidic applications. For example, the aliquots can be less than about 100 nl in volume, e.g., less than about 10 nl in volume, or, e.g., about 1 nl in volume or less.

In a number of embodiments, at least one of the reaction mixtures is in an aqueous solution (the enzymes used in typical amplification reactions typically function well in an aqueous environment) dispersed as an emulsion. This can take the form of individually resolved reaction mixture droplets in a microfluidic device, fluid in reservoirs of a microtiter plate, or other forms such as where at least one of the reaction mixtures is formulated in an aqueous phase of an emulsion comprising aqueous droplets suspended in an immiscible liquid (in this embodiment, amplification can be performed on the reaction mixture when it is formulated in the emulsion). In the emulsion embodiment, the nucleic acid of interest is optionally present as a single copy in at least one aqueous droplet of the aqueous phase prior to performing the amplification reaction. The nucleic acid of interest is detected in the emulsion after the amplification reaction is performed. Optionally, a plurality of additional nucleic acids are also formulated in the aqueous phase of the emulsion and the method comprises detecting the plurality of additional nucleic acids. As with other embodiments herein, statistical analysis can be performed on, e.g., the ratio of the nucleic acid sizes nucleic acids in the emulsion, e.g., to determine the concentration and/or proportions of the nucleic acids of interest having a given length in the emulsion.

In any of the methods herein, at least 10 of the reaction mixtures are optionally low copy reaction mixtures (e.g., comprising 100 or fewer, usually 50 or fewer, typically 10 or fewer, generally 2 or fewer and often 1 or fewer copies of the nucleic acid of interest and/or of the additional nucleic acid). Optionally, at least 25, at least 50, at least 100, at least 150, at least 500 or more of the reaction mixtures are low copy reaction mixtures. The low copy reaction mixtures can comprise at least 10, at least 25, at least 50, at least 100, at least 150 at least 500 or more single or zero copy reaction mixtures comprising 1 or fewer copies of the nucleic acid of interest. The reaction mixtures can, and often do, comprise no copies of the nucleic acid of interest. Thus, a plurality of the reaction mixtures can comprise a plurality of zero copy reaction mixtures that comprise no copies of the nucleic acid of interest. That is, at least about 10, 25, 50, 100, 150, 500, 1,000 or even 10,000 or more of the reaction mixtures can be zero copy reaction mixtures that have no copies of the nucleic acid of interest. In one aspect, the invention provides the ability to rapidly search through many such zero copy reaction mixtures to individually identify a full length or fragmented nucleic acid of interest.

In several embodiments of the invention, the sample comprises at least one additional nucleic acid that is different than the nucleic acid of interest. The additional nucleic acid can, and often does, exist at a higher copy number in the sample than the nucleic acid of interest. The additional nucleic acid can be a known nucleic acid (e.g., a control or hybridization blocking nucleic acid) or can itself be unknown with respect to part or all of the composition (a common occurrence where the nucleic acid of interest is to be detected in a biological sample, e.g., a cell or tissue sample from a patient). For example, the additional nucleic acid can be present at a concentration at least about 100×, at least about 1,000×, at least about 10,000×, at least about 100,000×, at least about 1,000,000× or greater as high as the nucleic acid of interest in the sample (that is, can have at least about 100×, at least about 1,000×, at least about 10,000×, at least about 100,000×, at least about 1,000,000× or greater as many copies as the nucleic acid of interest in the sample). By screening sufficient numbers of sample aliquots, the nucleic acid of interest can be detected regardless of its relative concentration.

Optionally, the additional nucleic acid can be detected independent of the nucleic acid of interest. A ratio of the nucleic acid of interest to the additional nucleic acid can be determined, e.g., for statistical analysis of the nucleic acid of interest and/or the additional nucleic acid. The number of nucleic acids in the reaction mixture (whether the nucleic acid(s) of interest, the additional nucleic acids, or other nucleic acids) can be added up and the concentration of the nucleic acids (or the relative concentrations) can be determined in the sample, or in any of the various aliquots and reaction mixtures herein. In some embodiments the ratio(s) and/or quantities of fragmented nucleic acid of interest, nucleic acid of a given length, and/or an additional nucleic acid can be determined using methods of the invention.

The nucleic acid of interest can be essentially any detectable nucleic acid. Examples include SNPs, low copy nucleic acids, cancer associated nucleic acids, infective or pathogen associated nucleic acids, forensic nucleic acids, and the like. Because of the ability of the methods of the invention to identify extremely low copy number nucleic acids, and/or distinguish nucleic acids by size, the invention is suitably applied to early stage disease diagnosis where cancer cells or pathogens are present at low concentrations. For example, colon cancer cells can be present in stool samples, but, at least in the early stages of colon cancer, the concentration of cancer cell DNA is small compared to the overall DNA in such a sample (typically much less than 1% of the cells from which the DNA sample was derived). Typically, nucleic acids from the cancer cells is relatively more full length than nucleic acids from other (apoptotic) cells in the sample. The present invention can be used to identify, proportion, and quantify cancer DNA in such a sample, providing a new method for disease diagnosis and prognostication. Similar approaches can be used to identify cancerous DNAs or pathogen nucleic acids from any fluid or tissue from which such samples are normally taken or derived, e.g., blood, urine, serum, plasma, saliva, tears, sputum, stool, ejaculatory fluid, cervical swabs, vaginal secretions, or the like. From these samples, infective/pathogenic agents such as viruses (e.g., HIV, herpes virus, pox virus, etc.), parasites (e.g., malarial parasites (Plasmodium), nematodes, etc.), bacteria (e.g., pathogenic E. coli, salmonella, etc.) can be identified. Where the pathogen is present at a relatively low concentration relative to related non-pathogenic organisms (e.g., pathogenic E. coli are present at an initially low concentration in the gut, as compared to non-pathogenic E. coli), the methods are particularly suitable. Methods can distinguish nucleic acids from living bacteria from those of lysed bacteria, e.g., in a clinical sample.

Most typically, the methods of the invention utilize thermocyclic amplification reactions, although non-thermocyclic reactions (e.g., using denaturants in place of heat, a procedure that is relatively practical in microscale applications) can also be used. In one typical class of embodiments, the reaction mixtures are subjected to one or more amplification reaction(s) by thermocycling the reaction mixtures in one or more microscale amplification chamber or channel. A variety of thermocycling methods can be used in a microscale device (or in reaction containers), e.g., heating by applying electrical current to fluid of the reaction mixture (e.g., in the microscale amplification chambers or channels), resistively heating a heating element that contacts or is in proximity to the reaction mixture (e.g., in the microscale amplification chambers or channels), heating with a Joule-Thompson or Peltier device, or any other available heating or heating and cooling method(s).

Optionally, the components of the system can be treated with one or more reagents between operational runs to reduce cross contamination between operations. For example, the amplification channel can have acid or base flowed into the channel between amplification reactions to reduce unwanted contamination from one or more previous amplification products.

In a convenient class of embodiments, detecting can include real time homogenous PCR detection, e.g., via use of TaqMan™ probes (operating by detecting a double-labeled probe before, during, or after polymerase-mediated digestion of the double labeled probe), use of molecular beacons, or the like. Real time detection can be omitted, e.g., simply by detecting amplicons via labeled probes, e.g., after separation of the amplicon from unlabeled probe.

Optionally, the detecting step(s) can include quantifying the nucleic acids of interest in the reaction mixtures, or the sample, or both. Alternately, the nucleic acids can be quantified separate from the detection step. In either case, quantifying the nucleic acid of interest optionally comprises detecting the nucleic acid in a plurality of single-copy reaction mixtures and performing statistical or probabilistic analysis to determine a percentage or distribution of reaction mixtures comprising a single copy of the nucleic acid of interest. The statistical or probabilistic analysis can comprise any available technique or combination thereof, e.g., Poisson analysis, Monte Carlo analysis, application of a genetic algorithm, neural network training, Markov modeling, hidden Markov modeling, multidimensional scaling, partial least squares (PLS) analysis, or principle component analysis (PCA).

In many of the methods, the initial starting concentration of a nucleic acid of interest (e.g., full and/or fragmented forms) can be determined, e.g., by detecting a reproducible shape, length, width, height, volume or area of associated signal(s) for the nucleic acid of interest in a given reaction mixture. For example, the signal can be detected from a label bound to the nucleic acid of interest. The shape, length, width, height, volume or area is optionally correlated to a number of nucleic acids interest present in one of the reaction mixtures, and/or present in the sample based upon a Taylor-Aris dispersion calculation, or a thermal diffusivity calculation, or both, or by comparison to an empirically observed set of reaction mixtures having a known number of starting nucleic acids for amplification. Thus, in one aspect, the invention comprises calculating diffusion, or dispersion, or both, of one or more amplified nucleic acids in the given reaction mixture, and correlating the diffusion, or the dispersion, or both, to a number of copies of the nucleic acid of interest in one of the given reaction mixtures prior to amplification.

Systems and/or kits adapted for practicing the methods herein are a feature of the invention. The systems and/or kits can include system instructions (e.g., embodied in a computer or in a computer readable medium, e.g., as system software) for practicing any of the method steps herein. Fluid handling elements for storing, transferring, aliquotting, or diluting samples, e.g., microfluidic handling elements, and detector elements can also be components of the systems and kits herein. In addition, packaging materials, integration elements (e.g., instrument cases, power supplies, etc.), instructions for using the systems and kits and the like can be features of the invention.

In one embodiment, the invention provides a system for detecting low copy nucleic acids of interest in a sample. The system includes a dilution module that dilutes the sample into multiple aliquots and a microfluidic device comprising an amplification channel or chamber configured to thermocycle one or more of the multiple aliquots. A detector integral with or proximal to the microfluidic device is also included, where the detector is configured to detect one or more amplified copies of the nucleic acid of interest in or on the microfluidic device. System instructions that direct the dilution module to aliquot the sample into a plurality of aliquots, including a plurality of zero copy aliquots comprising no copies of the nucleic acids of interest and one or more single copy aliquot comprising a single copy of the nucleic acid of interest are also included. Typically, the system also includes system software that correlates a reproducible signal shape, length, width, volume or area occupied by amplified copies of the nucleic acid of interest, as detected by the detector, to the number of copies of the nucleic acid of interest present in one of the aliquots, or to the number of copies of the nucleic acid of interest present in the sample, or both. The system can typically evaluate the absolute or relative number of nucleic acids of interest having different lengths to provide concentrations and/or proportions of the nucleic acids. Any or all of the system components can be selected to operate such that a sample of interest is continuously flowed during operation of the system. Alternately, the stopped flow/simultaneous image analysis methods noted herein can be applied.

In a related embodiment, systems for quantifying one or more low copy nucleic acid of interest in a sample are provided. In the systems, a dilution module dilutes the sample into multiple aliquots. A microfluidic device comprising an amplification channel or chamber is configured to thermocycle one or more of the multiple aliquots. A detector integral with or proximal to the microfluidic device is configured to detect a reproducible shape, length, width, volume or area occupied by signals from amplified copies of the nucleic acid of interest (often hybridized to a detectable probe or represented by released but previously hybridized probe) present in one of the aliquots following thermocycling of the reaction mixture aliquots. The system can also include system software that correlates the shape, length, width, volume or area occupied by amplified copies of the nucleic acid of interest to the number of copies of the nucleic acid of interest present in one of the aliquots, or to the number of copies of the nucleic acid of interest present in the sample, proportion of nucleic acids with different lengths, etc. Optionally, the system includes system instructions that direct the dilution module to aliquot the sample into a plurality of aliquots, including a plurality of zero copy aliquots comprising no copies of the nucleic acids of interest and one or more single copy aliquot comprising a single copy of the nucleic acid of interest.

For many of the above system embodiments, the dilution module can optionally be integral with the microfluidic device, e.g., as a dilution channel. The microfluidic device can also include one or more electrodes positioned to flow electrical current into the microchamber or channel. Flow of current into the microchamber or channel can be used to heat fluid in the microchamber or channel. The microfluidic device optionally includes or is coupled to one or more heating element (e.g., a resistive heating element, a Peltier device or a Joule Thompson device) positioned within or proximal to the microchamber or channel, which heats fluid in the microchamber or channel.

The detector is typically configured to detect one or more electromagnetic energy signal in or on the microfluidic device, although other in device sensors (e.g., pH, conductivity, etc.) can also be used. For example, the detector can detect fluorescence, luminescence, and/or fluorescence polarization of the sample. Optionally, in some embodiments, the detector can be an off-device instrument, such as, e.g., size selective chromatography instrumentation or a mass spectrometer.

The system optionally comprises software with instructions for performing any of the method steps herein. For example, the system can include statistical or probabilistic system software that performs one or more statistical or probabilistic analysis of signals received from one or more of the aliquots subjected to thermocycling. For example, the statistical or probabilistic analysis can include Poisson analysis, Monte Carlo analysis, application of a genetic algorithm, neural network training, Markov modeling, hidden Markov modeling, multidimensional scaling, PLS analysis, and/or PCA analysis. The statistical or probabilistic analysis optionally comprises quantitatively determining a concentration, proportion, or number of the nucleic acids of interest in the sample.

The systems above also optionally include fluid handling or storage features such as sample storage modules that store the samples until they are to be diluted by the dilution module, a sample retrieval module that retrieves the sample from the sample storage module and delivers it to the dilution module, or the like. These features are optionally designed to provide for continuous flow of fluid (e.g., comprising the sample) through the system (thereby providing for higher sample throughput). Alternately, or in combination, stopped flow/simultaneous image analysis can be used in the systems herein.

Important aspects of the present invention are methods and systems to determine whether a nucleic acid of interest is at least a given length based on the presence, or absence of signals from low or single copy reactions mixtures. The reaction mixtures for such determinations typically contain two or more probes complementary to sequences at positions spaced along one or more strands of the nucleic acid of interest. Coincident detection of two or more probes in the reaction mixture can indicate that individual nucleic acid molecules are not fragmented between probe hybridization sites. Systems useful in determining length by the two probe single copy reaction mixture techniques can include dilution modules and microfluidic devices to prepare and detect the reaction mixtures, and computers to interpret and correlate signal data acquired from detectors.

Methods of determining whether a nucleic acid of interest in a sample comprises at least a given length can include contacting the nucleic acid of interest in a reaction mixture with two or more different probes having detectable markers, and flowing the nucleic acid into a detection region to detect one or more signals from the probes. Coincident detection of two or more signals from different probes can indicate the nucleic acid of interest is not fragmented between the probes. Detection of a single signal can indicate the nucleic acid is fragmented. Such determinations can be considered assays of integrity for a nucleic acid of interest in a sample. Samples for nucleic acid length determinations and differentiations include, e.g., whole blood, serum, plasma, stool, urine, vaginal secretions, ejaculatory fluid, synovial fluid, a biopsy, cerebrospinal fluid, amniotic fluid, sputum, saliva, lymph, tears, sweat, and urine.

In a preferred embodiment of differentiating lengths of nucleic acids of interest in a sample, an amplification reaction can be used to enhance the sensitivity of the assay. The nucleic acid of interest is contacted with a first primer pair and a second primer pair having at least one primer that is outside of the sequence defined by the first primer pair, the nucleic acid of interest is amplified in a reaction mixture in a microchannel or microchamber with polymerase extensions from the primers to produce first amplicons defined by the first primer pair or second amplicons defined by the second primer pair. First and second probes complementary to the first and second amplicon and having detectable markers are introduced into the reaction mixture to hybridize with available complementary sequences, and one or more signals are detected from the probes. Detection of a signal from only one of the probes indicates a fragmented nucleic acid of interest and detecting signals from both probes indicates a nucleic acid that is not fragmented. In preferred embodiments of this sensitive assay, the reaction mixture detected contains only a single copy of the nucleic acid of interest. Reaction mixtures detected in the methods can be homogenous mixtures, e.g., not requiring separation of labeled constituents before detection of signals.

In many embodiments, the concentration of the nucleic acid in samples is adjusted so that desired numbers of low, single, and zero copy reactions can be independently detected. The adjustment can be a concentration, e.g., by immunoprecipitation, capture to a solid support, or ultrafiltration. The adjustment can be a dilution, e.g., by serial dilution or fluidic mixing. In one embodiment, the nucleic acid of interest is diluted or concentrated to provide a concentration of about 1 molecule per nanoliter or less in a reaction mixture.

In many embodiments, detection results from multiple low copy, single copy, and zero copy reactions are compiled to obtain confirmatory data and to allow statistical inferences with a suitable level of confidence. For example, it is an aspect of the invention that for quantitative results it is preferred to aliquot a sample into at least 25 reaction mixtures comprising 2 or fewer copies of the nucleic acid of interest each for hybridization with probes and counting the number of aliquots resulting in detection of a signal from one probe and/or signals from two or more probes. It is preferred that the aliquotting (concentration, dilution, and/or segregation into a small volume) result in one or more reaction mixtures having single copies or zero copies of the nucleic acid of interest; particularly for quantitation or proportion analyses. From the compiled data, the number of one marker signals and two marker signals can be evaluated to determine a proportion of nucleic acids of interest having different lengths. Thresholds can be established for confident correlation of some such proportions with certain disease states.

In many embodiments, it is desirable to amplify relatively short sections of the nucleic acid of interest, e.g., so that random breakage is less likely to fragment the nucleic acid between the primers or so the amplicons can act as consistent control materials. In one aspect, one primer pair in an amplification acts as a control for amplification and/or hybridization efficiency. It is preferred that these primer pairs define amplicons of about 100 base pairs in length. Primer pairs for probe target amplicons are preferably about the same length for each probe and can range from more than about 1000 base pairs to about 20 base pairs, or from about 200 base pairs to about 50 base pairs, or about 100 base pairs. In certain embodiments, described herein, e.g., where the amplicons include shorter amplicons and larger amplicons that overlap the shorter amplicons, the larger amplicons generally range in length from about 5000 base pairs to about 200 base pairs, or about 1000 base pairs. In most examples of amplified determinations, at least one of the probes is complementary to the amplicon sequence defined by one primer pair but not complementary to the amplicon sequence defined by another primer pair.

Amplifications in the methods of determining length are generally provided by constituting amplification reactions containing a polymerizing enzyme to increase the amount of target (e.g., nucleic acid of interest) sequence, increase the amount of hybridized probe, or increase the signal from such probes. Amplifying a nucleic acid in the methods typically involves incorporation of a polymerase into the amplifying reaction, such as a heat stable DNA polymerase for a polymerase chain reaction (PCR), a reverse-transcriptase for RT-PCR, ligase for a ligase chain reaction (LCR), a Q-β replicase, or enzymes for RNA/transcription mediated techniques.

Probes used in the length determinations can have different specificity for sequences along the length of the nucleic acid of interest. The detectable markers on probes with different specificity can have the same signal or, preferably, probes hybridizing to different complements on the nucleic acid or associated amplicons have detectably different signals. The probes can have any suitable detectable markers, but preferred markers are based on fluorescent dyes. In particular, probes are favored that include a fluorescent resonant energy transfer (FRET) detectable marker or a molecular beacon (MB) marker.

Methods of determining given lengths for nucleic acids of interest can quantify the nucleic acid and its fragmentation state. Such quantitation can simply involve counting the number of signals from probes in low or single copy reactions and calculating an amount of the nucleic acid based on known dilution factors, efficiency factors, standard curves, and the like. The quantifying can separately determine the amount of various fragmentation forms of the nucleic acid of interest based on the number of signals from two or more different probes, e.g., having different detectable marker signals. Signal parameters, such as shape, volume, width, height, length, area, or ratio, of the one or more signal (e.g., chart peaks) can be interpreted to confirm an actual signal (i.e., that the signal is not an artifact) and/or to indicate a certain quantity of a nucleic acid in a sample. Quantification can be based on comparison of signal peak parameters to an internal standard signal. Optionally, quantitation can be based on comparison of signals from two or more reaction mixtures comprising different degrees of amplification to standard reaction mixtures with similar degrees of amplification. In this embodiment, different degrees of amplification can be obtained by flowing reaction mixtures through a thermocycler at different flow rates, flowing reaction mixtures different distances into a thermocycler, retaining reaction mixtures in a thermocycler for different amounts of time, or exposing reaction mixtures to different numbers of amplification cycles.

Samples containing unknown amounts of a nucleic acid of interest can be quantified by comparing to their signal peaks to sets of standard signal peaks. For example, a nucleic acid of interest in a sample can be quantified by amplifying a dilution series of standard materials containing known amounts of the nucleic acid of interest through a certain number of amplification cycles, detecting signals associated with standard amplicons produced from the standard materials, amplifying the sample nucleic acid of interest the number of amplification cycles, detecting a signal associated with sample amplicons produced from the sample nucleic acid of interest, and comparing one or more standard amplicon signals to the sample amplicon signal to determine a concentration value for the nucleic acid of interest in the sample. Sample and standard signal parameters for comparison can include, e.g., the shape of their signal peaks, points of inflection on the signal peaks, slopes of the signal peaks, signal peak amplitudes, signal peak areas, signal peak widths at half height, and/or the like. The reliability of results can be enhanced through various schemes of repeated testing. For example, the amplifying, detecting, and comparing steps can be repeated one or more times, with different numbers of amplification cycles, to determine additional concentration values for the sample nucleic acid of interest for statistical evaluation providing more precise or more accurate concentration value results for the nucleic acid of interest in the sample.

Improved assay results can be obtained by gathering signal data after amplifications through two or more different numbers of cycles. A major benefit of running the quantitative assay at different amplifications is to broaden the usable range of the assay. Typically, statistical evaluation of the additional data provided by analysis at multiple amplification levels can enhance other assay parameters, such as precision, accuracy, and sensitivity. Quantifying a nucleic acid of interest in a sample based on detection of multiple amplifications can include: amplifying the nucleic acid of interest through more than one number of amplification cycles, detecting signals associated with amplicons produced from two or more of the amplification cycle numbers, preparing a sample curve of a signal parameter versus number of amplification cycles, and comparing one or more identifiable points from the sample curve to a standard curve of the identifiable points versus concentration to quantify the nucleic acid of interest. Exemplary identifiable points from signal curves include points of inflection, points having a certain slope, points having a certain signal amplitude, points having a certain fraction of a maximum signal amplitude, and/or the like.

Such quantitative assays, relying on identifiable points from signal versus cycle curves, can be used to quantitate or proportion fragmented and unfragmented nucleic acid of interest in evaluations of integrity. Proportions of fragmented and given length nucleic acid of interest can be determined in a sample by: amplifying the nucleic acid of interest through a plurality of amplification cycles in a reaction mixture defining two or more different amplicons of the nucleic acid of interest; detecting, from homogenous reaction mixtures, different signals associated with each of the different amplicons after at least two different numbers of amplification cycles; preparing sample curves for each of the different signals versus numbers of amplification cycles; and, comparing one or more identifiable points from the sample curves to one or more standard curves describing nucleic acid of interest concentrations versus identifiable points. Each of the amplicons can be relatively or absolutely quantitated to determine the amount of nucleic acid of interest sequences in the sample. In preferred embodiments, the amplification reaction mixtures detected are low copy or single copy reaction mixtures, thus allowing unambiguous determinations of fragmented and given length nucleic acid. That is, coincident detection of two or more or the different signals from low or single copy mixtures can indicate a nucleic acid of a given length, or the detection of a one of the different signals can indicate a fragmented nucleic acid. As discussed elsewhere herein, the number of amplification cycles experienced by samples and standards can be controlled, e.g., by flowing the amplification reactions through a thermocycler at different flow rates, flowing the amplification reactions different distances into a thermocycler, retaining the amplification reactions in a thermocycler for different amounts of time, or exposing the amplification reactions to different numbers of amplification cycles.

Systems for differentiating the lengths of nucleic acids of interest in a sample can be used to practice many of the methods described herein. The systems can basically include a microfluidic device with an amplification microchannel or microchamber containing one or more reaction mixtures under conditions that provide one or more amplicons of the nucleic acid of interest, a detector integral with or proximal to the microfluidic device and configured to detect the amplicons as one or more signals from a homogenous mixture, and a software system that interprets one or more coincidentally detected signals to lengths of one or more individual nucleic acid molecules of interest to differentiate lengths of the nucleic acids of interest. High throughput aspects of the system can be advanced by provision of multiple amplification channels in the microfluidic device. The system can include affinity molecules, such as oligonucleotides, on a solid support to capture nucleotides of interest before or during preparation of the reaction mixture, or to capture amplicons for detection. Other system elements, e.g., to enhance high throughput aspects of the invention include sample storage modules, sample retrieval modules, and computers.

The systems of the invention can incorporate a dilution module to adjust the concentration of reaction mixture constituents. The dilution module can be configured to dilute the sample to a concentration providing one or more single copy reaction mixtures for nucleic acids of interest in the amplification microchannel or microchamber. Such a dilution module can be equipment to prepare serial multiwell plate dilutions, or a dilution channel in the microfluidic device. The system can include instructions that direct the dilution module to aliquot the sample or reaction mixture into a plurality of aliquots, including a plurality of zero copy aliquots comprising no copies of the nucleic acid of interest and one or more single copy aliquots comprising a single copy of the nucleic acid of interest. Such dilutions (or concentrations) can provide substantial numbers of non-overlapping reaction mixture aliquots for discrete counting of signals.

Reaction mixtures of the systems can include constituents associated with amplification of the nucleic acid, hybridization reactions of primers or probes, and/or detection of detectable marker signals. A typical reaction mixture for detection of length can include the nucleic acid of interest, a first primer pair, a second primer pair with at least one primer complementary to a sequence of the nucleic acid of interest outside a sequence defined by the first primer pair, and a polymerase that can synthesize amplicons defined by the primer pairs. In some embodiments, a control primer pair defines amplicons of 100 base pairs or less in length while a test primer pair defines longer amplicons ranging in length from about 100 base pairs to about 3000 base pairs. In this embodiment, the control amplicons usually overlap sequences of the longer amplicons with probe signals for longer and control probes indicating the proportion of the nucleic acid that is fragmented. In other embodiments, the two sets of primer pairs define amplicons of about the same length but the amplicons do not overlap. In this embodiment, coincident signals from a low or single copy reaction can indicate the nucleic acid of interest is of a given length (the length defined by the probes and the distance between them).

Amplification reaction mixtures and/or hybridization mixtures can include one or more probes to determine the length of a nucleic acid of interest. The probes can have one or more detectable markers and a sequence complementary to one or more of the amplicons so that the detectable markers provide a signal detectable by the detector. The probes can be complementary to an amplicon sequence defined by one primer pair but not complementary to an amplicon sequence defined by another primer pair, while, in some methods described above, the probes can be complementary to a sequence common to both a first amplicon and a second amplicon. The presence of two different probes with the same marker in a single copy reaction can be inferred, e.g., from the amplitude of a signal received, However, in many embodiments, two or more different probes each comprise different signals for easy independent monitoring of coincident signals. For example detectable markers on different probes can have different fluorescent emission wavelengths. The probes can be, e.g., fluorescent resonant energy transfer (FRET) detectable marker or a molecular beacon (MB) marker. In a particularly preferred embodiment, the probe has a detectable marker includes a quencher removable from the FRET probe by nuclease activity, so that one or more positive signals can be detected from a homogenous mixture against low levels of background noise.

Systems to determine length can include amplification channels or chambers that provide conditions for amplification of a reaction constituent. In preferred systems, the chambers are thermocyclers and the nucleic acid of interest is amplified by a polymerase reaction. The amplification microchannel or microchamber can include, e.g., electrodes to apply a heating current to the microchannel, a resistive heating element, a Joule-Thompson device, a Peltier device, and/or the like. The amplification microchannel or microchamber can be configured to thermocycle the reaction mixture producing amplicons of the nucleic acid of interest in a volume sufficiently small to substantially separate amplification products of a single nucleic acid of interest molecule from other nucleic acid of interest molecules in the sample or from additional nucleic acids in the sample. In the systems of the invention the amplicons can be detected without resolution of different amplicons or different probes, e.g., in a size selective media or affinity media.

Software systems can work in computers to enhance the high throughput aspects of the methods of determining length and automate interpretation of detected signals. For example, the system software can interpret signal volumes, widths, heights, lengths, areas, and/or ratios, from the detector to indicate a number of copies of the nucleic acid of interest in the sample, a number of the nucleic acids of interest having a given length, or a proportion of nucleic acids of interest having different lengths.

Detectors in the systems can detect signals from any suitable detectable marker. Detectors can include technologies, such as, e.g., fluorometers, charge coupled device, lasers, enzymes or chromogenic enzyme substrates, photo multiplier tubes, spectrophotometers, scanning detectors, microscopes, galvo-scanners, and/or the like. In preferred embodiments the detector can independently detect signals from two or more detectable markers with different signals; e.g., a fluorometer detector that can simultaneously detect emissions at two or more frequencies.

Many of the above methods or systems can be used in combination. Additional features of the invention will become apparent upon review of the following.

DETAILED DESCRIPTION

Figure 1:
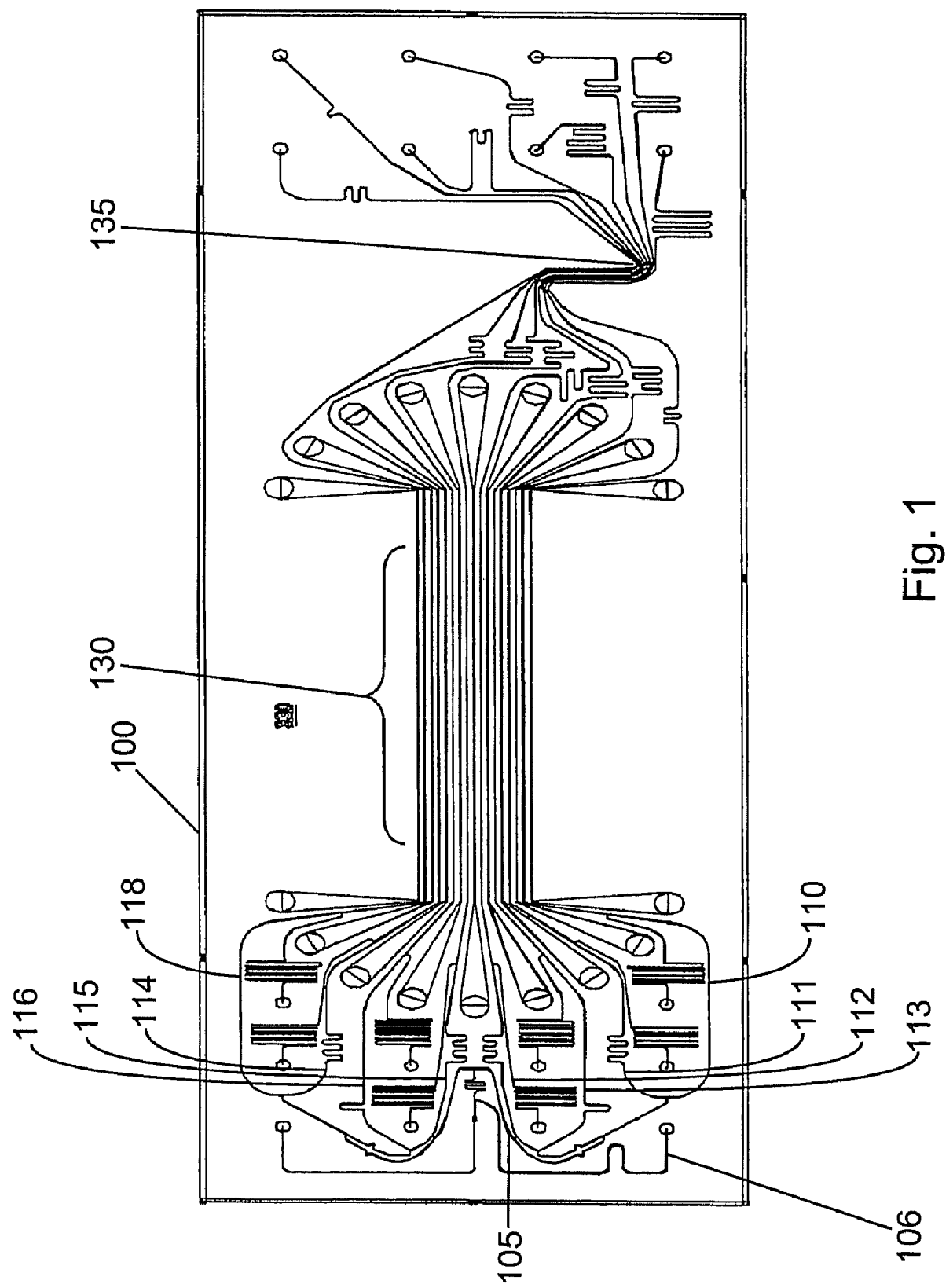
FIG. 1 schematically illustrates a chip design for an 8-channel PCR sipper chip used in many of the Examples herein.

The present invention derives, in part, from a surprising conceptual shift in considering how rare nucleic acids can be amplified and detected in or from a sample. In the past, detection of rare nucleic acids was performed by trying to find ways of improving the specificity and sensitivity of amplification and detection reactions. This is because the better the reaction can specifically amplify and identify a nucleic acid of interest, the better the reliability and throughput of the system. Considering a simple analogy, when trying to find a needle in a haystack, prior art thinking focuses on more efficient ways of extracting the needle from the haystack.

The present invention takes an entirely different approach to identifying nucleic acids of interest. Instead of trying to fish the nucleic acid of interest out of a complex sample directly, the entire sample is simply deconstructed into low copy number aliquots and the low copy number aliquots are subjected to amplification reactions and individual detection until the nucleic acid of interest is found. Continuing with the simple analogy, the entire haystack is broken apart into individual pieces of hay and each is examined to see if it is hay or needle. This low or single copy amplification concept can provide analyses with high sensitivity against a very low background.

Such low or single copy amplifications can be especially useful in the present invention for evaluation of a nucleic acid length. For example, hybridization of a dot blotted sample with a pair probes specific to opposite ends of a target nucleic acid can yield ambiguous results on the integrity of the target. Whether or not the target nucleic acid is fragmented, signals from both probes will be detected on the same blot. However, should the target be subjected to single copy amplification and hybridization with the probes in an isolated reaction mixture, detection of signals from both probes would indicate target not fragmented between sequences complementary to the probes. On the other hand, amplification and hybridization of a single copy target nucleic acid fragment would result in detection of a signal from only one of the probes. Therefore, coincident signals from two probes can indicate a full-length target and detection of a signal from only one of the probes can indicate the presence of a fragmented target in a single copy reaction.

Modern high-throughput systems make this new conceptual approach possible, i.e., the ability to run massively high numbers of amplification reactions at low cost, e.g., using microfluidic amplification technologies, makes it possible to much more exhaustively sample for any particular nucleic acid of interest in a sample. The continuous flow or high throughput stopped flow nature of these systems further facilitates the approach. Furthermore, examination of a sample by such exhaustive sampling methods provides a great deal of quantitative information (and the concomitant possibility of statistical analysis) with respect to the composition of the sample and the proportions of fragmented or unfragmented nucleic acid of interest. This, in turn, provides diagnostic and prognostic information associated with to the abundance (or relative abundance) of the nucleic acids of interest.

DEFINITIONS

It is to be understood that this invention is not limited to particular devices or biological systems, or amplification methods, which can, of course, vary. It is also to be understood that the terminology used herein is for the purpose of describing particular embodiments only, and is not intended to be limiting. As used in this specification and the appended claims, the singular forms "a", "an" and "the" optionally include plural referents unless the content clearly dictates otherwise. Thus, for example, reference to "a microfluidic device" optionally includes a combination of one, two or more devices.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

An "aliquot" is a portion of a component of interest (e.g., a sample or reaction mixture). The aliquot can be diluted, concentrated or undiluted as compared to the component of interest.

A "nucleic acid of interest" is any nucleic acid to be amplified, detected and/or quantified in a sample. A nucleic acid of interest can be detected and identified in fragmented form and/or in unfragmented form using methods and systems of the invention.

An "amplification reaction" is a reaction that 1) results in amplification of a template, or 2) would result in amplification of a template if the template were present. Thus, an "amplification reaction" can be performed on a sample aliquot that comprises a nucleic acid to be amplified, or on a sample aliquot that does not comprise the nucleic acid. Actual amplification of a template is not a requirement for performing an amplification reaction.

As used herein, a "reaction mixture" refers to a mixture of constituents of an amplification reaction and/or a hybridization reaction. An aliquot of a reaction mixture containing a nucleic acid of interest, or not, can still be considered a reaction mixture. A single copy reaction mixture includes constituents of a reaction mixture in a volume where a nucleic acid of interest, and any associated amplicons, do not overlap with another nucleic acid of interest or its associated amplicons.

A "zero copy" reaction mixture or aliquot is a reaction mixture or aliquot that has no copies of the relevant nucleic acid (e.g., a nucleic acid of interest, or an additional nucleic acid). It can comprise nucleic acids from a sample other than the relevant nucleic acid(s), or it can be completely devoid of any template nucleic acids from the sample.

A "single copy" reaction mixture has 1 copy of the relevant nucleic acid. The reaction mixture can be an amplification reaction mixture or hybridization mixture containing, e.g., a single copy of a nucleic acid of a given length, or fragment thereof.

A "low copy" reaction mixture or aliquot is a reaction mixture or aliquot that has only a few copies of the relevant nucleic acid(s). Typically, such a reaction will have 50 or fewer, generally 25 or fewer, usually 10 or fewer and often 5 or fewer, 2 or fewer or 1 or fewer copies of the relevant nucleic acid(s).

A "high copy" nucleic acid reaction mixture or aliquot has at least 1 order of magnitude more copies than the low copy number reaction mixture or aliquot, and generally 2, 3, 4, or even 5 or more orders of magnitude more than the low copy number reaction mixture.

A nucleic acid is "quantified" or "quantitated" in a sample when an absolute or relative amount of the nucleic acid in a sample is determined. This can be expressed as a number of copies, a concentration of the nucleic acid, a ratio or proportion of the nucleic acid to some other constituent of the sample (e.g., another nucleic acid), or any other appropriate expression.

A "given length" of a nucleic acid of interest, as used herein, refers to a distance between two probes hybridized to the nucleic acid plus the sequences complementary to the probes. The given length can be a known distance, measured, e.g., in units of base pairs, or an unknown distance determined to exist as an unfragmented sequence, e.g., by detection of coincident signals from a low or singly copy reaction mixture.

As used herein, the term "different probes" refers to probes complementary to or specifically hybridizing to different target sequences under stringent hybridization conditions.

As used herein, the term "different detectable markers" refers to detectable markers that provide signals distinguishable by a detector in the invention.

Nucleic Acids and Samples of Interest

The nucleic acid of interest to be detected in the methods of the invention can be essentially any nucleic acid. The sequences for many nucleic acids and amino acids (from which nucleic acid sequences can be derived via reverse translation) are available. No attempt is made to identify the hundreds of thousands of known nucleic acids, any of which can be detected in the methods of the invention. Common sequence repositories for known nucleic acids include GenBank EMBL, DDBJ and the NCBI. Other repositories can easily be identified by searching the internet. The nucleic acid can be an RNA (e.g., where amplification includes RT-PCR or LCR) or DNA (e.g., where amplification includes PCR or LCR), or an analogue thereof (e.g., for detection of synthetic nucleic acids or analogues thereof). Any variation in a nucleic acid can be detected, e.g., a mutation, a single nucleotide polymorphism (SNP), an allele, an isotype, a fragment, a full-length nucleic acid, an amplicon, etc. Further, because the present invention is quantitative, one can detect variations in expression levels, fragmentation, or gene copy numbers by the methods.

In general, the methods of the invention are particularly useful in screening samples derived from patients for the nucleic acids of interest, e.g., from bodily fluids and/or waste from the patient. This is because samples derived from relatively large volumes of such materials can be screened in the methods of the invention (removal of such materials is also relatively non-invasive). The nucleic acids of interest (e.g., present in cancer cells) can easily comprise 1% or less of the related nucleic acid population of the sample (e.g., about 1%, 0.1%, 0.001%, 0.0001% or less of the alleles for a gene of interest). Thus, whole blood, serum, plasma, stool, urine, vaginal secretions, ejaculatory fluid, synovial fluid, a biopsy, cerebrospinal fluid, and amniotic fluid, sputum, saliva, lymph, tears, sweat, or urine, or the like, can easily be screened for rare nucleic acids or fragmentation by the methods of the invention, as can essentially any tissue of interest. These samples are typically taken, following informed consent, from a patient by standard medical laboratory methods.

Prior to aliquotting and amplification, nucleic acids are optionally purified from the samples by any available method, e.g., those taught in Berger and Kimmel, *Guide to Molecular Cloning Techniques, Methods in Enzymology* volume 152 Academic Press, Inc., San Diego, Calif. ("Berger"); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); and/or *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel"). A plethora of kits are also commercially available for the purification of nucleic acids from cells or other samples (see, e.g., EasyPrep™, FlexiPrep™, both from Pharmacia Biotech; StrataClean™, from Stratagene; and, QIAprep™ from Qiagen). Alternately, samples can simply be directly subjected to amplification, e.g., following aliquotting and dilution. One advantage of single molecule detection is that the low concentration of sample components in the reaction can reduce the need for nucleic acid purification. That is, dilution of the sample reduces the abundance of unwanted components at the same time it distributes the nucleic acid of interest into reaction mixtures.

One preferred class of nucleic acids of interest to be detected in the methods herein are those involved in cancer. Any nucleic acid that is associated with cancer can be detected in the methods of the invention, e.g., those that encode over expressed or mutated polypeptide growth factors (e.g., sis), over expressed or mutated growth factor receptors (e.g., erb-B1), over expressed or mutated signal transduction proteins such as G-proteins (e.g., Ras), or non-receptor tyrosine kinases (e.g., abl), or over expressed or mutated regulatory proteins (e.g., myc, myb, jun, fos, etc.) and/or the like. In a preferred embodiment, specific or arbitrary nucleic acids of interest are screened for the amount of fragmentation, with high fragmentation generally associated with apoptosis of normal cells and less fragmentation associated, e.g., with sloughing of cancer cells. In general, cancer can often be linked to signal transduction molecules and corresponding oncogene products, e.g., nucleic acids encoding Mos, Ras, Raf, and Met; and transcriptional activators and suppressors, e.g., p53, Tat, Fos, Myc, Jun, Myb, Rel, and/or nuclear receptors. p53, colloquially referred to as the "molecular policeman" of the cell, is of particular relevance, as about 50% of all known cancers can be traced to one or more genetic lesion in p53.

Taking one class of genes that are relevant to cancer as an example for discussion, many nuclear hormone receptors have been described in detail and the mechanisms by which these receptors can be modified to confer oncogenic activity have been worked out. For example, the physiological and molecular basis of thyroid hormone action is reviewed in Yen (2001) "*Physiological and Molecular Basis of Thyroid Hormone Action*" *Physiological Reviews* 81(3):1097-1142, and the references cited therein. Known and well characterized nuclear receptors include those for glucocorticoids (GRs), androgens (ARs), mineralocorticoids (MRs), progestins (PRs), estrogens (ERs), thyroid hormones (IRs), vitamin D (VDRs), retinoids (RARs and RXRs), and the peroxisome proliferator activated receptors (PPARs) that bind eicosanoids. The so called "orphan nuclear receptors" are also part of the nuclear receptor superfamily, and are structurally homologous to classic nuclear receptors, such as steroid and thyroid receptors. Nucleic acids that encode any of these receptors, or oncogenic forms thereof, can be detected in the methods of the invention. About 40% of all pharmaceutical treatments currently available are agonists or antagonists of nuclear receptors and/or oncogenic forms thereof, underscoring the relative importance of these receptors (and their coding nucleic acids) as targets for analysis by the methods of the invention.

As already mentioned, one preferred class of nucleic acids of interest are those that are diagnostic of colon cancer, e.g., in samples derived from stool. Colon cancer is a common disease that can be sporadic or inherited. The molecular basis of various patterns of colon cancer is known in some detail. In general, germline mutations are the basis of inherited colon cancer syndromes, while an accumulation of somatic mutations is the basis of sporadic colon cancer. In Ashkenazi Jews, a mutation that was previously thought to be a polymorphism may cause familial colon cancer. Mutations of at least three different classes of genes have been described in colon cancer etiology: oncogenes, suppressor genes, and mismatch repair genes. One example nucleic acid encodes DCC (deleted in colon cancer), a cell adhesion molecule with homology to fibronectin. An additional form of colon cancer is an autosomal dominant gene, hMSH2, that comprises a lesion. Familial adenomatous polyposis is another form of colon cancer with a lesion in the MCC locus on chromosome #5. For additional details on Colon Cancer, see, Calvert et al. (2002) "The Genetics of Colorectal Cancer" *Annals of Internal Medicine* 137 (7): 603-612 and the references cited therein. For a variety of colon cancers and colon cancer markers that can be detected in stool, see, e.g., Boland (2002) "Advances in Colorectal Cancer Screening: Molecular Basis for Stool-Based DNA Tests for Colorectal Cancer: A Primer for Clinicians" *Reviews In Gastroenterological Disorders* Volume 2, Supp. 1 and the references cited therein. As with other cancers, mutations in a variety of other genes that correlate with cancer, such as Ras and p53, are useful diagnostic indicators for cancer. In another aspect, detection of fragmentation levels using methods of the present invention can be particularly useful in detection of colon cancer. For example, as the amount of total patient DNA available in a stool specimen is low, the amplification aspect of the present invention can be beneficial to examination of the DNA. Whereas the DNA from cells sloughed from the normal colon lining is generally degraded into fragments, e.g., of about 100 base pairs in length, DNA entering the colon lumen from a colon tumor cells can remain generally unfragmented. Detecting the presence of a proportion of unfragmented nucleic acids over a certain threshold in a stool specimen can correlate to presence of a colon cancer.

Cervical cancer is another preferred target for detection, e.g., in samples obtained from vaginal secretions. Cervical cancer can be caused by the papova virus and has two oncogenes, E6 and E7. E6 binds to and removes p53 and E7 binds to and removes PRB. The loss of p53 and uncontrolled action of E2F/DP growth factors without the regulation of pRB is one mechanism that leads to cervical cancer. Furthermore, as with colon cancer, detecting the presence of a proportion of unfragmented nucleic acids over a certain threshold in a vaginal swab can correlate to the presence of a cervical cancer.

Another preferred target for detection by the methods of the invention is retinoblastoma, e.g., in samples derived from tears. Retinoblastoma is a tumor of the eyes which results from inactivation of the pRB gene. It has been found to transmit heritably when a parent has a mutated pRB gene (and, of course, somatic mutation can cause non-heritable forms of the cancer).

Neurofibromatosis Type 1 can be detected in the methods of the invention. The NF1 gene is inactivated, which activates the GTPase activity of the ras oncogene. If NF1 is missing, ras is overactive and causes neural tumors. The methods of the invention can be used to detect Neurofibromatosis Type 1 in CSF or via tissue sampling.

Many other forms of cancer are known and can be found by detecting, e.g., associated genetic lesions, fragmentation proportions, or absolute concentrations of full-length nucleic acids of interest using the methods of the invention. Cancers that can be detected by detecting appropriate lesions or fragmentation values include cancers of the lymph, blood, stomach, gut, colon, testicles, pancreas, bladder, cervix, uterus, skin, and essentially all others for which an associated genetic lesion or fragmentation threshold exists. For a review of the topic, see, *The Molecular Basis of Human Cancer* Coleman and Tsongalis (Eds) Humana Press; ISBN: 0896036340; 1st edition (August 2001).

Similarly, nucleic acids from pathogenic or infectious organisms can be detected by the methods of the invention, e.g., for infectious fungi, e.g., *Aspergillus*, or *Candida* species; bacteria, particularly *E. coli*, which serves a model for pathogenic bacteria (and, of course certain strains of which are pathogenic), as well as medically important bacteria such as Staphylococci (e.g., *aureus*), or Streptococci (e.g., *pneumoniae*); protozoa such as sporozoa (e.g., *Plasmodia*), rhizopods (e.g., *Entamoeba*) and flagellates (*Trypanosoma, Leishmania, Trichomonas, Giardia*, etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B. Single and low copy amplification methods of the invention can be useful in many cases, e.g., in exudates from bacterial infections to identify living (having full length nucleic acids) versus dead and lysed pathogens (having fragmented nucleic acids).

A variety of nucleic acid encoding enzymes (e.g., industrial enzymes) can also be detected according to the methods herein, such as amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases. Similarly, agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase can also be detected.

Aliquotting the Sample

The sample can be aliquoted and/or diluted using standard or microfluidic fluid handling approaches (or combinations thereof). Standard fluid handling approaches for dilution/aliquotting include, e.g., pipetting appropriate volumes of the sample into microtiter trays and adding an appropriate diluent. These operations can be performed manually or using available high throughput fluid handlers, such as, e.g., those designed to use serially dilute solutions in microtiter trays. High throughput equipment (e.g., incorporating automated pipettors and robotic microtiter tray handling) is preferred, as the present invention contemplates making and using high numbers of aliquots of a sample of interest.

Many automated systems for fluid handling are commercially available and can be used for aliquotting and/or diluting a sample in the context of the present invention. For example, a variety of automated systems are available from the Zymark Corporation (Zymark Center, Hopkinton, Mass.), which utilize various Zymate systems (see also, http://www.zymark.com/), which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). In any case, a conventional high throughput systems can be used in place of, or in conjunction with microfluidic systems (for example, conventional systems can be used to aliquot samples into microtiter trays, from which microfluidic systems can draw materials) in practicing the methods of the invention.

In one aspect, emulsions are created, where sample aliquots comprise or consist of droplets within the emulsions. The emulsions can be amplified by standard thermocyclic reactions and amplified nucleic acids detected within droplets of the emulsions using standard equipment (e.g., flow cytometers, microscope stations, or CCD arrays).

Microfluidic systems provide a preferred fluid handling and amplification technology that can conveniently be applied to the present invention. In typical embodiments, samples are drawn into microfluidic devices that comprise networks of microscale cavities (channels, chambers, etc., having at least one dimension less than about 500 µM in size and often less than about 100 µM) and the samples are mixed, diluted, aliquoted or otherwise manipulated in the network of cavities (e.g., channels and/or chambers). For example, the microscale device can comprise one or more capillary, in fluid communication with the network, extending outward from a body structure of the microscale device. Negative pressure (vacuum) is applied to the capillary and fluids are drawn into the network from a container (e.g., a well on a microtiter tray). This process can be multiplexed by using a device that comprises multiple capillary channels, permitting many samples to be drawn into the network and processed simultaneously. Alternately, multiple samples can be sequentially drawn into the microfluidic device and routed internally to multiple channels for simultaneous processing and analysis. Sample interfaces with dried samples can also be performed using this basic system, e.g., by partly or completely expelling fluid from the capillary to hydrate samples prior to drawing them into the microfluidic device (the fluid is typically contacted to the samples as a hanging drop on the tip of the capillary and then drawn back into the capillary). For either approach, see also, U.S. Pat. No. 6,482,364 to Parce, et al. (Nov. 19, 2002) MICROFLUIDIC SYSTEMS INCLUDING PIPETTOR ELEMENTS; U.S. Pat. No. 6,042,709 to Parce, et al. (Mar. 28, 2000) MICROFLUIDIC SAMPLING SYSTEM AND METHODS; U.S. Pat. No. 6,287,520 to Parce, et al. (Sep. 11, 2001) ELECTROPIPETTOR AND COMPENSATION MEANS FOR ELECTROPHORETIC BIAS and U.S. Pat. No. 6,235,471 to Knapp, et al. (May 22, 2001) CLOSED-LOOP BIOCHEMICAL ANALYZERS. Essentially any fluid manipulation (aliquotting, diluting, heating and cooling) can be performed in the network using available methods. Details regarding dilution and aliquotting operations in microscale devices can be found in the patent literature, e.g., U.S. Pat. No. 6,149,870 to Parce, et al. (Nov. 21, 2000) APPARATUS FOR IN SITU CONCENTRATION AND/OR DILUTION OF MATERIALS IN MICROFLUIDIC SYSTEMS; U.S. Pat. No. 5,869,004 to Parce, et al. (Feb. 9, 1999) METHODS AND APPARATUS FOR IN SITU CONCENTRATION AND/OR DILUTION OF MATERIALS IN MICROFLUIDIC SYSTEMS; and U.S. Pat. No. 6,440,722 to Knapp, et al. (Aug. 27, 2002) MICROFLUIDIC DEVICES AND METHODS FOR OPTIMIZING REACTIONS. Samples and components to be mixed/diluted or aliquoted can be brought into the microscale device through pipettor elements or from reaction component reservoirs on the device itself, or, commonly, both. For example, the sample can be brought into the microfluidic device through a pipettor channel and diluted and supplied with common reagents from an on device dilution and/or reagent reservoir(s). Locus specific reagents (e.g., amplification primer pairs) can be on the device in wells, or stored off the device, e.g., in microtiter plates (in which case they can be accessed by the pipettor channel). Any or all of these operations can be performed in a continuous or stopped flow format.

The functions the chip performs typically include reaction assembly (assembly of reaction mixtures), thermocycling, and acting as a "cuvette" for an optical system during an imaging (detection) step. In the reaction assembly, the reaction mixture components (particularly magnesium and the enzyme) which get combined at the last second before heating begins are assembled. This is called a "hot start" and provides advantages of specificity. During thermocycling, the system optionally provides both constant fluid movement and a continuous sequence of temperature changes. During imaging, a high data rate CCD is useful in providing an adequate dynamic range using the dispersion/diffusion methods of quantification.

Commercial systems that perform all aspects of fluid handling and analysis that can be used in the practice of the present invention are available. Examples include the 250 HTS system and AMS 90 SE from Caliper Technologies (Mountain View, Calif.). These systems performs experiments in serial, continuous flow fashion and employ a "chip-to-world" interface, or sample access system, called a sipper through which materials in microwell plates are sipped into a capillary or capillaries attached to the chip and drawn into the channels of the chip. There they are mixed with components of interest and a processing and result detection steps are performed.

Whether conventional fluid handling or microfluidic approaches (or both) are used, the aliquotting and/or dilution events can be performed to achieve particular results. For example, a sample can be diluted equally in each aliquot, or, alternately, the aliquots can be differentially diluted (e.g., a dilution series can be made). The aliquots themselves can be of a volume that is appropriate to the fluid handling approach being used by the system, e.g., on the order of a few microliters for microtiter plates to 100 nL, 10 nL or even 1 nL or less for microfluidic approaches.

The aliquots can be selected to have high or low copy numbers of any relevant nucleic acid (e.g., for low copy number aliquots, 50 or fewer, generally 25 or fewer, usually 10 or fewer and often 5 or fewer, 2 or fewer or 1 or fewer copies of the relevant nucleic acid(s)). The number of aliquots generated will depend on the size of the sample and the amount of quantitative information desired by the practitioner. For example, where simple detection of a rare nucleic acid is desired, enough low and/or single copy number aliquots are made of the sample to detect the nucleic acid in one of the aliquots. Where more quantitative information is needed, enough copies are made to provide reliable statistical information, e.g., to a given confidence value. In either case, this can include anywhere from 1 aliquot to 109 or more aliquots, e.g., 10, 100, 1,000, 10,000, 100,000, 1,000,000, 1,000,000,000 or more aliquots. There is no theoretical limit on the number of aliquots that can be made and assessed for a nucleic acid of interest according to the present invention, though there are practical considerations with respect to the throughput of the system and the size of the sample (the lower the throughput, the fewer aliquots can be analyzed in a given time; the larger the sample size the more aliquots can be made of the sample). Using microfluidic approaches, reagent usage (and concomitant reagent costs) can be minimized. By formatting the system to provide for continuous flow of sample and reagents, including, optionally, during amplification, the systems of the invention can greatly speed the process of searching many different samples for a nucleic acid of interest. Similarly, if stopped flow approaches are used, simultaneous processing of signals from PCR reactions can be used to speed the process of searching samples for a nucleic acid of interest. In the examples below, about 150 aliquots for each dilution range was sufficient to provide reasonable quantitative information for Poisson statistics for model samples. Obviously, more or fewer aliquots can be used in the methods as well.

In many of the embodiments herein, it is worth noting that many of the aliquots will have zero copies of the nucleic acid of interest, due to the rarity of the relevant nucleic acid in the sample (and the dilution that is chosen). This does not present a detection problem in a continuous flow analysis system— the flow rate can be used to calculate how many aliquots have passed (undetected) by a detector prior to detection of the nucleic acid of interest. In non-continuous flow systems (e.g., microwell plate based systems), one can simply count blank reactions (wells lacking amplification product) to determine the frequency of amplification of the nucleic acid of interest. In any event, anywhere from 1 to 106 or more zero copy reactions can be made and assessed by the system, e.g., about 10, 25, 50, 100, 500, 1,000, 10,000, 100,000, or 1,000,000 or more zero copy reactions can be detected in the process of detecting a nucleic acid of interest. Similarly, additional nucleic acids other than the nucleic acid of interest (e.g., controls, or alternate alleles of a nucleic acid of interest that are also amplified by the relevant locus specific reagent) can be detected (or not detected) by the system. The proportion of such alternate nucleic acids in the system to the nucleic acid of interest can range from less than 1 to $10^9$ or more, e.g., 1×, 10×, 100×, 1,000×, 10,000×, 100,000×, 1,000,000×, 1,000,000,000× or more.

Furthermore, as demonstrated in the examples and figures herein, the continuous flow format is a surprisingly efficient system, meaning that a high proportion of single molecules that get into the system are amplified. This efficiency is useful in ensuring that very rare molecules are detected, if present, for example in a biowarfare or infectious disease detection applications. Evidence for high efficiency is in the examples, tables and figures herein. Typically, the systems of the invention can be used to amplify at least 90%, generally 95%, often 99% or more of the rare molecules that are present in sample of interest, or that are present in a collection of aliquots that are subjected to amplification. Efficiency factors can be determined, e.g., empirically, for adjustment of mathematical formulas for more accurate quantitative interpretations of signal data.

Amplifying the Aliquots

The methods of the invention include amplifying one or more sequences of a nucleic acid of interest from a sample or aliquot and, optionally, one or more additional nucleic acids. Typically two or more sequences of a nucleic acid of interest are amplified at separated positions to allow interpretation of the nucleic acid length. Any available amplification method can be used, including PCR, RT-PCR, LCR, and/or any of the various RNA mediated amplification methods. PCR, RT-PCR and LCR are preferred amplification methods for amplifying a nucleic acid of interest in the methods of the invention. Real time PCR and/or RT-PCR (e.g., mediated via TaqMan™ probes or molecular beacon-based probes) can also be used to facilitate detection of amplified nucleic acids.

It is expected that one of skill is generally familiar with the details of these amplification methods. Details regarding these amplification methods can be found, e.g., in Sambrook (2000); Ausubel (2002) and Innis (1990), all above. Additional details can be found in PCR: A Practical Approach (The Practical Approach Series) by Quirke et al. (eds.). (1992) by Oxford University Press.

Additional details can also be found in the literature for a variety of applications of PCR. For example, details regarding amplification of nucleic acids in plants can be found, e.g., in Plant Molecular Biology (1993) Croy (ed.) BIOS Scientific Publishers, Inc. Similarly, additional details regarding PCR for cancer detection can be found in any of a variety of sources, e.g., Bernard and Wittwer (2002) "Real Time PCR Technology for Cancer Diagnostics Clinical Chemistry 48(8):1178-1185; Perou et al. (2000) "Molecular portraits of human breast tumors" Nature 406:747-52; van't Veer et al. (2002) "Gene expression profiling predicts clinical outcome of breast cancer" Nature 415:530-6; Rosenwald et al. (2001) "Relation of gene expression phenotype to immunoglobulin mutation genotype in B cell chronic lymphocytic leukemia" J Exp Med 194: 1639-47; Alizadeh et al. (2000) "Distinct types of diffuse large B-cell lymphoma identified by gene expression profiling" Nature 403:503-11; Garber et al. (2001) "Diversity of gene expression in adenocarcinoma of the lung" Proc Natl Acad Sci USA 98: 1378-49; Tirkkonen et al. (1998) "Molecular cytogenetics of primary breast cancer by CGH" Genes Chromosomes Cancer 21:177-84; Watanabe et al. (2001) "A novel amplification at 17q21-23 in ovarian cancer cell lines detected by comparative genomic hybridization" Gynecol Oncol 81:172-7, and many others.

Molecular Beacons

In one aspect, real time PCR is performed on the various aliquots or reaction mixtures described herein, e.g., using molecular beacons or TaqMan™ probes. A molecular beacon (NB) is an oligonucleotide or PNA which, under appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched.

Details regarding standard methods of making and using MBs are well established in the literature and MBs are available from a number of commercial reagent sources. See also, e.g., Leone et al. (1995) "Molecular beacon probes combined with amplification by NASBA enable homogenous real-time detection of RNA." Nucleic Acids Res. 26:2150-2155; Tyagi and Kramer (1996) "Molecular beacons: probes that fluoresce upon hybridization" Nature Biotechnology 14:303-308; Blok and Kramer (1997) "Amplifiable hybridization probes containing a molecular switch" Mol Cell Probes 11:187-194; Hsuih et al. (1997) "Novel, ligation-dependent PCR assay for detection of hepatitis C in serum" J Clin Microbiol 34:501-507; Kostrikis et al. (1998) "Molecular beacons: spectral genotyping of human alleles" Science 279:1228-1229; Sokol et al. (1998) "Real time detection of DNA:RNA hybridization in living cells" Proc. Natl. Acad. Sci. U.S.A. 95:11538-11543; Tyagi et al. (1998) "Multicolor molecular beacons for allele discrimination" Nature Biotechnology 16:49-53; Bonnet et al. (1999) "Thermodynamic basis of the chemical specificity of structured DNA probes" Proc. Natl. Acad. Sci. U.S.A. 96:6171-6176; Fang et al. (1999) "Designing a novel molecular beacon for surface-immobilized DNA hybridization studies" J. Am. Chem. Soc. 121:2921-2922; Marras et al. (1999) "Multiplex detection of single-nucleotide variation using molecular beacons" Genet. Anal. Biomol. Eng. 14:151-156; and Vet et al. (1999) "Multiplex detection of four pathogenic retroviruses using molecular beacons" Proc. Natl. Acad. Sci. U.S.A. 96:6394-6399. Additional details regarding MB construction and use is found in the patent literature, e.g., U.S. Pat. No. 5,925,517 (Jul. 20, 1999) to Tyagi et al. entitled "Detectably labeled dual conformation oligonucleotide probes, assays and kits;" U.S. Pat. No. 6,150,097 to Tyagi et al (Nov. 21, 2000) entitled "Nucleic acid detection probes having non-FRET fluorescence quenching and kits and assays including such probes" and U.S. Pat. No. 6,037,130 to Tyagi et al (Mar. 14, 2000), entitled "Wavelength-shifting probes and primers and their use in assays and kits."

MBs are robust reagents for detecting and quantifying nucleic acids, including in real time, e.g., during PCR, LCR or other nucleic acid amplification reactions (e.g., MBs can be used to detect targets as they are formed). A variety of commercial suppliers produce standard and custom molecular beacons, including Cruachem (cruachem.com), Oswel Research Products Ltd. (UK; oswel.com), Research Genetics (a division of Invitrogen, Huntsville Ala. (resgen.com)), the Midland Certified Reagent Company (Midland, Tex. mcrc.com) and Gorilla Genomics, LLC (Alameda, Calif.). A variety of kits which utilize molecular beacons are also commercially available, such as the Sentinel™ Molecular Beacon Allelic Discrimination Kits from Stratagene (La Jolla, Calif.) and various kits from Eurogentec SA (Belgium, eurogentec.com) and Isogen Bioscience BV (The Netherlands, isogen.com).

MB components (e.g., oligos, including those labeled with fluorophores or quenchers) can be synthesized using conventional methods. For example, oligos or peptide nucleic acids (PNAs) can be synthesized on commercially available automated oligonucleotide/PNA synthesis machines using standard methods. Labels can be attached to the oligos or PNAs either during automated synthesis or by post-synthetic reactions which have been described before see, e.g., Tyagi and Kramer (1996) "Molecular beacons: probes that fluoresce upon hybridization" Nature Biotechnology 14:303-308 and U.S. Pat. No. 6,037,130 to Tyagi et al (Mar. 14, 2000), entitled "Wavelength-shifting probes and primers and their use in assays and kits." and U.S. Pat. No. 5,925,517 (Jul. 20, 1999) to Tyagi et al. entitled "Detectably labeled dual conformation oligonucleotide probes, assays and kits." Additional details on synthesis of functionalized oligos can be found in Nelson, et al. (1989) "Bifunctional Oligonucleotide Probes Synthesized Using A Novel CPG Support Are Able To Detect Single Base Pair Mutations" Nucleic Acids Research 17:7187-7194. Labels/quenchers can be introduced to the oligonucleotides or PNAs, e.g., by using a controlled-pore glass column to introduce, e.g., the quencher (e.g., a 4-dimethylaminoazobenzene-4'-sulfonyl moiety (DABSYL). For example, the quencher can be added at the 3' end of oligonucleotides during automated synthesis; a succinimidyl ester of 4-(4'-dimethylaminophenylazo)benzoic acid (DABCYL) can be used when the site of attachment is a primary amino group; and 4-dimethylaminophenylazophenyl-4'-maleimide (DABM) can be used when the site of attachment is a sulphydryl group. Similarly, fluorescein can be introduced in the oligos, either using a fluorescein phosphoramadite that replaces a nucleoside with fluorescein, or by using a fluorescein dT phosphoramadite that introduces a fluorescein moiety at a thymidine ring via a spacer. To link a fluorescein moiety to a terminal location, iodoacetoamidofluorescein can be coupled to a sulphydryl group. Tetrachlorofluorescein (TET) can be introduced during automated synthesis using a 5'-tetrachloro-fluorescein phosphoramadite. Other reactive fluorophore derivatives and their respective sites of attachment include the succinimidyl ester of 5-carboxyrhodamine-6G (RHD) coupled to an amino group; an iodoacetamide of tetramethylrhodamine coupled to a sulphydryl group; an isothiocyanate of tetramethylrhodamine coupled to an amino group; or a sulfonylchloride of Texas red coupled to a sulphydryl group. During the synthesis of these labeled components, conjugated oligonucleotides or PNAs can be purified, if desired, e.g., by high pressure liquid chromatography or other methods.

TagMan™ Probes

PCR quantification using dual-labeled fluorogenic oligonucleotide probes, commonly referred to as "TaqMan™" probes, can be performed according to the present invention. These probes are composed of short (e.g., 20-25 base) oligodeoxynucleotides that are labeled with two different fluorescent dyes. On the 5 terminus of each probe is a reporter dye, and on the 3' terminus of each probe a quenching dye is found. The oligonucleotide probe sequence can be complementary to an internal target sequence present in a PCR amplicon. When the probe is intact, energy transfer occurs between the two fluorophores and emission from the reporter is quenched by the quencher (fluorescent resonant energy transfer or FRET). During the extension phase of PCR, the probe is cleaved by 5' nuclease activity of the polymerase used in the reaction, thereby releasing the reporter from the oligonucleotide-quencher and producing an increase in reporter emission intensity.

Accordingly, TaqMan™ probes are oligonucleotides that have a label and a quencher, where the label is released after hybridization and during amplification by the exonuclease action of the polymerase used in amplification. This provides a real time measure of amplification during synthesis. A variety of TaqMan™ reagents are commercially available, e.g., from Applied Biosystems (Division Headquarters in Foster City, Calif.) as well as from a variety of specialty vendors such as Biosearch Technologies (e.g., black hole quencher probes).

General Probe Synthesis Methods

In general, synthetic methods for making oligonucleotides, including probes, molecular beacons, PNAs, LNAs (locked nucleic acids), etc., are well known. For example, oligonucleotides can be synthesized chemically according to the solid phase phosphoramidite triester method described by Beaucage and Caruthers (1981), *Tetrahedron Letts.*, 22(20):1859-1862, e.g., using a commercially available automated synthesizer, e.g., as described in Needham-VanDevanter et al. (1984) *Nucleic Acids Res.,* 12:6159-6168. Oligonucleotides, including modified oligonucleotides can also be ordered from a variety of commercial sources known to persons of skill. There are many commercial providers of oligo synthesis services, and thus this is a broadly accessible technology. Any nucleic acid can be custom ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, Calif.) and many others. Similarly, PNAs can be custom ordered from any of a variety of sources, such as PeptidoGenic (pkim@ccnet.com), HTI Bio-products, inc. (www.htibio.com), BMA Biomedicals Ltd (U.K.), Bio-Synthesis, Inc., and many others.

Amplification in Microfluidic Systems

A number of high throughput approaches to performing PCR and other amplification reactions have been developed, e.g., involving amplification reactions in microfluidic devices, as well as methods for detecting and analyzing amplified nucleic acids in or on the devices. Details regarding such technology is found, e.g., in the technical and patent literature, e.g., Kopp et al. (1998) "Chemical Amplification: Continuous Flow PCR on a Chip" *Science,* 280 (5366):1046; U.S. Pat. No. 6,444,461 to Knapp, et al. (Sep. 3, 2002) MICROFLUIDIC DEVICES AND METHODS FOR SEPARATION; U.S. Pat. No. 6,406,893 to Knapp, et al. (Jun. 18, 2002) MICROFLUIDIC METHODS FOR NON-THERMAL NUCLEIC ACID MANIPULATIONS; U.S. Pat. No.

6,391,622 to Knapp, et al. (May 21, 2002) CLOSED-LOOP BIOCHEMICAL ANALYZERS; U.S. Pat. No. 6,303,343 to Kopf-Sill (Oct. 16, 2001) INEFFICIENT FAST PCR; U.S. Pat. No. 6,171,850 to Nagle, et al. (Jan. 9, 2001) INTEGRATED DEVICES AND SYSTEMS FOR PERFORMING TEMPERATURE CONTROLLED REACTIONS AND ANALYSES; U.S. Pat. No. 5,939,291 to Loewy, et al. (Aug. 17, 1999) MICROFLUIDIC METHOD FOR NUCLEIC ACID AMPLIFICATION; U.S. Pat. No. 5,955,029 to Wilding, et al. (Sep. 21, 1999) MESOSCALE POLYNUCLEOTIDE AMPLIFICATION DEVICE AND METHOD; U.S. Pat. No. 5,965,410 to Chow, et al. (Oct. 12, 1999) ELECTRICAL CURRENT FOR CONTROLLING FLUID PARAMETERS IN MICROCHANNELS; Service (1998) "Microchips Arrays Put DNA on the Spot" *Science* 282:396-399), Zhang et al. (1999) "Automated and Integrated System for High-Throughput DNA Genotyping Directly from Blood" *Anal. Chem.* 71:1138-1145 and many others.

For example, U.S. Pat. No. 6,391,622 to Knapp, et al. (May 21, 2002) CLOSED-LOOP BIOCHEMICAL ANALYZERS and the references cited therein describes systems comprising microfluidic elements that can access reagent storage systems and that can perform PCR or other amplification reactions by any of a variety of methods in the microfluidic system. For example, the microfluidic system can have one or more capillaries extending outwards from the body structure of the microfluidic system for drawing materials into the body structure. Within the body structure are microfluidic cavities (channels, chambers, or the like having at least one dimension smaller than about 500 microns, and, typically smaller than about 100 microns) in which the amplification reactions are performed. The capillaries that extend out from the body structure can access standard reagent storage elements (microtiter plates, or the like) by drawing fluid into the capillary, e.g., due to application of a vacuum or electroosmotic force. Similarly, the capillaries can access dried reagent libraries on substrates (e.g., the LibraryCard™ reagent array made by Caliper Technologies) by partly or completely expelling fluid to rehydrate library members and then by drawing the rehydration fluid back into the capillary. For example, the capillary can partly expel fluid to form a hanging drop on the capillary, which is then contacted to the material to be hydrated. The material in the hanging drop is then drawn back into the capillary. In any case, molecular beacons or TaqMan™ probes can be incorporated into the relevant amplification reaction and detected in the microfluidic device to provide for real time PCR detection. Alternately, PCR amplicons can be detected by conventional methods, such as hybridization to a labeled probe, e.g., prior to or following a separation operation that separates unhybridized probe from hybridized probe. For example, an electrophoretic separation can be performed in a channel of the microscale device.

Conventional High Throughput Systems

In an alternative embodiment, standard fluid handling approaches are used in place of, or in conjunction with, microfluidic approaches. PCR can be performed in standard reaction vessels (e.g., microtiter plates), as can dilutions or other operations relevant to the present invention. Various high-throughput systems are available for non-microfluidic approaches to fluid handling (typically involving plates comprising several reaction chambers, e.g., 96 well, 384 well or 1536 well microtiter plates). These approaches can utilize conventional robotics to perform fluid handling operations and can use conventional commercially available thermocyclers to perform amplification reactions. See above, for a discussion of automated fluid handling systems.

Detecting the Amplified Nucleic Acids

Any available method for detecting amplified nucleic acids can be used in the present invention. Common approaches include real time amplification detection with molecular beacons or TaqMan™ probes, detection of intercalating dyes (ethidium bromide or sybergreen), detection of labels incorporated into the amplification probes or the amplified nucleic acids themselves, e.g., following electrophoretic separation of the amplification products from unincorporated label), and/or detection of secondary reagents that bind to the nucleic acids. Details on these general approaches is found in the references cited herein, e.g., Sambrook (2000), Ausubel (2002), and the references in the sections herein related to real time PCR detection. Additional labeling strategies for labeling nucleic acids and corresponding detection strategies can be found, e.g., in Haugland (1996) *Handbook of Fluorescent Probes and Research Chemicals Sixth Edition* by Molecular Probes, Inc. (Eugene Oreg.); or Haugland (2001) *Handbook of Fluorescent Probes and Research Chemicals Eighth Edition* by Molecular Probes, Inc. (Eugene Oreg.) (Available on CD ROM).

Amplified nucleic acids (amplicons) can be detected in homogenous (substantially unseparated) reaction mixtures or solutions (e.g., using molecular beacons or TaqMan™ probes) or during or after separation (e.g., by electrophoresis). Details on these strategies can be found in the preceding references.

Amplification and detection are commonly integrated in a system comprising a microfluidic device in the present invention. Available microfluidic systems that include detection features for detecting nucleic acids include the 250 HTS system and AMS 90 SE from Caliper Technologies (Mountain View, Calif.), as well as the Agilent 2100 bioanalyzer (Agilent, Palo Alto, Calif.). Additional details regarding systems that comprise detection (and separation/detection) capabilities are well described in the patent literature, e.g., the references already noted herein and in Parce et al. "High Throughput Screening Assay Systems in Microscale Fluidic Devices" WO 98/00231.

In general, the devices herein optionally include signal detectors, e.g., which detect fluorescence, phosphorescence, radioactivity, pH, charge, absorbance, luminescence, temperature, magnetism or the like. Fluorescent detection is especially preferred and generally used for detection of amplified nucleic acids (however, upstream and/or downstream operations can be performed on amplicons, which can involve other detection methods, such as mass spectroscopy or size exclusion).

The detector(s) optionally monitor one or a plurality of signals from an amplification reaction and/or hybridization reaction. For example, the detector can monitor optical signals which correspond to "real time" amplification assay results. The detector can monitor a single type of signal, or, e.g., simultaneously monitor multiple different signals.

Example detectors include photo multiplier tubes, spectrophotometers, CCD arrays, scanning detectors, microscopes, galvo-scans and/or the like. Amplicons or other components which emit a detectable signal can be flowed past the detector, or, alternatively, the detector can move relative to the site of the amplification reaction (or, the detector can simultaneously monitor a number of spatial positions corresponding to channel regions, or microtiter wells e.g., as in a CCD array). Detectors in the present invention can detect signals from probes associated with nucleic acids of the invention that flow into one or more detection regions, e.g., of a microfluidic device.

The detector can include or be operably linked to a computer (or other logic device), e.g., which has software for converting detector signal information into assay result information (e.g., presence of a nucleic acid of interest, the length of a nucleic acid of interest, proportions of nucleic acid of interest lengths, and/or correlations with disease states), or the like.

Signals are optionally calibrated, e.g., by calibrating the microfluidic system by monitoring a signal from a known source. For example, signals can be calibrated against a reference light source, internal reference signals, or normalized for detection of positive signals over background.

A microfluidic system can also employ multiple different detection systems for monitoring signals in the system. Detection systems of the present invention are used to detect and monitor the materials in a particular channel region (or other reaction detection region). Once detected, the flow rate and velocity of any cells or droplets in the channels can be optionally measured by sensors and controlled as described above.

Examples of detection systems useful in methods and systems of the invention can include optical sensors, temperature sensors, pressure sensors, pH sensors, conductivity sensors, and the like. Each of these types of sensors is readily incorporated into the microfluidic systems described herein. In these systems, such detectors can be placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems include optical detection systems for detecting an optical property of a material within the channels and/or chambers of the microfluidic devices that are incorporated into the microfluidic systems described herein. Such optical detection systems are typically placed adjacent to a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials spectral characteristics. In preferred aspects, the detector measures an amount of light emitted from the material, such as a fluorescent or chemiluminescent material. As such, the detection system will typically include collection optics for gathering a light based signal transmitted through the detection window, and transmitting that signal to an appropriate light detector. Microscope objectives of varying power, field diameter, and focal length are readily utilized as at least a portion of this optical train. The light detectors are optionally spectrophotometers, photodiodes, avalanche photodiodes, photomultiplier tubes, diode arrays, or in some cases, imaging systems, such as charged coupled devices (CCDs) and the like. The detection system is typically coupled to a computer, via an analog to digital or digital to analog converter, for transmitting detected light data to the computer for analysis, storage and data manipulation.

In the case of fluorescent materials such as labeled amplicons, the detector typically includes a light source that produces light at an appropriate wavelength for activating the fluorescent material, as well as optics for directing the light source through the detection window to the material contained in the channel or chamber. The light source can be any number of light sources that provides an appropriate wavelength, including lasers, laser diodes, and LEDs. Other light sources are used in other detection systems. For example, broad band light sources are typically used in light scattering/transmissivity detection schemes, and the like. Typically, light selection parameters are well known to those of skill in the art.

The detector can exist as a separate unit, but can also be integrated with the system or microfluidic device, into a single instrument. Integration of these functions into a single unit facilitates connection of these instruments with the computer, by permitting the use of few or a single communication port(s) for transmitting information between the controller, the detector and the computer.

Counting and Statistically Analyzing Nucleic Acids of Interest

One feature of the present invention is that it provides for robust quantitation of rare (and other) nucleic acids in a sample. This robust quantitation provides the ability to perform statistical or probabilistic analysis of the sample. For example, Poisson analysis, Monte Carlo analysis, application of genetic algorithms, neural network training, Markov modeling, hidden Markov modeling, multidimensional scaling, partial least squares (PLS) analysis, or principle component analysis (PCA) can all be applied to data generated by the present invention. These statistical evaluations can be used to determine, e.g., the concentration, abundance, or length proportions of a given nucleic acid in a sample and to correlate abundance or proportions to diagnosis or prognosis associated with the diagnosis or prognosis.

General references that are useful in understanding how to generate and analyze data, as well as other relevant concepts include: Neil Weiss (1999) *Introductory Statistics & Elementary Statistics Edition:* $5^{th}$ ISBN: 0201434490; Berinstein (1998) *Finding Statistics Online How to Locate the Elusive Numbers You Need*. Medford, N.J.: Information Today; Everitt, (1998) *The Cambridge Dictionary of Statistics* New York: Cambridge University Press; Kotz (1988). *Encyclopedia of Statistical Sciences*, vol. 1-9 plus supplements New York: Wiley; Dillon and Goldstein (1984). *Multivariate Analysis: Methods and Applications* New York: Wiley; Tabachnick and Fidell (1996) *Using Multivariate Statistics* New York: HarperCollins College Publishers; Box et al. (1978) *Statistics for Experimenters* New York: Wiley; Cornell (1990) *Experiments with Mixtures* New York: Wiley; John, P. W. M. (1998) *Statistical Design and Analysis of Experiments* Philadelphia: SIAM; Gibas and Jambeck (2001) *Bioinformatics Computer Skills* O'Reilly, Sebastipol, Calif.; Pevzner (2000) *Computational Molecular Biology and Algorithmic Approach*, The MIT Press, Cambridge Mass.; Durbin et al. (1998) *Biological Sequence Analysis: Probabilistic Models of Proteins and Nucleic Acids*, Cambridge University Press, Cambridge, UK; and Rashidi and Buehler (2000) *Bioinformatic Basics: Applications in Biological Science and Medicine* CRC Press LLC, Boca Raton, Fla.

Calculating Diffusion and Dispersion

One feature of the invention is the discovery that the highly reproducible peak parameters, e.g., amplitude, width area, and/or shape features of a signal from an amplification reaction can be correlated to the starting copy number for the reaction and/or used to discriminate signals of interest from background fluctuations. This correlation can be performed at the theoretical level, taking thermal diffusivity and Taylor Aris diffusion into account, or it can be performed by comparison to standards (e.g., comparisons to peak shapes, e.g., heights, widths, or general shape profiles for amplification reactions that have known copy numbers for starting materials). The same or different peak parameters can be evaluated in interpretation of detector signals for two on more probes in determination of nucleic acid length.

For theoretical calculation approaches, a label is typically initially confined in a region $-h<x<h$, as a function of time (t) and spatial position (x) with respect to the peak center (x=0) and the concentration (C) of the label, or of a component corresponding to the label (e.g., the nucleic acid of interest), is equal to $\frac{1}{2}C_o \{erf[(h-x)/(2Dt)^{1/2})]\}$, where $C_o$ is the initial concentration at time t=0, erf is an error function, and D is a coefficient of overall dispersion. D is equal to the sum of thermal diffusion and Taylor dispersion ($D_T$) in the system. In turn, the Taylor dispersion ($D_T$) is dependent on the dimensions and shape of the microfluidic cavity through which the label is flowed, the flow velocity (u) and the thermal diffusivity (D). Typically, $D=K(d^2u^2)/D$, where K is a proportionality factor which is a function of the microfluidic cavity through which the label is flowed and d is a characteristic microfluidic cavity length. For example, where the microfluidic cavity is a circular channel and $K=\frac{1}{192}$, d is the diameter of the circular channel and $D=D+D_T$. Further details on thermal diffusivity and Taylor Aris dispersion can be found in MICROFLUIDIC SYSTEMS AND METHODS FOR DETERMINING MODULATOR KINETICS, U.S. Ser. No. 09/609,030 By Andrea Chow, Filed Jun. 30, 2000.

Additional System Details

The systems of the invention can include microfluidic devices, reaction mixtures, detectors, sample storage elements (microtiter plates, dried arrays of components, etc.), flow controllers, amplification devices or microfluidic modules, computers and/or the like. These systems can be used for aliquotting, amplifying and analyzing the nucleic acids of interest. The microfluidic devices, amplification components, detectors and storage elements of the systems have already been described in some detail above. The following discussion describes appropriate controllers and computers, though many configurations are available and one of skill would be expected to be familiar in their use and would understand how they can be applied to the present invention.

Flow Controllers

A variety of controlling instrumentation is optionally utilized in conjunction with the microfluidic devices described herein, for controlling the transport and direction of fluids and/or materials within the devices of the present invention, e.g., by pressure-based or electrokinetic control.

For example, in many cases, fluid transport and direction are controlled in whole or in part, using pressure based flow systems that incorporate external or internal pressure sources to drive fluid flow. Internal sources include microfabricated pumps, e.g., diaphragm pumps, thermal pumps, Lamb wave pumps and the like that have been described in the art. See, e.g., U.S. Pat. Nos. 5,271,724, 5,277,556, and 5,375,979 and Published PCT Application Nos. WO 94/05414 and WO 97/02357. The systems described herein can also utilize electrokinetic material direction and transport systems.

Preferably, external pressure sources are used, and applied to ports at channel termini. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or preferably, by applying a single vacuum at a common waste port and configuring the various channels with appropriate resistance to yield desired flow rates. Example systems are described in U.S. Ser. No. 09/238,467 filed Jan. 28, 1999.

Typically, the controller systems are appropriately configured to receive or interface with a microfluidic device or system element as described herein. For example, the controller and/or detector, optionally includes a stage upon which a microfluidic device is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

The controlling instrumentation discussed above is also optionally used to provide for electrokinetic injection or withdrawal of material downstream of the region of interest to control an upstream flow rate. The same instrumentation and techniques described above are also utilized to inject a fluid into a downstream port to function as a flow control element.

Computer

As noted above, either or both of the controller system and/or the detection system can be coupled to an appropriately programmed processor or computer (logic device) which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates (including for continuous flow), temperatures, applied voltages, and the like.

The systems and/or kits can include system instructions (e.g., embodied in a computer or in a computer readable medium, e.g., as system software) for practicing any of the method steps herein. For example, the system optionally includes system software that correlates a shape, length, width, volume and/or area occupied by amplified copies of the nucleic acid of interest, as detected by the detector, to the number of copies of the nucleic acid of interest present in one of the aliquots, or to the number of copies of the nucleic acid of interest present in the sample, or both. Similarly, the system optionally includes system instructions that direct the dilution module to aliquot the sample into a plurality of aliquots, including a plurality of zero copy aliquots comprising no copies of the nucleic acids of interest and one or more single copy aliquot comprising a single copy of the nucleic acid of interest.

The statistical functions noted above can also be incorporated into system software, e.g., embodied in the computer, in computer memory or on computer readable media. For example, the computer can include statistical or probabilistic system software that performs one or more statistical or probabilistic analysis of signals received from one or more of the aliquots subjected to amplification (e.g., via thermocycling). For example, the statistical or probabilistic analysis can include Poisson analysis, Monte Carlo analysis, application of a genetic algorithm, neural network training, Markov modeling, hidden Markov modeling, multidimensional scaling, PLS analysis, and/or PCA analysis. The statistical or probabilistic analysis software optionally quantitatively determines a concentration, proportion, or number of the nucleic acids of interest in the sample.

Computers and software of the systems receive and evaluate signal data from one or more analyses to provide quantitation and/or proportionality determinations for nucleic acids of interest. In a basic form, e.g., the amplitude or integrated area of a signal can be adjusted with a conversion factor for an output in desired units, such as, e.g., copies per nL, ng/µL, and the like. Alternately, one or more standard materials of known concentration can be analyzed to provide data for regression analyses wherein changes in detectable signals with changes in concentration are expressed as an equation (standard curve) from which unknown concentrations can be determined by insertion of one or more signal parameters into the equation. In a particular embodiment, quantitation of a nucleic acid of interest can be based on the number of amplification cycles required to obtain a signal of a certain intensity.

In the present invention, the computer typically includes software for the monitoring of materials in the channels. Additionally, the software is optionally used to control electrokinetic or pressure modulated injection or withdrawal of material. The injection or withdrawal is used to modulate the flow rate as described above, to mix components, and the like.

Example System

Figure 6:
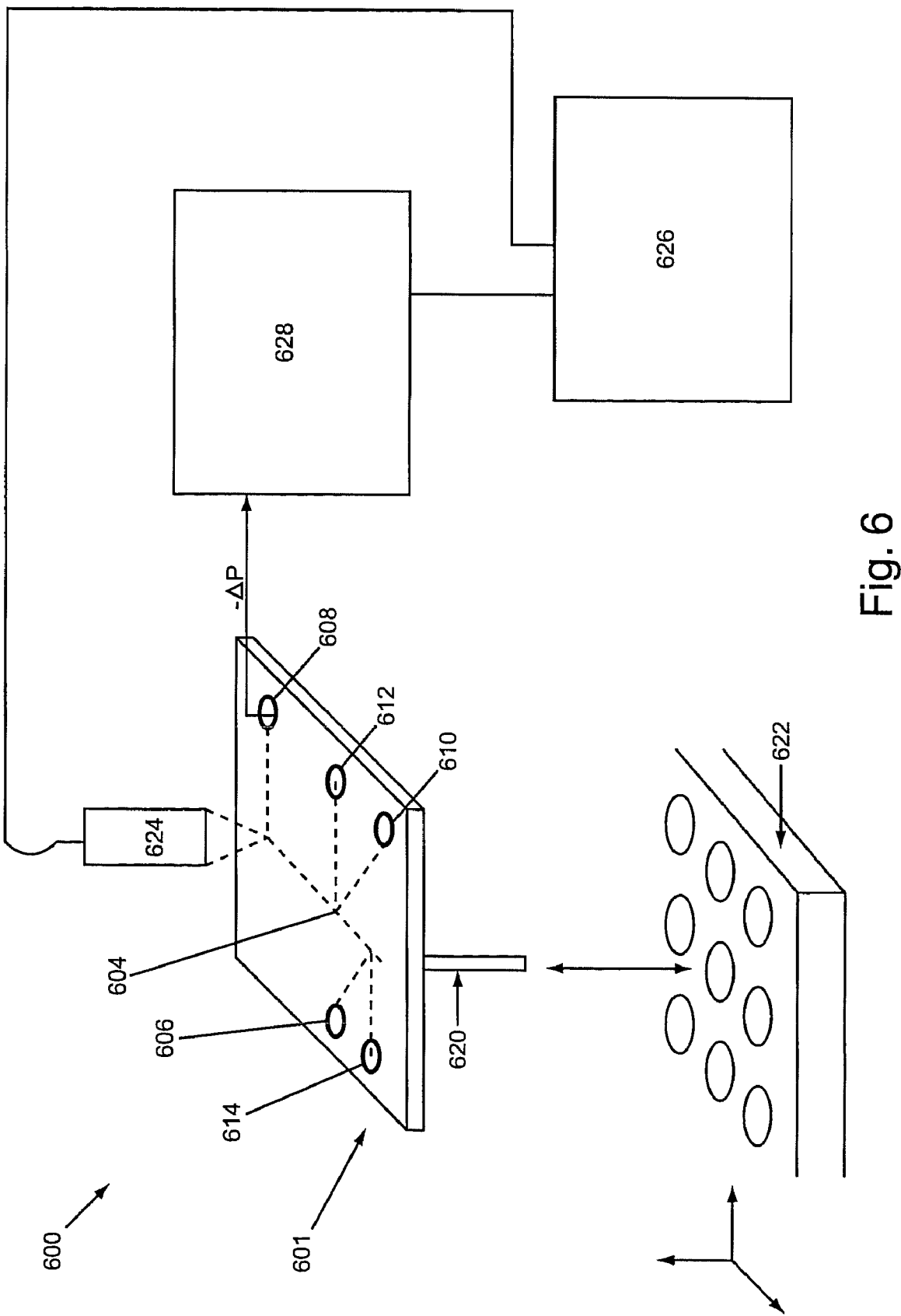
FIG. 6 is a schematic representation of a system of the invention.
Figure 7:
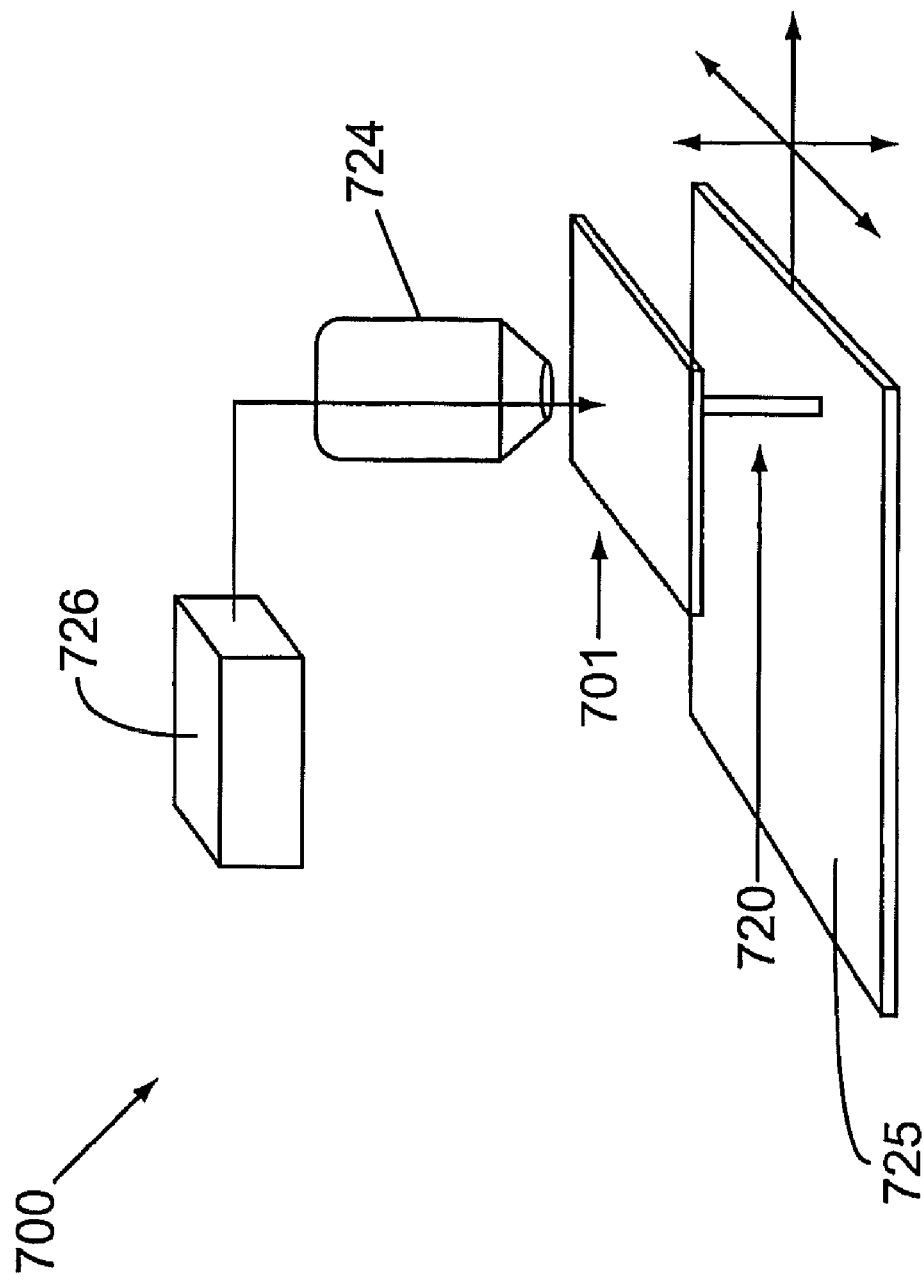
FIG. 7 is a schematic representation of a system of the invention.

FIGS. 6 and 7 provide a schematic illustration of a model system of the invention. As shown in FIG. 6, system 600 includes microfluidic device 601. Device 601 includes main channel 604 fabricated therein. Amplification components are flowed, e.g., from reservoir 606, e.g., by applying a vacuum at vacuum source 608 (and/or at any of the reservoirs or wells noted below) through main channel 604. Amplification components can also be flowed from wells 610 or 612 and into main channel 604, for example to form a reaction mixture. Materials can be also flowed from wells 606 or 608, or materials can be flowed into these wells, e.g., when they are used as waste wells, or when they are coupled to a vacuum source. Flow from wells 614, 612, 610, 606, or 608 can be performed by modulating fluid pressure, or by electrokinetic approaches. Instead of the arrangement of channels depicted in FIGS. 6 and 7, an arrangement such as the device of FIG. 1 can be substituted. A variety of other appropriate microfluidic configurations are set forth in the references noted herein.

Materials relevant to performing the amplification reactions can be flowed from the enumerated wells, or can be flowed from a source external to Device 601. As depicted, the integrated system can include pipettor channel 620 (sipper), e.g., protruding from device 601, for accessing an outside source of reagents. For example, as depicted, pipettor channel 620 can access microwell plate 622, which includes samples or sample aliquots, or locus specific reagents, or other reagents useful in the practice of the invention in the wells of the plate. Aliquots or reagents relevant to amplification can be flowed into channel 604 through pipettor channel 620. Detector 624 is in sensory communication with channel 604, detecting signals resulting, e.g., from the interaction of a label with an amplicon as described above. Detector 624 is operably linked to Computer 626, which digitizes, stores and manipulates signal information detected by detector 624.

Voltage/pressure controller 628 controls voltage, pressure, or both, e.g., at the wells of the system, or at vacuum couplings fluidly coupled to channel 604 (or the other channels, wells, or chambers noted above). Optionally, as depicted, computer 626 controls voltage/pressure controller 628. In one set of embodiments, computer 626 uses signal information to select further reaction parameters. For example, upon detecting amplification of a nucleic acid of interest in a well from plate 622, the computer optionally directs withdrawal of additional aliquots from the well for analysis through pipettor channel 620, e.g., to deliver different concentrations of the aliquot to the amplification reaction. Similarly, upon determining that no nucleic acid is present (a zero copy reaction) computer 626 can direct controller 628 to process another aliquot. If statistical information is desired, computer 626 directs controller 628 to perform appropriate fluid manipulations to generate enough data for the statistical analysis. Computer 626 is optionally coupled to or comprises a user viewable display, permitting control of the computer by the user and providing a readout for the user to view results detected by the system.

FIG. 7 depicts an alternate embodiment, in which a solid phase array of reagents or samples is accessed by a microfluidic system. As shown in FIG. 7, system 700 includes microfluidic device 701. Device 701 includes pipettor channel 720 and a microfluidic network fabricated within the device. Amplification components, such as primer pairs, polymerases, buffers, probes, etc., are flowed through device 701, typically by applying pressure (positive or negative) and/or electrokinetic pressure in the microfluidic network.

As depicted, the integrated system can include pipettor channel 720, e.g., protruding from device 701, for accessing an outside source of reagents. For example, as depicted, pipettor channel 720 can access solid phase array 725, which includes samples or sample aliquots, or locus specific reagents, or other reagents useful in the practice of the invention. Fluids are partly or completely expelled from channel 720 to rehydrate materials on array 725. For example, channel 720 can comprise a hanging drop that is used to rehydrate materials, with the drop being withdrawn into channel 720 for distribution into microfluidic device 701. Detector 724 is in sensory communication with device 701 and computer/controller 726. Computer/controller 726 can be operated in a manner similar to computer 626 of FIG. 6. In either case, computer 626 or computer controller 726 optionally control movement of tray 622 or array 725, and/or microfluidic device 601 or 701 to permit the relevant pipettor channel to process samples or other materials on the array or in the wells of the tray.

Many variations of the above system are also appropriate. For example, many types of heating systems can be used in the present invention. For example, winding the channel around fixed heating areas can be performed. Robotics or fluid system elements can be used to heat fluids in multiple different temperature water baths (e.g., 3 baths for a typical amplification reaction at typical annealing, reaction and dissociation conditions).

Additional Kits Details

The present invention also provides kits for carrying out the methods described herein. In particular, these kits typically include system components described herein, as well as additional components to facilitate the performance of the methods by an investigator.

The kit also typically includes a receptacle in which the system component is packaged. The elements of the kits of the present invention are typically packaged together in a single package or set of related packages. The package optionally includes reagents used in the assays herein, e.g., buffers, amplification reagents, sizing probe pairs, standard reagents, and the like, as well as written instructions for carrying out the assay in accordance with the methods described herein. In the case of prepackaged reagents, the kits optionally include pre-measured or pre-dosed reagents that are ready to incorporate into the methods without measurement, e.g., pre-measured fluid aliquots, or pre-weighed or pre-measured solid reagents that may be easily reconstituted by the end-user of the kit.

Generally, the microfluidic devices described herein are optionally packaged to include reagents for performing the device's preferred function. For example, the kits can include any of microfluidic devices described along with assay components, reagents, sample materials, control materials, or the like. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes/pumps, or the like (in one preferred embodiment, the device itself comprises a pipettor element, such as an electropipettor for introducing material into channels and chambers within the device). In the former case, such kits typically include a microfluidic device with necessary reagents predisposed in the channels/chambers of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like.

Examples

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims.

Single Molecule Amplification and Detection of DNA in a Microfluidic Format

Introduction

The amplification of a desired region of DNA by polymerase chain reaction (PCR) has revolutionized the field of molecular biology. In conventional formats of PCR, which use many microliters of fluids during amplification, the starting DNA copy number is typically at least hundreds to tens of thousands of molecules. Recent advances in microfluidics have demonstrated that it is feasible to miniaturize PCR down by a thousand fold to a nanoliter-reaction volume range. When the sample concentration remains constant, the starting number of DNA template in such a small volume can drop below a cutoff copy number that could be considered statistically unacceptable in some applications. For instance, in single nucleotide polymorphism (SNP) analysis, if the starting copy number is too low (below about a few tens of copies), the amplification of the two different alleles from a heterozygous sample may not amplify equally in quantity due to statistical fluctuations, possibly causing uncertainty in a correct SNP identification for that sample.

In the theoretical limit, only one DNA copy is necessary as a starting template for a PCR reaction. From such a reaction, the amplified product is a pure "clone" of a single parent DNA template, instead of a mixture of many DNA parent templates. Single molecule amplification and detection results in some interesting applications that are not achievable otherwise. One such application is the detection of cancer genes. This example describes (1) a method to perform single molecule PCR using microfluidic technology, (2) analysis and detection of single molecule amplification, and (3) example applications using single molecule PCR detection for cancer detection.

We have experimentally demonstrated that single molecule PCR is possible in a microfluidic channel. In experiments in the absence of flow, there is evidence in support of single molecule PCR in that localized "clouds" of fluorescent probes (corresponding to amplification products) were observed along the heated amplification microchannel (thus also representing a "detection region"). The evidence for single molecule PCR is more definitive in a sipper chip continuous flow format, in which a very large number of experiments can easily be conducted to obtain adequate statistics to support experimental observations.

Continuous Flow Protocol

Using a microfluidic sipper chip as shown in the chip design schematic of FIG. 1, a DNA sample (e.g., a genomic DNA) was brought onto chip 100 through a sipper using a pressure gradient into distribution channel 105. Under continuous flow, in an assembly-line fashion, the sample was first mixed with a common reagent from an on-chip reagent reservoir through common reagent channel 106, then split into 8 equal aliquots into 8 independent analysis channels 110-118. Each aliquot was mixed with locus-specific reagents supplied from a channel-specific chip reservoir to form a reaction mixture, then flowed through heated region 130 comprising metal traces proximal to amplification microchannel 110-118 to provide controlled heated regions of chip 100. Reagent addition for channel specific reagents into channels 110-118 provides an elegant microfluidic method of providing for an on-chip "hot start," in which all of the reagents are added to analysis channels just before amplification. The temperature of the region was cycled appropriately (temperature set points and respective dwell times are controlled) for PCR conditions in the channels in heated region 130. Heated channel lengths and fluid velocity are chosen such that the total PCR cycles meet a desired number, usually between 25 to 40 cycles (though inefficient PCR approaches that have short cycle times and high cycle numbers can also be used; See also, U.S. Pat. No. 6,303,343 to Kopf-Sill (Oct. 16, 2001) entitled INEFFICIENT FAST PCR). 8 channel detection region 135 comprises an appropriate detector for detecting PCR amplicons in channels 110-118.

Amplification and Detection of Rare Molecules

We used the PCR sipper chip illustrated in FIG. 1 to demonstrate single molecule PCR amplification, experimentally, in a continuous flow format. DNA samples with increasing dilution, in concentrations down to less than 1 molecule per nL, were prepared in a microtiter plate which supplies the samples to the sipper (on chip dilution could be performed in alternate embodiments). Due to statistical fluctuations in sampling very low concentration DNA down to below one molecule per channel, it is expected that some channels will show amplification signals and some will not. The fraction of tests at which amplification is observed is best described by Poisson statistics.

Figure 2:
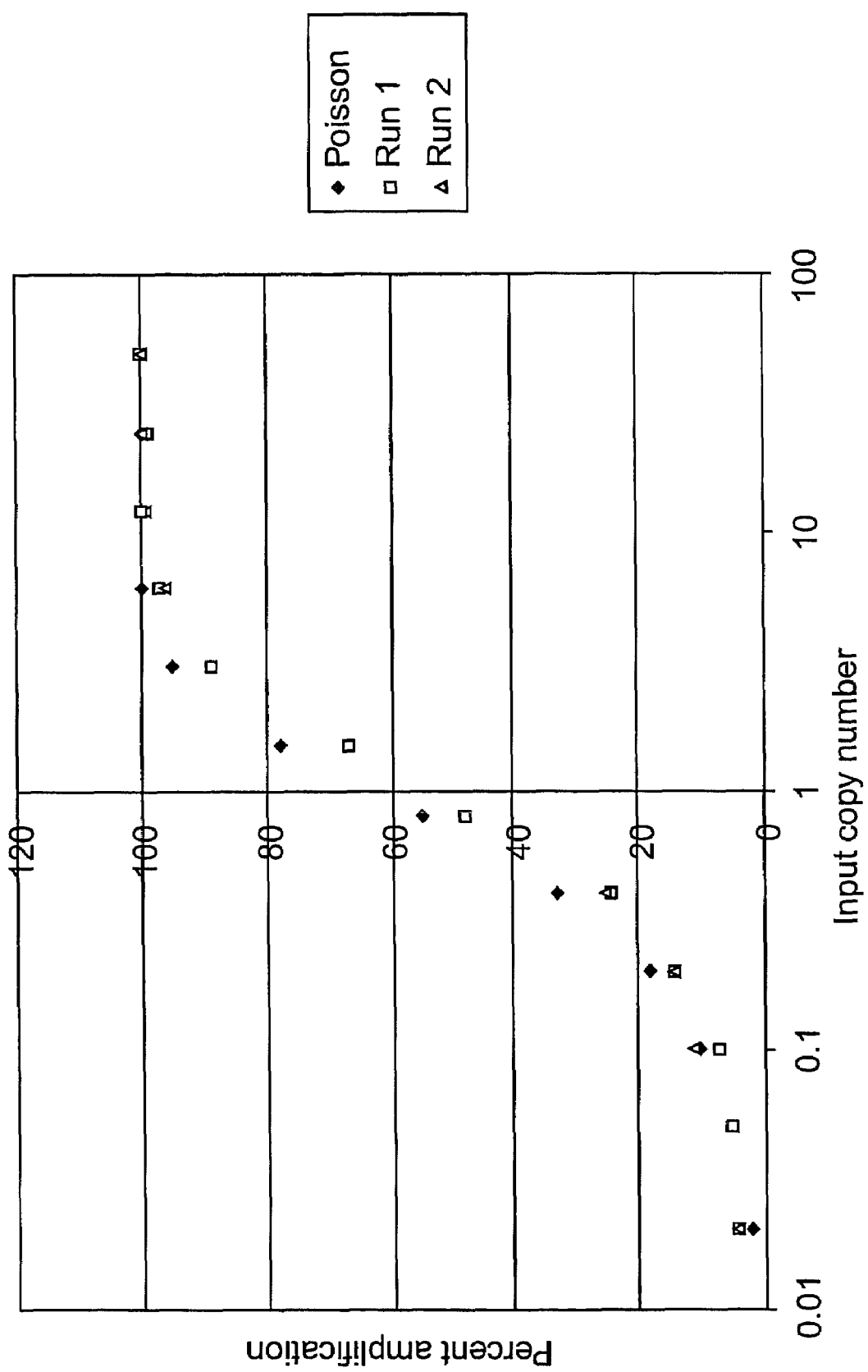
FIG. 2 is a graph of percent amplification versus input copy number for 2 experimental runs, with a comparison to a predicted (Poisson) value.

Table 1 summarizes results of a set of PCR experiments when the average copy number of DNA in each of the 8 channels varied from 0.02 to 48. For each DNA concentration, 8 PCR experiments were done simultaneously. The number of occurrences of a measurable PCR fluorescent signal for each sample was recorded in Table 1, with the maximum occurrence being 8 and the minimum being 0. The percent of occurrence of PCR was calculated and compared with a Poisson statistics prediction. A very good agreement between the measured and predicted percent occurrence of PCR was found. Table 2 summarizes a replication of similar sets of experiments on another day. FIG. 2 is a graphical comparison of predicted (Poisson) and measured statistics (Run 1 and 2) for both sets of experiments. Predicted and actual measurements show close agreement.

TABLE 1

| PLATE PASS | AVERAGE NUMBER OF COPIES IN THE CHANNEL | | | | | | | | | | | |
|---|---|---|---|---|---|---|---|---|---|---|---|---|
| | 0.02 | 0.05 | 0.1 | 0.2 | 0.4 | 0.8 | 1.5 | 3 | 6 | 12 | 24 | 48 |
| 1 | 0 | 0 | 0 | 2 | 2 | 3 | 5 | 6 | 6 | 8 | 8 | 8 |
| 2 | 0 | 0 | 3 | 0 | 0 | 5 | 7 | 8 | 8 | 8 | 8 | 8 |
| 3 | 0 | 0 | 1 | 1 | 2 | 2 | 5 | 7 | 8 | 8 | 8 | 8 |
| 4 | 2 | 0 | 0 | 1 | 3 | 2 | 5 | 7 | 8 | 8 | 8 | 8 |
| 5 | 0 | 0 | 2 | 0 | 1 | 4 | 3 | 7 | 8 | 8 | 8 | 8 |
| 6 | 1 | 0 | 2 | 2 | 3 | 5 | 5 | 7 | 7 | 8 | 8 | 8 |
| 7 | 2 | 1 | 0 | 0 | 3 | 3 | 5 | 7 | 8 | 8 | 8 | 8 |
| 8 | 0 | 3 | 1 | 4 | 1 | 2 | 6 | 7 | 8 | 8 | 7 | 8 |
| 9 | 1 | 2 | 0 | 3 | 1 | 5 | 8 | 7 | 7 | 8 | 8 | 8 |
| 10 | 0 | 1 | 0 | 1 | 2 | 5 | 7 | 8 | 8 | 8 | 8 | 8 |
| 11 | 0 | 0 | 0 | 1 | 4 | 4 | 5 | 7 | 8 | 8 | 8 | 8 |
| 12 | 0 | 0 | 0 | 0 | 3 | 8 | 7 | 8 | 8 | 8 | 8 | 8 |
| 13 | 0 | 0 | 0 | 1 | 3 | 3 | 5 | 7 | 8 | 8 | 8 | 8 |
| 14 | 0 | 0 | 1 | 1 | 2 | 3 | 6 | 6 | 8 | 8 | 8 | 8 |
| 15 | 0 | 0 | 0 | 0 | 2 | 6 | 6 | 8 | 8 | 8 | 8 | 8 |
| 16 | 0 | 0 | 0 | 0 | 1 | 5 | 3 | 8 | 8 | 8 | 8 | 8 |
| 17 | 0 | 0 | 0 | 0 | 0 | 2 | 5 | 6 | 8 | 8 | 8 | 8 |
| 18 | 0 | 1 | 0 | 2 | 2 | 4 | 4 | 7 | 8 | 8 | 8 | 8 |
| 19 | 0 | 0 | 0 | 2 | 1 | 2 | 5 | 8 | 8 | 8 | 8 | 8 |
| TOTAL | 6 | 8 | 10 | 21 | 36 | 73 | 102 | 136 | 148 | 152 | 151 | 152 |
| POSSIBLE | 152 | 152 | 152 | 152 | 152 | 152 | 152 | 152 | 152 | 152 | 152 | 152 |
| (actual/possible) % | 4% | 5% | 7% | 14% | 24% | 48% | 67% | 89% | 97% | 100% | 99% | 100% |
| POISSON PREDICT | 2% | 5% | 10% | 18% | 33% | 55% | 78% | 95% | 100% | 100% | 100% | 100% |

TABLE 2

| PLATE PASS | AVERAGE NUMBER OF COPIES IN THE CHANNEL | | | | | | | | | | | |
|---|---|---|---|---|---|---|---|---|---|---|---|---|
| | 0.02 | 0.05 | 0.1 | 0.2 | 0.4 | 0.8 | 1.5 | 3 | 6 | 12 | 24 | 48 |
| 1 | 0 | 0 | 1 | 1 | 5 | 4 | 5 | 7 | 8 | 8 | 8 | 8 |
| 2 | 1 | 1 | 0 | 2 | 2 | 3 | 5 | 6 | 7 | 8 | 8 | 8 |
| 3 | 0 | 0 | 2 | 2 | 2 | 3 | 2 | 8 | 8 | 8 | 8 | 8 |
| 4 | 1 | 0 | 0 | 0 | 3 | 3 | 5 | 5 | 8 | 8 | 8 | 8 |
| 5 | 0 | 0 | 1 | 1 | 1 | 2 | 5 | 8 | 8 | 8 | 8 | 8 |
| 6 | 0 | 0 | 0 | 2 | 2 | 3 | 4 | 8 | 7 | 8 | 8 | 8 |
| 7 | 0 | 0 | 0 | 2 | 1 | 4 | 5 | 7 | 8 | 8 | 8 | 8 |
| 8 | 0 | 1 | 2 | 0 | 0 | 3 | 5 | 6 | 8 | 8 | 8 | 8 |
| 9 | 0 | 0 | 0 | 2 | 1 | 2 | 3 | 6 | 8 | 8 | 8 | 8 |
| 10 | 1 | 0 | 0 | 0 | 3 | 1 | 4 | 6 | 7 | 8 | 8 | 8 |
| 11 | 0 | 0 | 1 | 0 | 4 | 5 | 5 | 6 | 8 | 8 | 8 | 8 |
| 12 | 0 | 0 | 0 | 2 | 3 | 2 | 3 | 7 | 7 | 7 | 8 | 8 |
| 13 | 3 | 1 | 4 | 0 | 1 | 1 | 4 | 6 | 7 | 8 | 8 | 8 |
| 14 | 0 | 1 | 2 | 1 | 1 | 4 | 7 | 6 | 7 | 8 | 8 | 8 |
| 15 | 0 | 0 | 2 | 1 | 0 | 5 | 4 | 8 | 8 | 8 | 8 | 8 |
| 16 | 0 | 0 | 0 | 1 | 1 | 4 | 3 | 7 | 8 | 8 | 8 | 8 |
| 17 | 0 | 0 | 0 | 2 | 3 | 4 | 4 | 4 | 8 | 8 | 8 | 8 |
| 18 | 0 | 0 | 1 | 0 | 4 | 0 | 6 | 7 | 8 | 8 | 8 | 8 |
| 19 | 0 | 1 | 0 | 1 | 1 | 3 | 2 | 8 | 8 | 8 | 8 | 8 |
| 20 | 1 | 0 | 1 | 3 | 2 | 2 | 4 | 7 | 8 | 8 | 8 | 8 |
| TOTAL | 7 | 5 | 17 | 23 | 40 | 58 | 85 | 133 | 154 | 159 | 160 | 160 |
| POSSIBLE | 160 | 160 | 160 | 160 | 160 | 160 | 160 | 160 | 160 | 160 | 160 | 160 |
| (actual/possible) % | 4% | 3% | 11% | 14% | 25% | 36% | 53% | 83% | 96% | 99% | 100% | 100% |
| POISSON PREDICT | 2% | 5% | 10% | 18% | 33% | 55% | 78% | 95% | 100% | 100% | 100% | 100% |

Figure 3A:
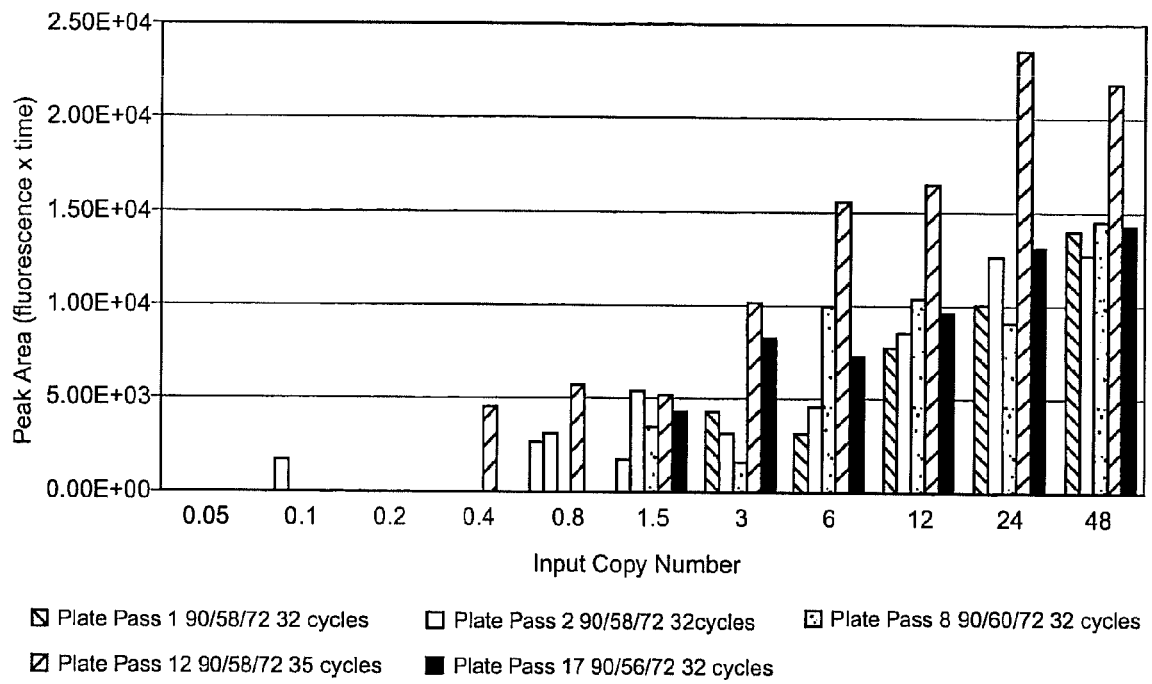
FIG. 3, Panels A and B provide peak area and peak width bar graphs.
Figure 3B:
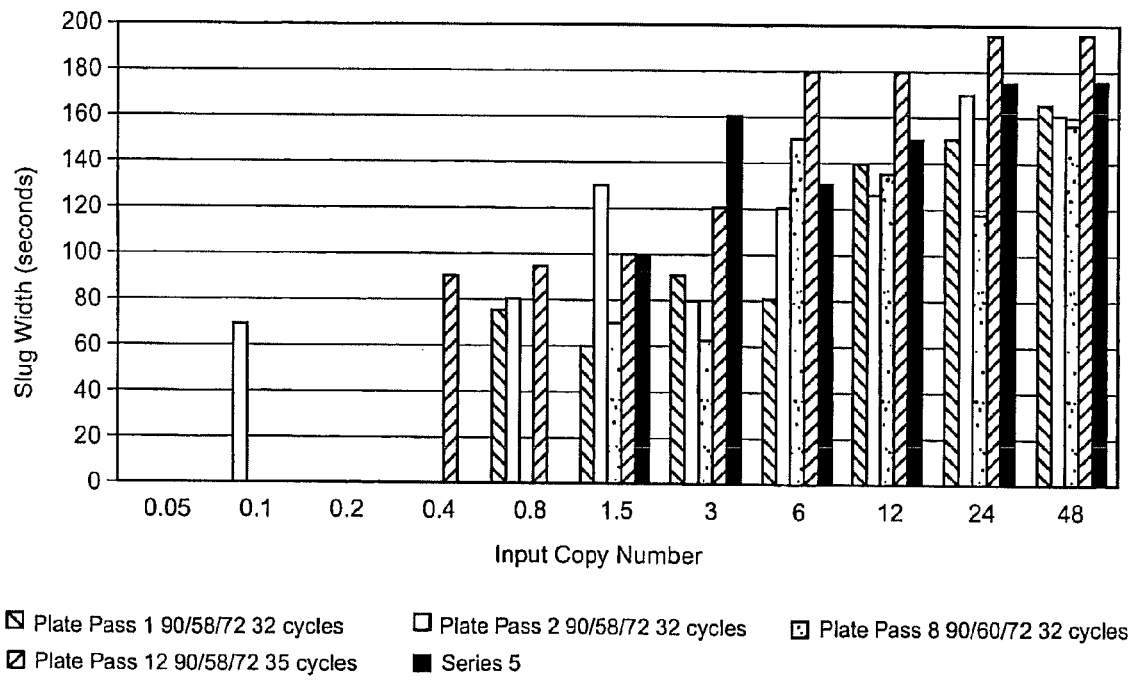
Figure 4A:
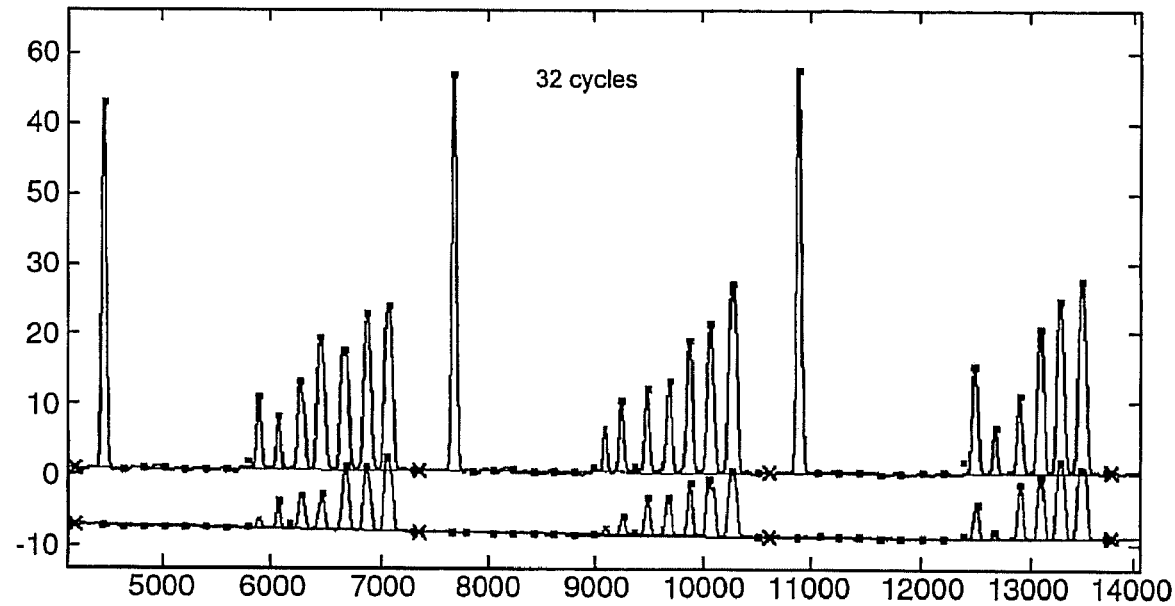
FIG. 4, Panels A-D are graphs illustrating peak width for amplification reactions.
Figure 4B:
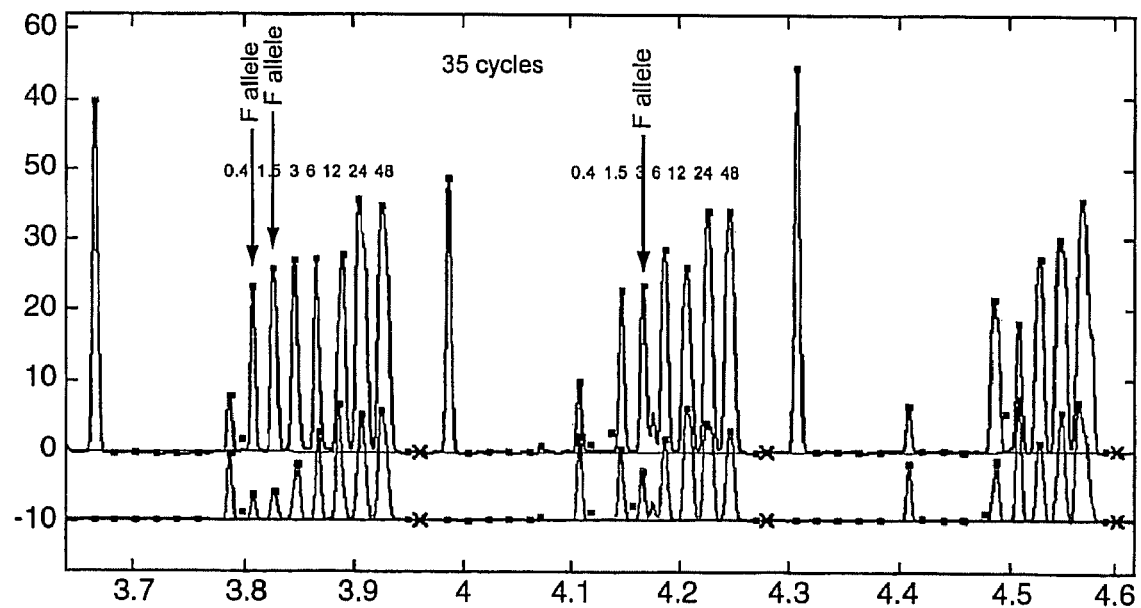
Figure 4C:
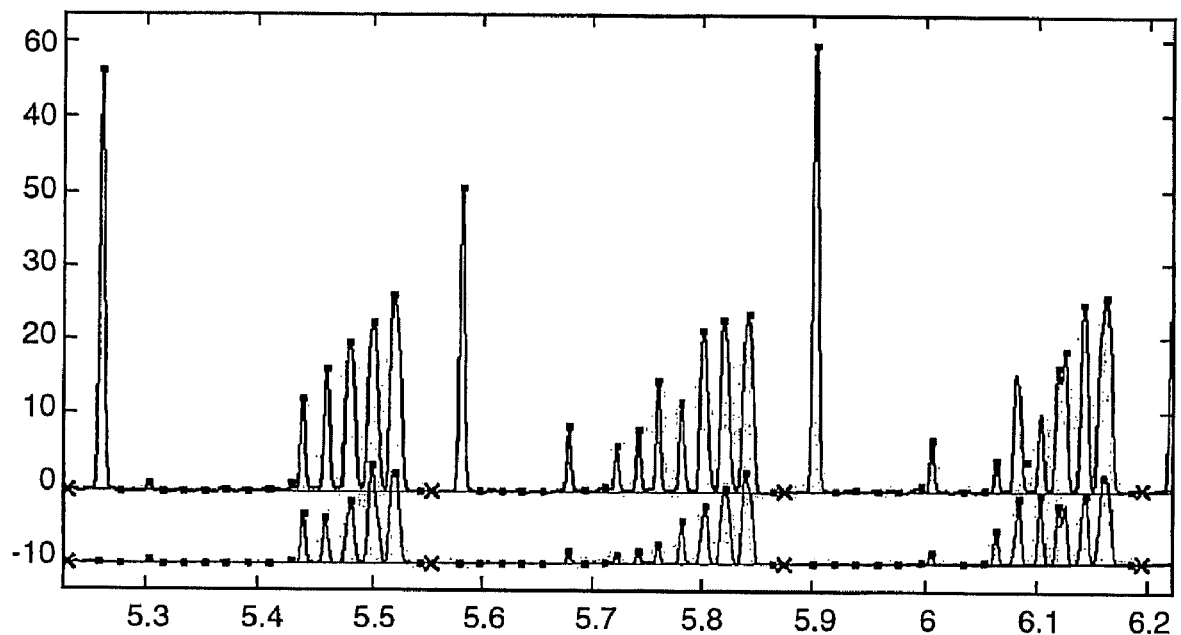
Figure 4D:
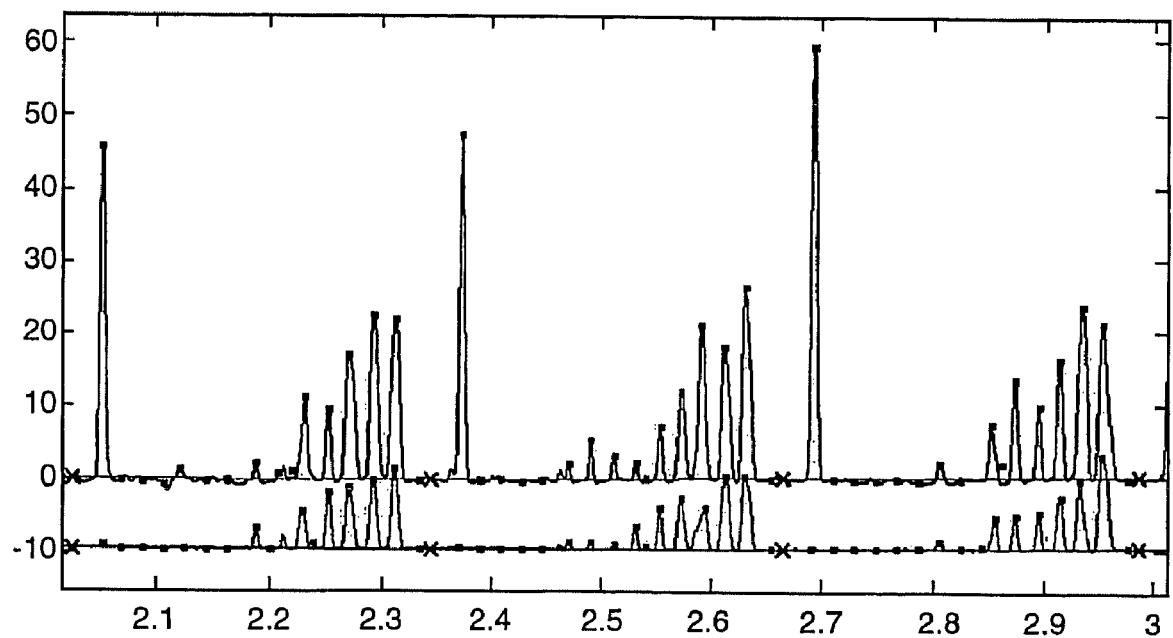

In a continuous flow mode, sipped samples broaden in plug length due to molecular diffusion and flow-induced dispersion. For a sipped sample containing tens or hundreds of copies of starting DNA templates, the effect of diffusion and dispersion on the width of the fluorescence PCR probe region can be predicted by considering Taylor-Aris dispersion. For single molecule PCR, similar calculations can be performed, and the peak shape of the fluorescent product is less broad than a large sample plug counterpart. The narrower peak is mainly due to the starting region from which DNA is amplified being narrower in the single molecule case (a few nm instead of hundreds of μm). FIGS. 3A and 3B summarize analysis of peak area and peak (slug) width as a function of starting copy number of DNA in channels. The lower copy number amplifications in fact showed narrow peaks as expected (and vice-versa).

Evidence for the system amplifying and typing single molecules also includes the fact that when the sample is a heterozygote, all peaks are positive for one or the other TaqMan probe, but not both.

There are other uses for single molecule typing that can be performed according to the present invention as well. For example, two TaqMan™ or molecular beacon assays can be developed for sequences that are located close together in the genome. Those assays can be used to determine whether the proximal sequences are present on the same amplified molecule. This is an indirect way of doing a sizing assay: one can ask whether individual molecules have both TaqMan™/beacon sites, providing an indication of how often molecules are of a size that encompasses both sites. One can also type the two sites, providing a haplotyping method.

Experiment to Monitor PCR Amplification On-Chip by Measuring Fluorescence Generated by TaqMan Probe Cleavage.

Figure 5:
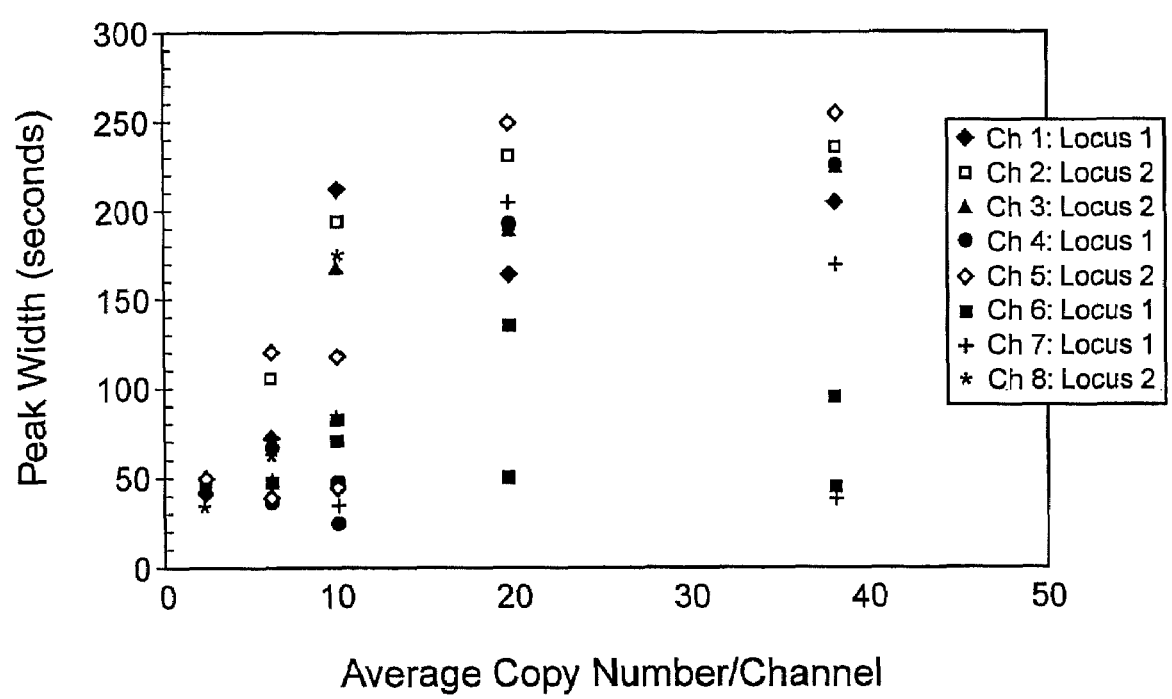
FIG. 5 is a graphical analysis of single molecule amplification peak widths.

This example provides an experiment to monitor PCR amplification on-chip by measuring fluorescence generated by TaqMan probe cleavage. FIG. 5 shows the peak width at ½ max vs. calculated input copy number per channel (on-chip).

For this experiment, all necessary PCR reagents were loaded on-chip. One DNA sample was diluted in assay buffer in a 384-well plate (0.72 ng/μL to 11.5 ng/μL). The amplification cycle time was 17 seconds (5 seconds at 90° C., 7 seconds at 58° C. and 5 seconds at 72° C.). All injected samples were subjected to a total of 35 amplification cycles. Samples were injected for a total of 200 seconds, with a buffer wash (between samples) of 350 seconds. Width of PCR signal (peak) was measured at ½ the peak maximum for each microfluidic channel on-chip (8 total). Data shows that amplification of a single molecule in any channel produces the same width, in time (approximately 40-50 seconds). As more molecules (copies) are injected onto the chip, they begin to overlap, causing the width of the peak to increase in time. However, with long injection times, some single molecules show up on the edges of the injected slug of DNA.

Application of Methods to Allele Typing

In cancer research, detection of cancer genes is very difficult because the mutated gene usually occurs at a much lower concentration then the wild type in a sample. The ability to detect amplification from a single molecule would solve the problem of detecting a low concentration of a mutated gene with a high concentration of wild type in the background since one can now study a single clone at a time. The use of the microfluidic sipper chip format with parallelized PCR on the chip speeds up the rate at which a single clone is examined at a time, to the point where it is practical to do a massive number of PCRs to find the few mutated genes responsible for cancer that exist in a given sample. FIG. 4 illustrates raw fluorescence intensity measurements for SNP analysis at very low starting copy number to below 1 copy per channel on average. These data show the possibility of detecting SNP at single molecule PCR conditions.

Figure 10:
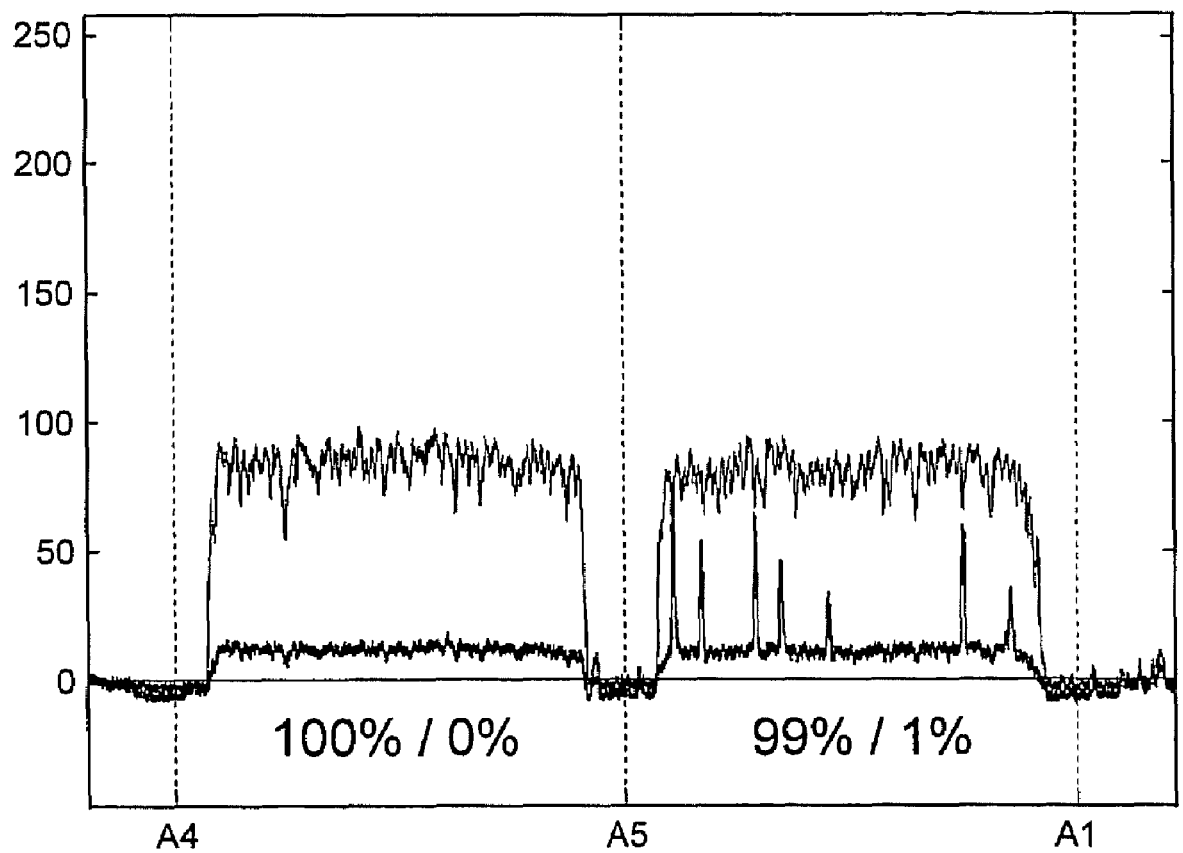
FIG. 10 is a data graph showing single molecule DNA amplification.
Figure 11:
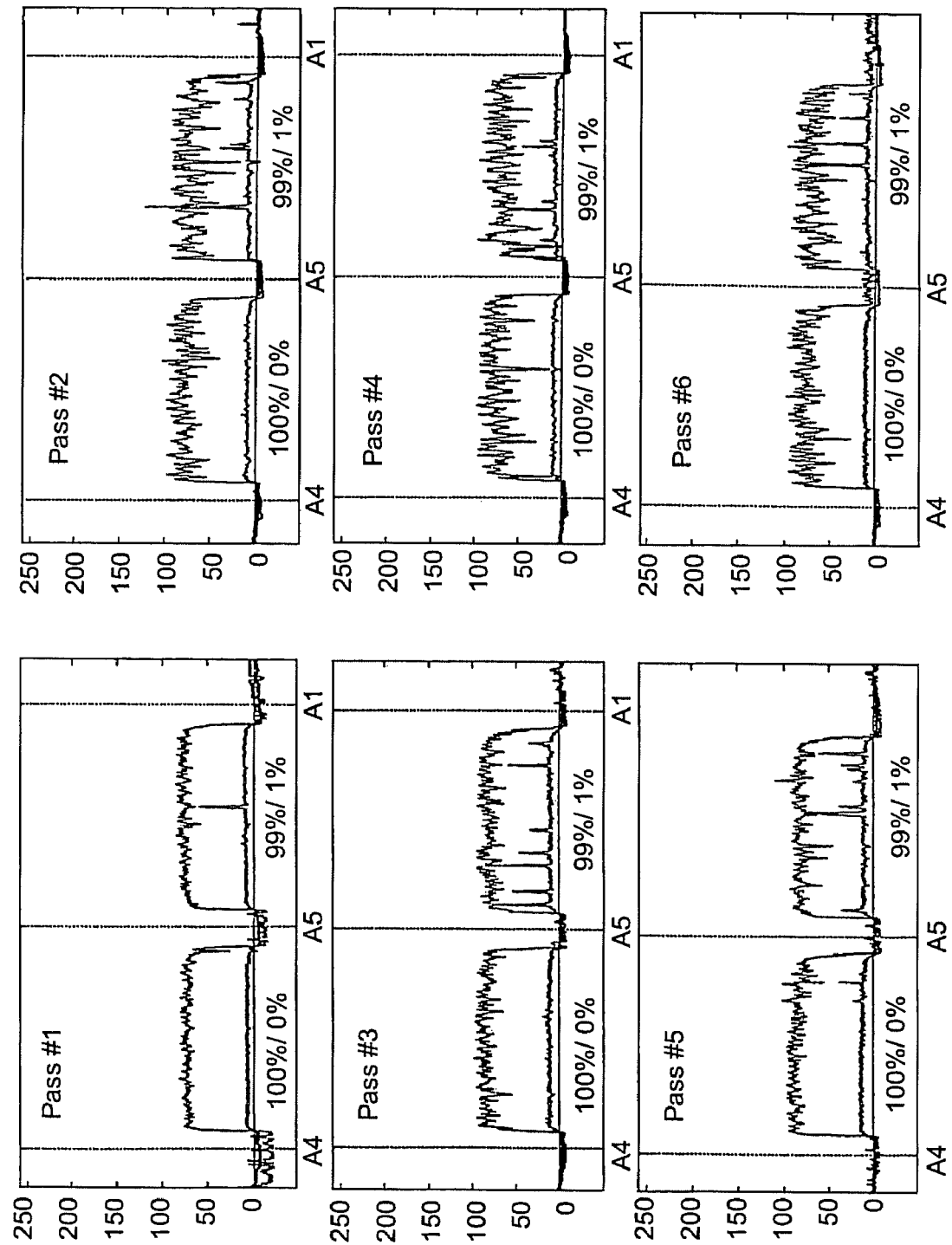
FIG. 11 is a data graph showing single molecule DNA amplification (6 passes).
Figure 12:
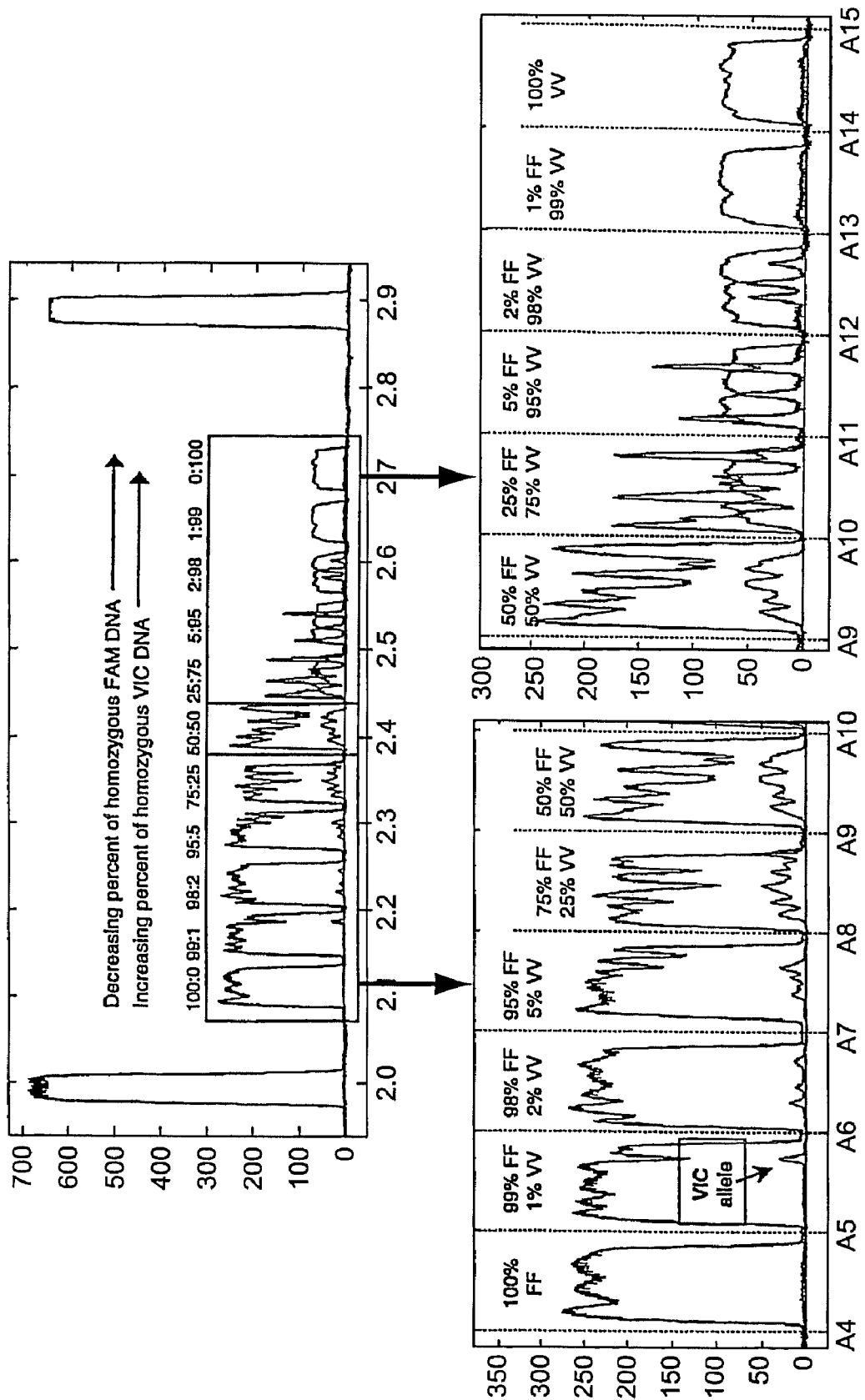
FIG. 12 is a data graph showing single molecule DNA amplification (3 panels).

FIGS. 10-12 show additional data from additional experimental runs, demonstrating single molecule amplification. As shown in FIGS. 10-11, a first set of experimental data with 100% of a first SNP allele is shown on the left, while a second set of experimental data with 1% of a second SNP allele (and 99% of the first allele) is shown on the right. The top signal line on the figure is data using a first dye detection system (which provides a longer wavelength "red" signal) for detecting amplification of the first allele, while the bottom line is data from a second dye detection system (a shorter wavelength "blue" signal) for detecting amplification of the second allele. The data represents about 700 total detected DNA molecules in one sample slug. As shown, only the right side shows signal peaks corresponding to amplification of the second SNP. The data prove that a system of the invention can accurately amplify and detect rare molecules within a large population. That is, as a model, two DNA samples were mixed, each homozygous for the two alleles of a SNP. In this experiment, single DNA molecules for one allele that were present in a large population of DNA molecules of the other allele were detected (5-7 low copy alleles in about 700 for this case). FIG. 11 provides results for 6 separate experimental runs, demonstrating that characteristic peak shapes from molecule to molecule is constant, providing experimental evidence that both PCR and dispersion of the resulting amplicons are very reproducible. In fact, a LabChip®-based system, as in the present invention, allows unlimited sensitivity to rare molecules in that: 1) it is practical, in a microfluidic system, to spread the sample out through the channel such that rare molecules are present amongst smaller numbers of wild-type molecules (reducing the problems created by proportional amplification of starting materials in each aliquot); and 2) reproducible fluidic handling and analysis gives a predictable single molecule peak shape that can be used to discriminate between molecular signals and random signal fluctuations.

FIG. 12 provides a titration of a first SNP against a second SNP, showing that the signal from the amplicons corresponding to the first SNP ("FAM DNA," in the upper trace) and the second SNP ("VIC DNA," lower trace) show an appropriate signal correlation. The given percentages correspond to the percentage of DNA from a first homozygous sample (both alleles in the first homozygous sample are "FAM", that is, the material from the homozygous sample is "FF" homozygous) and a second homozygous sample (both alleles in the are VIC DNA sample, "VV"). In this context, "FAM DNA" stands for a DNA sequence that is probed for by a specific oligo sequence with a FAM dye label, while "VIC DNA" stands for a DNA sequence that is probed for by a specific oligo sequence with a VIC dye label. "FF" stands for a homozygous DNA sample for the "FAM" (oligo) sequence and "VV" stands for a homozygous DNA sample for the "VIC" (oligo) sequence.

Demonstration of Detection of Cancer Markers

Figure 13:
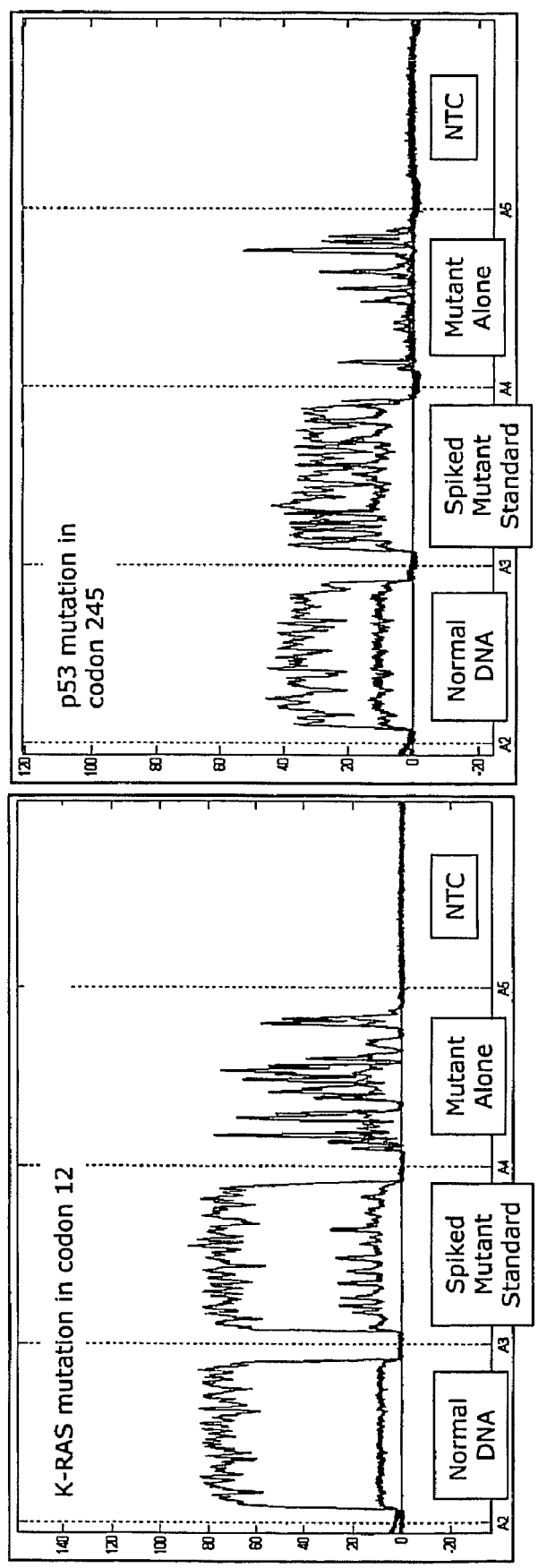
FIG. 13 provides a graph of detection of 2 mutation sites relevant to cancer detection developed on-chip using TaqMan probes.

FIG. 13 provides an example of detection of 2 mutation sites relevant to cancer detection developed on-chip, using TaqMan probes. To demonstrate the relevance of the system of the invention to cancer diagnostics, it was used to test a number of cancer (e.g., colorectal cancer) markers using TaqMan probes. Two of those assays are shown in FIG. 13: one for the K-RAS gene and one for the p53 gene, both diagnostic markers for a variety of cancers, such as colon cancer. The data trace shows fluorescence at two wavelengths vs. time for one microfluidic channel. Two TaqMan probes, one specific for the normal allele, and one specific for the mutant allele, were designed and tested in this on-chip assay format. The presence of normal DNA is detected with the wild-type probe (a "red" signal, designated in the black and white reproduction on the top data trace) and mutant DNA molecules are detected with the mutant probe (a "blue" signal, represented in the black and white reproduction as the bottom data trace). Most of the DNA molecules (approximately 500) in the sample slug are normal, shown by the high "red" top fluorescent signal and low "blue" bottom fluorescent signal. This signal is produced by the allele-specific (red, top) and background (blue, bottom) TaqMan probe cleavage surrounding the amplification products of normal genomic DNA molecules. When a mutant molecule (synthetic DNA template with the appropriate point mutation) traverses the system, it is amplified and recognized as a large blue (bottom) peak (with red (top) background peaks).

A Device and Method of Single Molecule Amplification by Microfluidics that Permits Accurate Analysis of Heterogeneous Nucleic Acid Mixtures.

Continuous flow PCR systems allow for spatial separation of individual low, single copy, and zero copy amplification reaction mixtures in a microfluidic processing environment. Normally, spatial separation is used to separate different reactions, where the starting template concentration is high enough to ensure accurate representation of alleles coming from both parents (e.g., about 50 genome equivalents are often used). In the present invention, the same task is accomplished by diluting the DNA enough such that individual template molecules are separated such that the amplification and detection products for each one are fluidically separated. If the detection product is allele specific, a signal for only one of the two alleles is detected. One can the count the results for each allele, giving the genotype quite accurately. The disadvantage for genotyping by this method is that the throughput decreases: one needs many reactions to get a genotype, instead of just one. Genotyping is typically performed with one reaction because the starting concentrations in a two allele system is usually about 50/50 (or at least on the same order of magnitude) and the signal-to-noise ratio of the genotyping biochemistry is good.

If, however, the representation of different alleles in the starting sample differs enormously, the genotyping biochemistry is not good enough to give an accurate quantitation of the under-represented allele. In fact, as a practical matter, it is very difficult to use many typical detection biochemistries for detection of alleles that are present in as few as 1 in 5 copies. In cancer, the mutant/normal ratio can be quite low (1 in thousands) and therefore undetectable by conventional biochemical methods. On the other hand, if one amplifies single molecules, the reactions can be repeated and flowed in a continuous system for as long as desired—and there is no theoretical limit of detection (just a practical one: if the mutant genotype is very rare, many reactions will have to be detected, e.g., in the continuous flow high throughput format).

This also provides a strategy for quantifying infectious agents by PCR. Today, that is done by PCR or RT-PCR which depends on a cycle-by-cycle quantification and comparison to a standard curve of template molecules amplified under similar conditions. In the present invention, we flowed the sample at a known flow rate and measured the amplifications per unit volume as a more precise and quantitative determination of the template concentration. One can accomplish the same thing by amplifying dilute concentrations of the sample in wells. When the total number of positive wells equaled $e^0=0.37$, there was a high statistical probability that each well had only a single template molecule in it. One could also have more than one molecule present in the flow stream at any given time if an independent and reliable way of measuring the copy number is used.

Single Molecule PCR in a Microfluidic Device Under Stop-Flow Conditions for Virus Detection & Analysis.

The desired sensitivity for virus detection (e.g., about 50-100 copies/ml) make it a challenging application for detection using a microfluidic platform, due to the mismatch between processing volume on the chip and the initial sample volume. However, one of the features of PCR in a microfluidic device demonstrated in this application is the ability to quantitate single copies of nucleic acids. This allows one to count the number of infected cells, or virus particles in a sample of interest, at biologically relevant concentrations of cells or virus particles. In this example, we describe quantitative single molecule PCR from a starting volume on the order of 10 microliters (an initial pre-concentration step taking the sample from ~1 ml to about 10 ul can be performed by standard techniques, e.g. immunoprecipitation or hybridization capture into magnetic beads).

The ~10 ul of concentrated solution containing e.g., >50 virus particles can be completely processed (or a substantial fraction of the volume processed) on a microfluidic chip in the following manner. The sample is mixed on-chip with the reagents necessary for PCR (at, e.g., a 1:1 ratio), e.g. primers, probes, dNTPs, etc. The mixture is pressure loaded into a microfluidic network that has a holdup volume on the order of 10 ul (see, FIG. 8), and the flow is stopped. As shown, the schematic device of FIG. 8 comprises PCR reagent well 801, sample well 802 vacuum/waste well 803, imaging area 804 (a detection region) and microfluidic network 805. The contents of the network are then thermocycled by applying heat externally to the chip, or, optionally, via resistive or Joule heating. Upon completion of thermocycling, the chip is imaged to locate all of the "clouds" of fluorescence (see, FIG. 9), each corresponding, typically, to a single copy of DNA from a virus particle.

Figure 8:
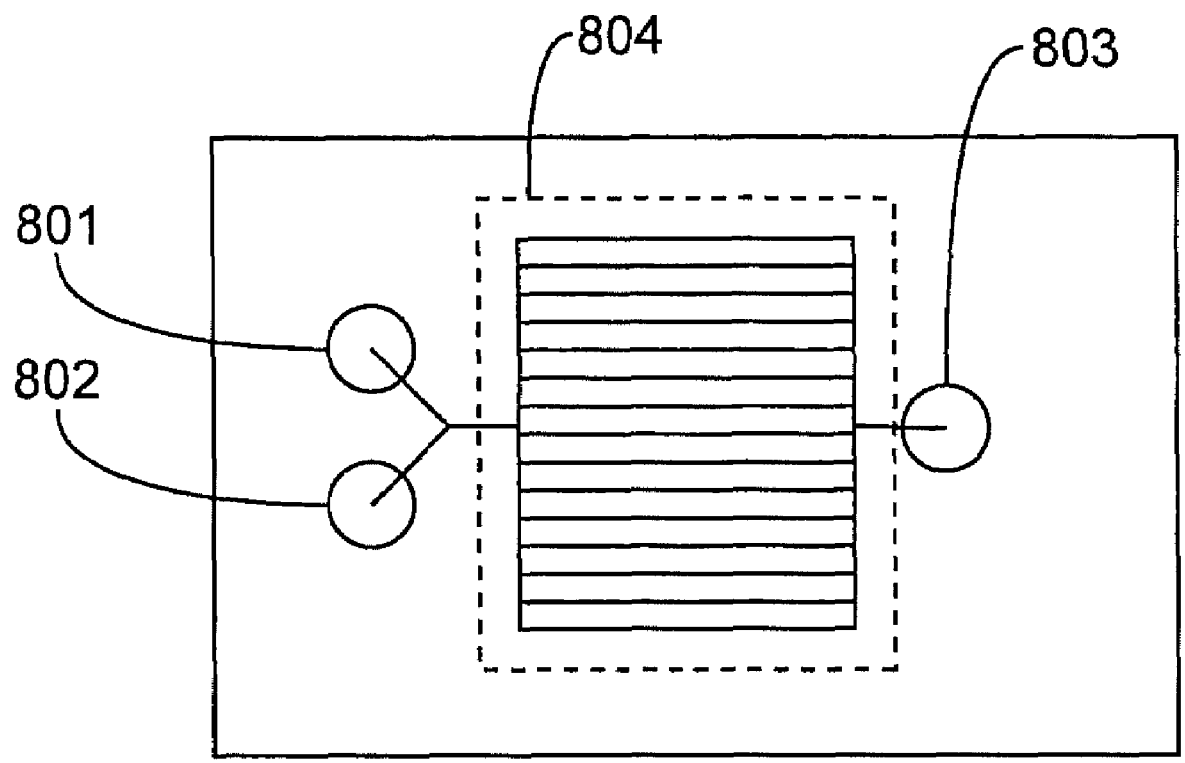
FIG. 8 is a schematic representation of a stopped flow system that uses simultaneous image processing of a network of channels to scan for nucleic acids of interest.
Figure 9:
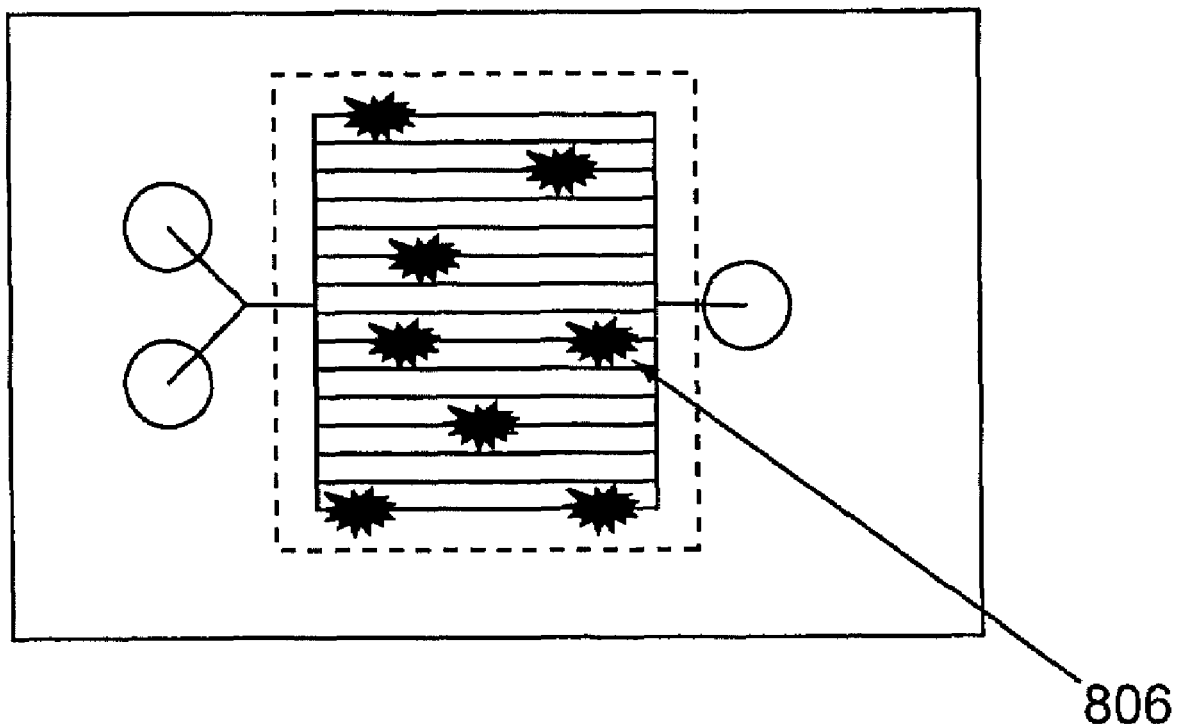
FIG. 9 is a schematic of a fluidic network after thermocycling. Spots represent the fluorescence "clouds" from single copy amplification reactions. The spots are counted for quantitative PCR analysis.

FIG. 9 is a schematic of the fluidic network of FIG. 8 after thermocycling. Spots 806 represent the fluorescence "clouds" from single amplicons (e.g., in one example, virus particle amplicons). Spots 806 can be counted for quantitative PCR. For this particular application, it is likely that it is most efficient to image the entire fluidic network of the chip simultaneously (e.g., CCD imaging), rather than in a continuous flow mode with the detector (e.g., a photodiode) at a fixed point. However, continuous flow can, alternatively, be used. The active area of the chip for imaging is typically on the order of 20×30 mm (but can, optionally, be smaller or larger). This area is compatible with high resolution imaging (~1-2 um resolution) via techniques commonly used for DNA array applications. These can include CCD imaging, confocal laser scanning, and/or the like.

The dynamic range for quantification is typically at least 2-3 orders of magnitude, depending, in part, on the size of the chip. For a typical size of 20×30 mm, the dynamic range is about 2 orders of magnitude. One way to estimate the dynamic range is to examine the average separation between copies, and then compute the expected diffusion distances over the course of an experiment. A rough calculation to demonstrate that these types of volumes can be processed on a microfluidic chip is presented below.

To determine whether further concentration of a 10 uL sample down to the nL range was necessary, the following calculation was performed. The conclusion reached was that further concentration was not necessary.

If one loads a series of parallel channels (e.g., 64) that are 30 um deep, 120 um wide, and 30 mm long, the total volume in these channels is 6.2 µL. If it is further assumed that in the 6.2 µL, half of the volume comes from PCR reagents and the other half comes from the original 10 µL sample, then roughly 3 µL out of 10 µL are sampled per run, which is a reasonable volume from a statistical sampling or a practical ease of use standpoint. Furthermore, if the 10 µL concentrated sample contains 100 particles from an initial starting 1 mL volume of plasma, then one can detect about 30 PCR clouds per run, if the PCR efficiency is close to 100%. These clouds would be 62 mm apart, on average, from each other along the channel, or about 1 cloud in every 2 channels.

The next issue addressed is chip size and detection practicality. If the 64 (2^n binary split) parallel channels are packed together with 200 um landing area between, they will occupy 21 mm. So an area of 30 mm×21 mm can be imaged (or scanned) to find the 30 PCR clouds (in stop flow mode) that should appear in the channels. This is similar to the size of a typical DNA assay chip, meaning that available chip scanners can be used for the detection.

In summary, if 1 mL is concentrated to 10 µL and placed into a chip well, further concentration is unnecessary for detection. If anything is done to increase the volume (such as the addition of neutralization chemical(s) to an elution buffer, addition of lysing agents, etc.), a further concentration step can be desirable. To avoid adding lysing agents, it can be desirable to do an ultrasonic lysing of particles in the 10 µL solution in the well before aliquotting.

The following is one example protocol for quantitative analysis by the above methods: 1) Off chip concentration, e.g., by affinity capture (a standard technique) and elution to reduce the sample from 1 mL to 10 µL; 2) Place the 10 µL concentrate in chip well, apply ultrasonic power to lyse particles; 3) Load the DNA sample into parallel channels with on chip addition of PCR reagents by pressure, then stop flow; 4) Activate external heater to perform PCR in stop flow mode for all channels; and, 5) Image or scan the channel to detect signs of single molecule PCR.

One aspect of the invention provides methods to ensure stopped flow conditions on a chip. There are a number of methods that can be employed. For example, one can use temperature sensitive materials (e.g. polymers), to create the stop-flow condition. A simple method to achieve stopped flow is to use standard chip-capillary or chip-tubing connections combined with a valve.

Methods and Devices for Determining Whether Nucleic Acids of Interest are of a Given Length Single molecule amplification techniques of the invention can be used to unambiguously determine whether a nucleotide of interest in a reaction mixture is, e.g., fragmented or has a given length between probes. For example, simultaneous signals from two or more different probes hybridized to opposite ends of a nucleic acid of interest in a single copy reaction mixture can provide a high level of confidence that the nucleic acid is not fragmented. This contrasts with conventional methods, such as dot blot hybridizations to multiple target nucleic acid copies, wherein coincidental detection of probes to each end of the nucleic acid of interest can indicate the presence of full length nucleic acid of interest and/or the presence of a one or more pair of unassociated fragmented nucleic acids of interest.

The methods and systems for determining length can detect the presence of individual full length or fragmented nucleic acids of interest, as well as provide counts indicating proportions or concentrations of fragmented nucleic acids of interest, even in complex mixtures containing large amounts of additional nucleic acids. Such counts can be subjected to statistical analyses for reporting of validated assay results and correlation to associated disease states.

Methods of Determining the Fragmentation Status of Nucleic Acids

Samples containing nucleic acids of interest can be diluted and/or contained in volumes small enough to provide reaction volumes that include on the average about 1 individual nucleic acid of interest (single copy) in a reaction mixture. If the single copy nucleic acid of interest is hybridized with two probes complementary to separated sequences on the nucleic acid of interest single copy, detection of the two hybridized probes at the same time in the reaction mixture indicates the nucleic acid is not fragmented between the separate probe target sequences. On the other hand, if the nucleic acid is fragmented between the target sequences, the single copy reaction mixture will contain only one of the fragments and only one of the hybridized probes would be detected. By diluting and/or subdividing the sample into such single copy reaction mixtures, one can confidently determine whether one or more nucleic acids of interest include at least a length (a given length) including the sequences complementary to particular probes and the nucleic acid between the probes.

Methods of determining whether a nucleic acid is of a given length can generally include, e.g., adjusting the concentration of a sample containing the nucleic acid; contacting the nucleic acid with probes, primer pairs, and a polymerase in a reaction mixture; amplifying the nucleic acid to produce specifically detectable amplicons; hybridizing probes to the nucleic acid and/or amplicons in the reaction mixture; flowing reaction mixture constituents into a detection region; detecting signals from hybridized probes; and, interpreting the signals to provide fragment and given length nucleic acid quantities or proportions. Such quantities or proportions can be correlated to disease states that may be associated with the sample source.

The concentration of nucleic acids of interest can be adjusted to provide useful numbers of low copy, single copy, and/or zero copy reaction mixtures in the methods of determining whether the nucleic acids are of a given length. Samples can be concentrated, e.g., by ultrafiltration, affinity capture, or immunoprecipitation so that a suitable copy number is obtained in reaction mixtures and detectors of the invention. Samples can be diluted, e.g., by serial dilution in microwell plates or admixing with buffers or reagents in a fluidic system dilution channel, to obtain a desirable concentration of nucleic acids. In many microfluidic embodiments, a concentration of about one nucleic acid of interest molecule per nanoliter is desirable for reaction or detection. In methods of the invention, the nucleic acid of interest can be adjusted to a range from about 100 molecules per nL to about 0.01 molecules per nL in the reaction mixtures, or from about 10 molecules per nL to about 0.1 molecules per nL, or from about 3 molecules per nL to about 1 molecule per nL.

It is generally useful in the methods of determining a given length to amplify the nucleic acid of interest to a larger number of probe target molecules for enhanced sensitivity. One can envision detecting unamplified individual nucleic acids of interest by using probes with highly specific or highly intense detectable marker signals (e.g., amplified or sandwich probes). However, in a preferred embodiment, the nucleic acids of interest are amplified in a reaction mixture containing a polymerizing enzyme that can make copies (amplicons) of sequences (and/or complements) from nucleic acids of interest. In a more preferred embodiment, the nucleic acid(s) of interest are amplified by contacting with two or more primer pairs and a polymerase enzyme in a polymerase chain reaction (PCR).

Typically, the PCR amplification reaction takes place in an amplification microchannel or microchamber of a microfluidic device. This can provide high throughput, low sample use, and isolation of single copy reaction mixtures. For example, reaction mixture constituents including a temperature stable DNA polymerase and one or more primer pairs can flow into a temperature controlled amplification microchannel with the nucleic acid of interest. Amplicons can be extended by polymerization from primer pairs hybridized to the nucleic acid of interest at specific locations, thus the primers define the amplicons. As is well known in the art of PCR, and previously discussed above, repeated cycles of nucleic acid melting, annealing to primers, and primer extension by the polymerase can increase by many orders of magnitude the amount of nucleic acid having the sequence (and second strand complement) defined by the primer pairs. In the methods of determining a given nucleic acid length, two or more primer pairs are typically provided in the reaction mixture to amplify two or more regions of the nucleic acid of interest associated with the intended probes. Regions of the amplified nucleic acid can include sequences complementary to the probes and spaced a given (known or unknown) sequence length apart. In some embodiments, the probes themselves can be members of the primer pairs defining the amplicons.

The nucleic acid of interest (and/or any amplicons) can be contacted with two or more different probes to determine whether the nucleic acid of interest includes the given length between sequences complementary to the probes. Where the nucleic acids of interest are single stranded, two probes can hybridize to complementary sequences spaced by the given length along the strand. Where the nucleic acids of interest are double stranded, and/or have had a complementary strand that was polymerized, e.g., in an amplification reaction, the probes can be complementary to and hybridize to sequences on either strand or both strands separated at a distance of the given sequence length.

Figure 14:
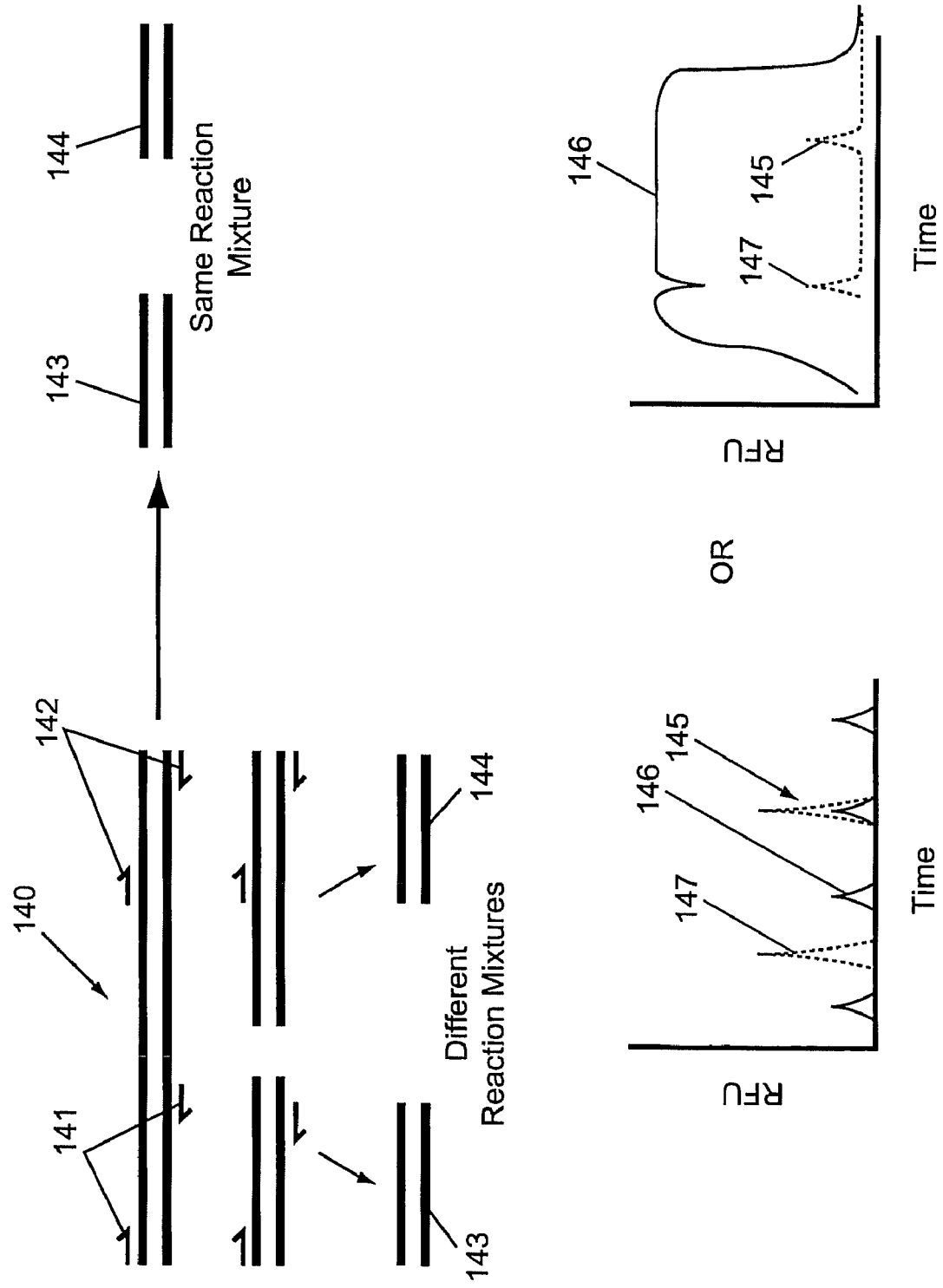
FIG. 14 shows a schematic diagram of low to single copy detection of nucleic acids of interest amplified using two amplicon sequences that do not overlap.

In an embodiment of the methods, the amplicons defined by two or more primer pairs do not overlap and are separated by sequences of about the given length, as shown in FIG. 14. If the nucleic acid of interest 140 is not fragmented between the first amplicon sequences defined by first primer pair 141 and the second amplicon sequences defined by second primer pair 142, low or single copy amplification reactions will include both first 143 and second 144 amplicons. Hybridization of such a reaction mixture with a first and second probe, specific to the first and second amplicon sequences, respectively, will provide coincident probe signals 145. If the nucleic acid of interest 140 is fragmented between the first amplicon sequences defined by first primer pair 141 and the second amplicon sequences defined by second primer pair 142, single copy amplification reactions will include either first 143 or second 144 amplicons, but not both. Hybridization of these single copy reaction mixtures with the first and second probes, specific to the first and second amplicon sequences, respectively, either first probe signals 146, or second probe signals 147 will be detected, but not both. Primer pairs in such amplifications typically define amplicon sequences of about 100 base pairs, with the amplicons ranging from more than about 5000 base pairs to about 20 base pairs, or from about 50 base pairs to about 1000 base pairs.

Figure 15:
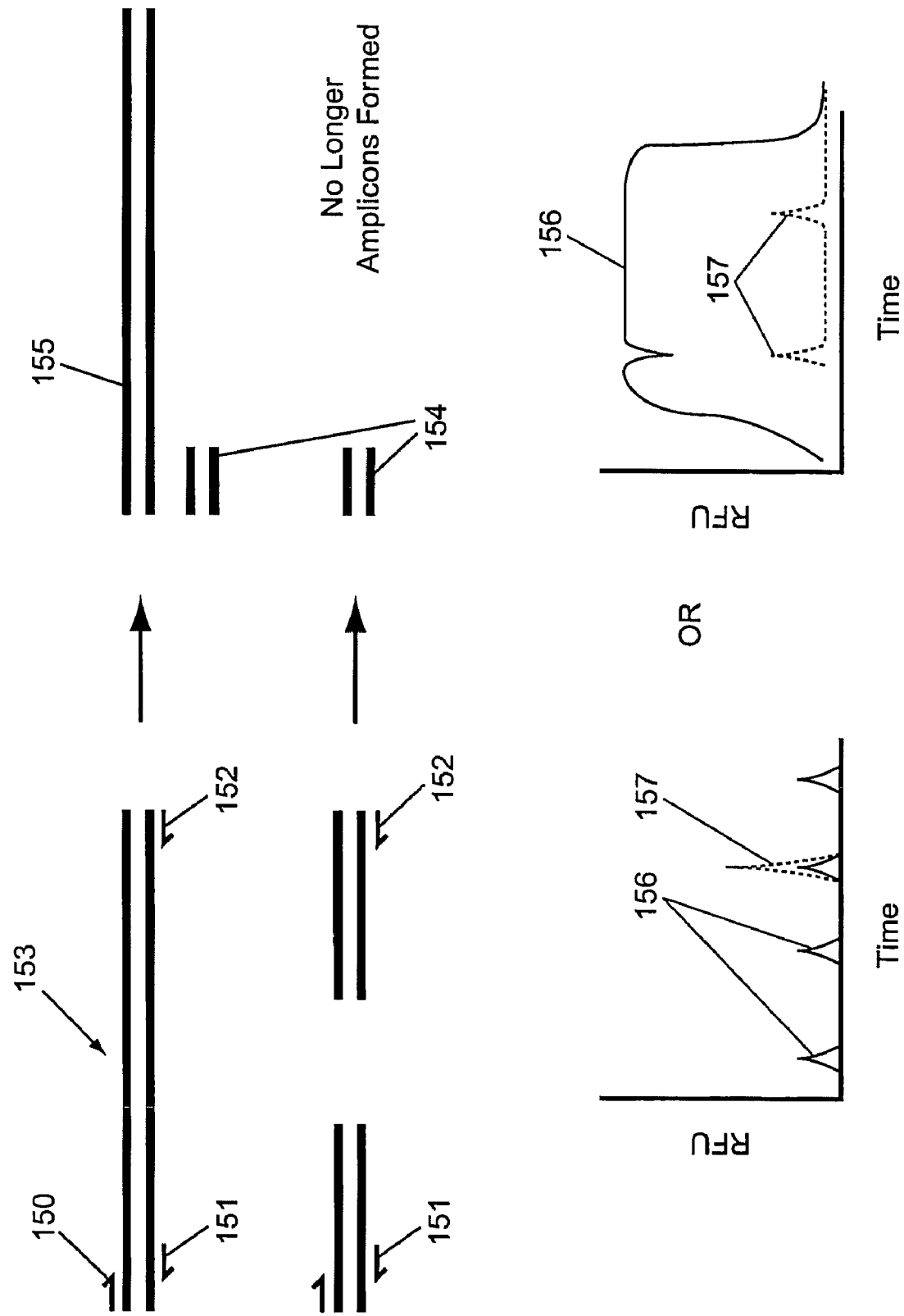
FIG. 15 shows a schematic diagram of low to single copy detection of nucleic acid of interest amplified using two amplicon sequences that overlap at a sequence complementary to at least one probe.

In another embodiment, as shown in FIG. 15, first strand primer 150 is shared between second strand primers 151 and 152 for an amplification that overlaps at the sequence of the shorter amplicon. If the nucleic acid of interest 153 is not fragmented between the shorter amplicon 154 sequence and the longer second strand primer 152 sequence, the amplification reaction will provide both shorter 154 and longer 155 amplicons. In such a case, hybridization to a probe specific to the shorter amplicon and a probe specific to the longer amplicon will yield short probe signals 156 coincident with long probe signals 157. If the nucleic acid of interest 153 is fragmented between the shorter amplicon 154 sequence and the longer second strand primer 152 sequence, the amplification reaction will provide only shorter 154 amplicon and detection of a single copy reaction mixture will yield only short probe signals 156. In some embodiments, the short amplicon can act as a control sequence confirming the effectiveness of the amplification and hybridization reactions. Optionally, the short amplicon can act as an internal reference to indicate the total number of total whole and fragmented nucleic acid of interest present in the sample of reaction mixture. In embodiments where nucleic acids in the sample are subject to random breakage (such as occurs in apoptotic cells) the region defined in the shorter amplicon can be far less likely to be fragmented than the region defined in the longer amplicon. In these embodiments, where the primer pairs share a common first strand primer, determination of a given length can be based on detection a probe hybridizing to a sequence outside of the shorter amplicon region, i.e., the determination does not require coincidence of signals in a single copy reaction. However, these embodiments can benefit, e.g., from the discrete counting provided by single copy detection methods to enhance the precision of counts and the confidence of statistical inferences from the data. Primer pairs in such amplifications typically define shorter amplicon sequences of about 100 base pairs, as above. Primer pairs defining the longer amplicon are typically separated by sequence lengths ranging from more than about 5000 base pairs to about 200 base pairs, or from about 500 base pairs to about 2000 base pairs, or about 3000 base pairs.

Amplification reactions can be carried out using any appropriate technique known in the art and as described in the Amplifying the Aliquots section above. For example, the amplification method can be PCR, RT-PCR, LCR, and/or any of the various RNA mediated amplification methods.

Although basic methods of determining whether a nucleic acid of interest has a given length include the use of one or two primer pairs or probes, additional information about the length and fragmentation status of a nucleic acid of interest can be obtained by using more than two primer pairs or probes. The additional probes and/or primer pairs can enhance the resolution of length determination between and/or outside of the first and second primer pairs and probes. For example, with an additional primer pair amplifying a sequence between the first and second primer pairs, detection of probed amplicons can yield additional information from low or single copy reactions. In such a case, coincident detection of only the first and additional probes can indicate the nucleic acid of interest has the given length between the probes but a break between the additional probe complement and the second probe complement. Coincident detection of only the additional and second signals can indicate the nucleic acid of interest has the given length between the additional and second probe complementary sequences but a break between the first probe complement and the additional probe complement. A non-fragmented nucleic of interest in this case would have coincident signals from each of the first, additional, and second probes in detection of a single copy reaction. In another example, with the additional primer pair amplifying a sequence outside sequences bracketed by the first and second primer pairs, detection of amplicons interrogated with the three appropriate probes can yield useful information from low or single copy reactions. In such a case, coincident detection of only the first and additional probes can indicate the nucleic acid of interest has the given length between the probes but a break exists between the first probe complement and the second probe complement. Coincident additional and second signals can indicate the nucleic acid of interest has the given length between the additional and second probe complements but a break exists between the first probe complement and the second probe complement. A non-fragmented nucleic of interest in this case would have coincident signals from each of the first, additional, and second probes in a single copy reaction. Such a nucleic acid of interest would have at least the given length between the additional probe and the nearest of the first or second probe, plus the given length between the first and second probe. Further additional probes and/or associated primer pairs can yield additional nucleic acid length information, as can be appreciated by those skilled in the art.

Complementary probes can specifically hybridize to nucleic acids of interest and/or associated amplicons to provide one or more signals from low or single copy hybridizations thereby yielding information useful in determining whether the nucleic acid has at least a given length. The probes can be hybridized under conditions of stringency (e.g., buffer ionic strength and temperature) suitable to provide the required level of specificity. In many embodiments, probes are hybridized to nucleic acids under highly stringent conditions. In preferred embodiments of determining length, the probes are molecular beacon (MB) probes, fluorescent resonance energy transfer (FRET) probes, or TaqMan probes, as described in the Amplification of Aliquots section above. In preferred embodiments detectable markers provide qualitatively different signals unique to each of the different probes. Optionally, two or more different probes can have the same signal and the coincident presence of the two probes in a single copy reaction mixture can be detected as a signal, e.g., of double amplitude or area.

Target nucleic acids of interest and/or associated amplicons hybridized to complementary probes can be subjected to marker signal detection procedures. Amplification and/or hybridization reaction mixtures can flow into a detection region for detection of any signals present in the mixtures. Depending on configuration of hardware, the detection region can be, e.g., microchambers or microchannels, a region where the amplification reaction mixture was formed or amplified, a region where the hybridization reaction took place, a cuvette region downstream from reaction regions, detection regions integral with or proximal to a microfluidic device, and/or the like. The detector can be any type appropriate to the marker signal and compatible with other system hardware, as described above. The probes, hybridized and/or released from the nucleic acid or amplicon, can be detected by flowing into or through the detection region, the detector can be scanned across the probes, or the probes can be detected in a two or three dimensional detection region, e.g., using imaging technologies known in the art.

Detected signals can be interpreted to provide detection of a nucleic acid of interest and a determination of whether the nucleic acid has at least a given length. As was discussed above from the perspective of primers and amplicons, coincident detection of one of more probes in a low or single copy reaction mixture can provide information about the length of a nucleic acid of interest. Theoretically, primers and amplicons are not necessary to determining whether a nucleic acid of interest has a given length or not, but amplification schemes can be useful to enhancing the sensitivity of such determinations. Detection of signals in a low or single copy reaction mixture from two or more probes that have been specifically hybridized to a nucleic acid (or associated amplicons) at sequences spaced a given distance along the nucleic acid can indicate the nucleic acid is not fragmented between the probes. Detection of a signal from only one probe can indicate the presence of a break in the nucleic acid. Accumulated data of detections from multiple low, single, and zero copy reaction mixtures can yield information useful in quantitation, proportioning, and correlating the nucleic acids present in samples.

Nucleic acids of interest of differing length can be quantified essentially as described throughout this specification, particularly in the Counting and Statistically Analyzing a Nucleic Acid of Interest section above. Signals detected from low, single, and/or zero copy reaction mixtures can be interpreted and counted to accumulate data useful in calculation of quantities. For example, inferences can be made about the total amount of full length or fragmented nucleic acid of interest in a sample based on counts of coincident signals, solitary signals, and no signal (zero copy) reactions. Appropriate adjustments can be made according to dilution factors, efficiency factors, internal reference values, and the like. Proportions of full length to fragmented nucleic acids of interest can be determined based on the proportions of associated signal counts. It is appreciated in the art that acquisition of larger amounts of signal data can improve the precision or accuracy of such quantitative determinations. For example, it is preferred in the methods to evaluate a sample by aliquotting the sample into at least 25 reaction mixtures with two or fewer copies (including single copy and zero copy reactions) in order to compile a statistically valid data set, e.g., to interpret the fragmentation status of the sample, calculate the proportions of fragments to unfragmented nucleic acids, to quantitate the nucleic acids of interest, to make valid correlations to disease states, and the like.

In another aspect, the shape, volume, width, height, length, area, or ratio, of the one or more signals can be evaluated to provide quantitative information about nucleic acids of interest. These peak parameters of acquired signals can be subjected to regression analyses to identify standard curve equations that most closely reflect the parameter change with changed concentrations of the nucleic acids of interest in samples. Where an assay includes detection of different signals from two or more probes with different detectable markers, the same or different peak parameters can be input for regression analysis of the different detected signals.

In one embodiment, the quantity of a nucleic acid of interest in a sample can be determined by measuring the change in a signal with increasing numbers of amplification cycles. Plotting the change in signal strength with increasing amplification cycles often results in a sigmoid curve. Certain precise points along the curve, such as points of inflection, points with certain slopes, points having a certain absolute signal strength, points having a certain fraction of maximum (plateau) signal strength, and/or the like, can be identified with high precision. Useful standard curves can be prepared based on regression analyses of any of these identifiable points from assay of standard materials of known nucleic acid concentration. For example, a standard curve can be prepared representing known nucleic acid of interest concentrations versus amplification cycles required to attain the chosen identifiable point. Such standard curves can be, e.g., plotted curves of standard data or mathematical representations of such curves. Concentrations of nucleic acids for unknown samples can be determined with reference to the standard curve. Different degrees of amplification can be consistently obtained, e.g., by flowing amplification reactions through an active amplification region at different rates, for different times, and/or different distances to provide a series of reaction mixtures experiencing different numbers of amplification cycles.

Figure 16B:
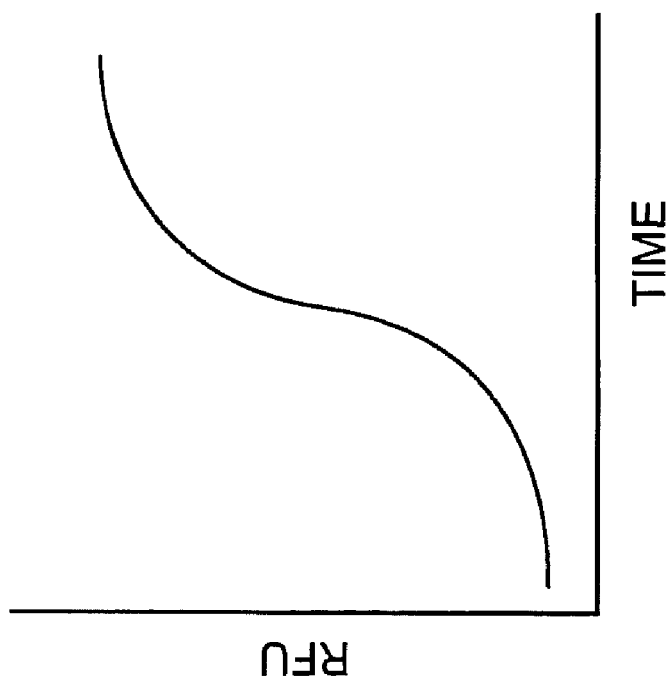
FIGS. 16A to 16B show schematic diagrams of amplification curves generated by flowing amplification reactions different distances within an actively cycling amplification region.
Figure 16A:
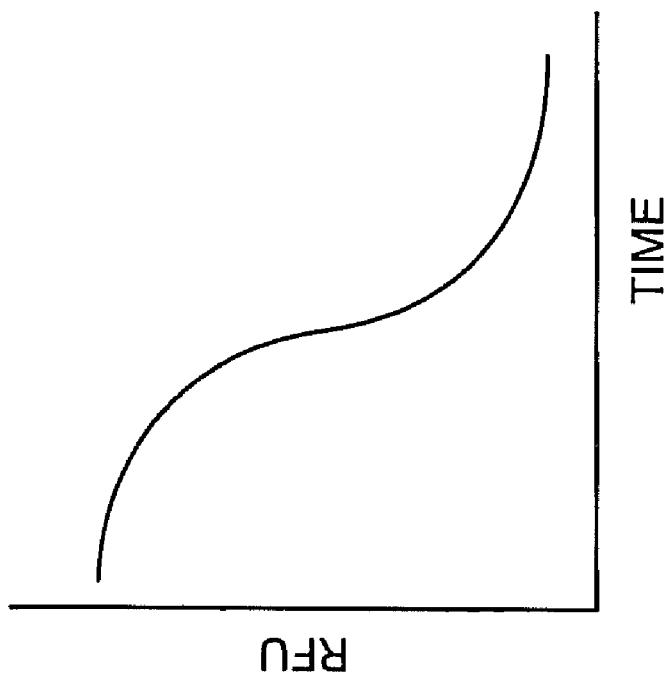

In one embodiment, different degrees of, e.g., PCR amplification are provided by flowing the amplification reaction mixture different distances in an actively cycling heated region of a thermocycler channel. For example, amplification reactions can flow into an actively cycling amplification region for a certain distance before thermocycling is stopped. In this case, the front edge of the flowing slug of reaction mixtures experiences more amplification cycles while late entering mixtures nearer the trailing edge experience fewer amplification cycles. If such a slug of reaction mixtures were to continue flowing past a detector, the detector signal output can be a reverse sigmoid curve as shown in FIG. 16A. Alternately, a slug of amplification reaction mixtures can flow into an inactive amplification region before starting thermocycling so that reaction mixtures near the front edge flow out of the thermocycler sooner to experience fewer amplification cycles than reaction mixtures nearer the trailing edge. Detection of this slug of reaction mixtures flowing past a detector can provide a sigmoid curve detector signal output, as shown in FIG. 16B, indicating weak amplification at the front edge of the slug and higher amplification for the trailing edge.

Information about the fragmentation state or integrity of nucleic acids of interest can be correlated to disease states, e.g., of the sample source organism. Correlation analyses known in the art can be carried out, e.g., comparing qualitative, quantitative, and/or proportion data on the length of certain nucleic acids obtained using methods of the invention. For example, disease states can be correlated to a quantity of unfragmented nucleic acid, or a proportion of fragmented nucleic to nucleic acid having a given length. A proportional threshold or quantitative threshold can be established using statistical analyses to provide an acceptable degree of confidence in identification of samples possibly positive for the correlated disease state without unacceptable false positive results. For example, a certain proportion of fragmented to unfragmented nucleic acid in a stool or cervical swab sample can identify the sample as likely to originate from a patient having, e.g., colon or cervical cancer, respectively.

Methods for Quantifying Nucleic Acids of Interest

Methods and systems of the invention can be used in various formats to quantify nucleic acids of interest. The quantitative assays can be configured to provide a desired quality of output results. For example, assay parameters, such as, e.g., sensitivity, accuracy, precision, and rates of false positives or false negatives can be influenced by the design of particular assays. Repetition of assays can increase precision. The quantitative assays can be improved by evaluating signal peak parameters best suited to provide valid results, e.g., with the desired range, sensitivity and/or accuracy.

Figure 17B:
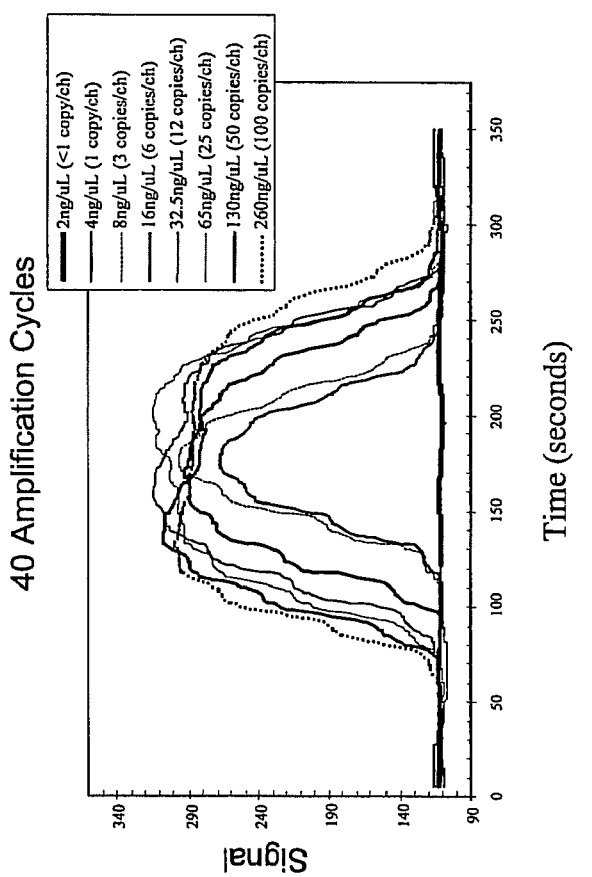
FIG. 17 shows detected signal peaks for a series of nucleic acid standard materials with amplification cycles numbering 25 cycles or 40 cycles.
Figure 17A:
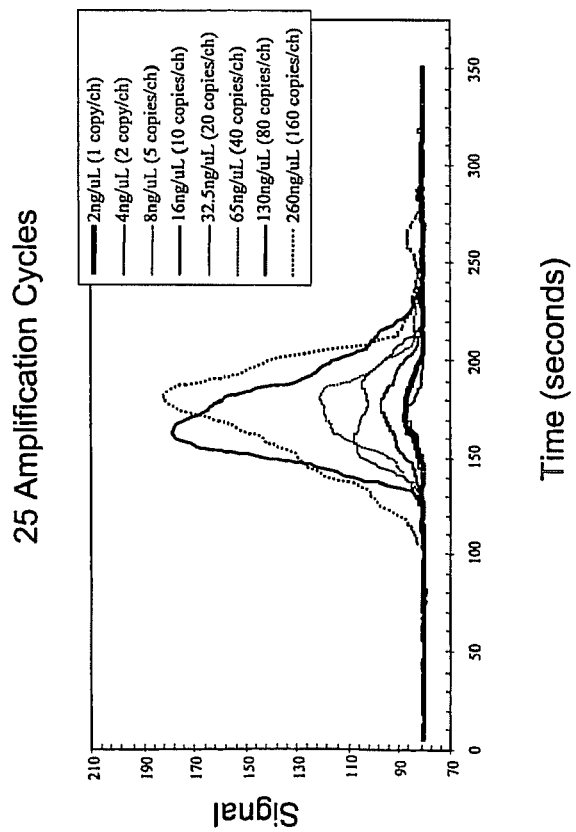

Comparison of a sample signal output peak to a series of standard signal output peaks can indicate the concentration of a nucleic acid of interest in a sample. For example, a series of standard materials containing known mounts of the nucleic acid of interest can each be amplified through the same number of amplification cycles to produce a series of detectable signals, as shown in FIG. 17. For each concentration of nucleic acid standard, a different detectable signal peak associated with the amplicons can be detected. In one embodiment, a sample with an unknown concentration of the nucleic acid of interest is amplified the same number of cycles as the standard materials. The resultant amplicons are detected, with the same probe and detectable marker system as for the standards, to provide a signal with certain distinctive peak parameters. The signal from the sample can be evaluated to identify signal peak parameters (e.g., the shape of signal peaks, points of inflection on signal peaks, slopes of signal peaks, signal peak amplitudes, signal peak areas, signal peak widths at half height, etc.) most suitable for the analytical goal. For example, peak area might provide the most accurate quantitative comparison, while peak height might provide a more precise comparison, and peak shape might provide suitable quantitative comparisons over a broader range of concentrations. Identifying an appropriate signal peak parameter for comparison in a particular instance can be determined, e.g., using methods of assay development and validation procedures well known in the art. The precision and/or accuracy of nucleic acid quantification can be enhanced by interpolating the comparison to intermediate values between standard values, by running replicate standards, by statistical analyses of repeated sample assays, by running comparisons at two or more amplification levels, and/or the like.

Figure 18A:
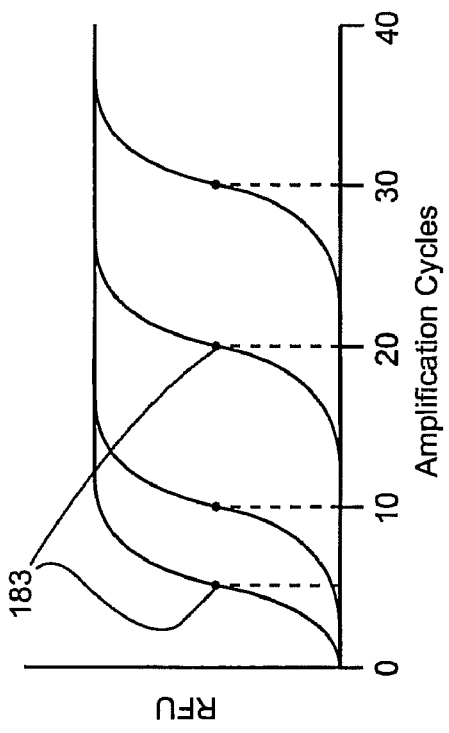
FIGS. 18A to 18C show schematic charts demonstrating the quantitation of a nucleic acid of interest based on the number of amplification cycles required to reach an identifiable point of maximum slope.
Figure 18B:
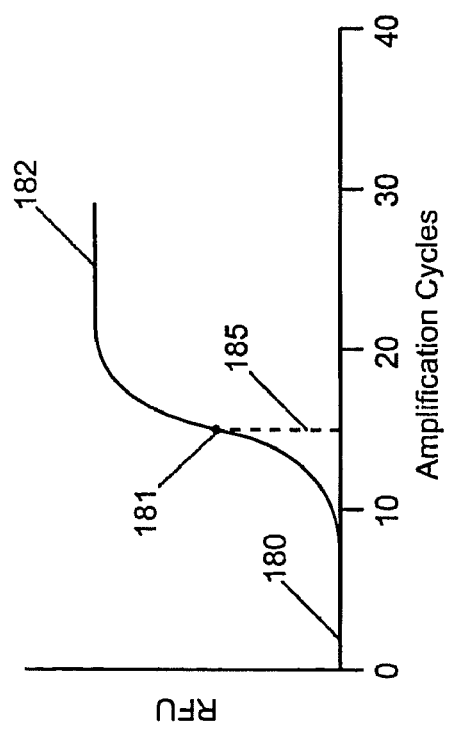
Figure 18C:
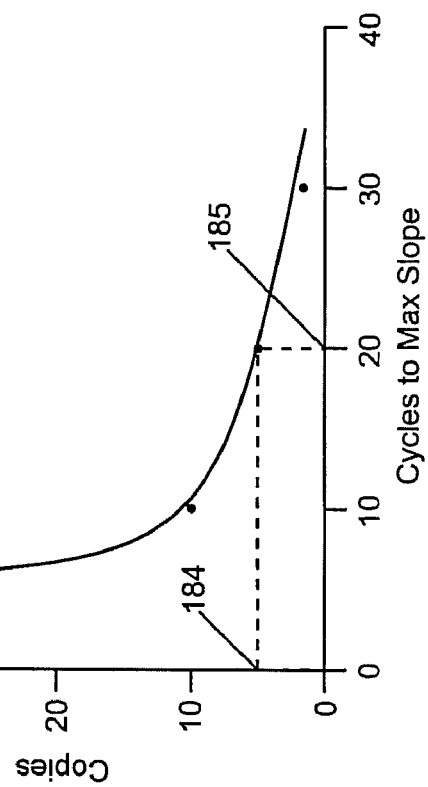

One method of enhancing reliability of nucleic acid quantification by using multiple assay results depends on comparison of amplification signal response curves between samples and standards. For example, the amount of amplicon associated signal generated over a number of amplification cycles can be compared to the signals for standards of various known concentrations. As shown schematically in FIG. 18A, a signal from an amplified sample can start low 180, increase logarithmically at some point 181, and taper off to a maximum signal plateau 182 with increasing numbers of amplification cycles, thus describing a sigmoid curve. Standard materials with different known concentrations of the nucleic acid of interest can be amplified, as shown in FIG. 18B, to provide a series of standard sigmoid curves. Points along the sample and standard curves can be identified, e.g., with various levels consistency. Identifiable points can be, e.g., points of inflection, points having a certain slope, points having a certain signal amplitude, points having a certain fraction of a maximum (e.g., plateau asymptotic) signal amplitude, and the like. A standard curve of concentration versus cycles to an identifiable point can be prepared, as shown in FIG. 18C, so that the concentration of the nucleic acid in a sample can be determined from the number of amplification cycles it takes for the sample to reach the identifiable point. For example, a point of maximum slope 183 (maximum rate of signal increase) can be precisely identified on each of the standard curves. The cycles to maximum slope can be plotted versus concentration to prepare a standard curve. The nucleic acid of interest concentration of an unknown sample can be read as the concentration 184 providing the number of cycles 185 to the maximum slope from the standard curve. Of course, such determinations do not necessarily require manual plotting of standard curves or sample curves. As used herein, preparing curves includes all means of expressing the relationships between relevant factors (e.g., concentration and slope, signal parameter and amplification cycles, identifiable points and concentration, etc.), such as, e.g., data plotting, regression analysis, curve fitting, determination of an equation, and/or the like whether accomplished manually or with the aid of an analog or digital computer and software. In this embodiment of nucleic acid of interest quantitation, if is preferred standard and sample reaction mixtures be cycled through different numbers of amplification cycles, e.g., as described in the Methods of Determining the Fragmentation Status of Nucleic Acids section above.

The quantities and proportions of nucleic acids of a given length and/or fragmented nucleic acids of interest can be determined with high precision, e.g., by reference to standard curves of concentration versus amplification cycles to identifiable points generated for two or more probe signals. In this concept, detectable signals associated with fragmented or unfragmented nucleic acid of interest can be quantitated separately, e.g., according to the methods described in the paragraph above, to evaluate the integrity of the nucleic acid of interest in a sample. In one aspect, standard curves of concentration versus amplification cycles to an identifiable point can be separately plotted for signals associated with two or more amplicons of the nucleic acid of interest. (A signal is associated with an amplicon, e.g., if it originates from a nucleic acid probe that has hybridized to a sequence of the amplicon and has detectable marker providing the signal.) Cycles to the identifiable point for the sample can be compared to the standard curves for each amplicon to separately determine fragmented and given length nucleic acid of interest concentrations. In a preferred embodiment, the signals are detected from homogenous reaction mixtures. In another preferred embodiment, the signals are detected from low or single copy reaction mixtures to provide highly resolved data on the integrity of the nucleic acid of interest.

Systems for Determining the Fragmentation Status of Nucleic Acids

Systems of the invention can provide efficient processing and well adapted hardware for high sensitivity differentiation of the lengths of nucleic acids of interest in samples. Systems for differentiating lengths of nucleic acids can be essentially as described herein for single molecule amplifications, but, e.g., incorporating additional elements for amplification, detection, interpretation, and/or correlation of multiple probes. The core system for differentiating nucleic acid length includes, e.g., a microfluidic device capable of containing low and single copy reaction mixtures in microchannels or microchambers, detectors capable of distinguishing one or more signals from a homogenous reaction mixture, and a software system configured to interpret single or coincidentally detected signals to lengths of individual nucleic acids from a sample. Additional subsystems can include sample storage modules, retrieval modules, dilution modules, and computers, as discussed above for single molecule amplification systems in general.

Figure 19:
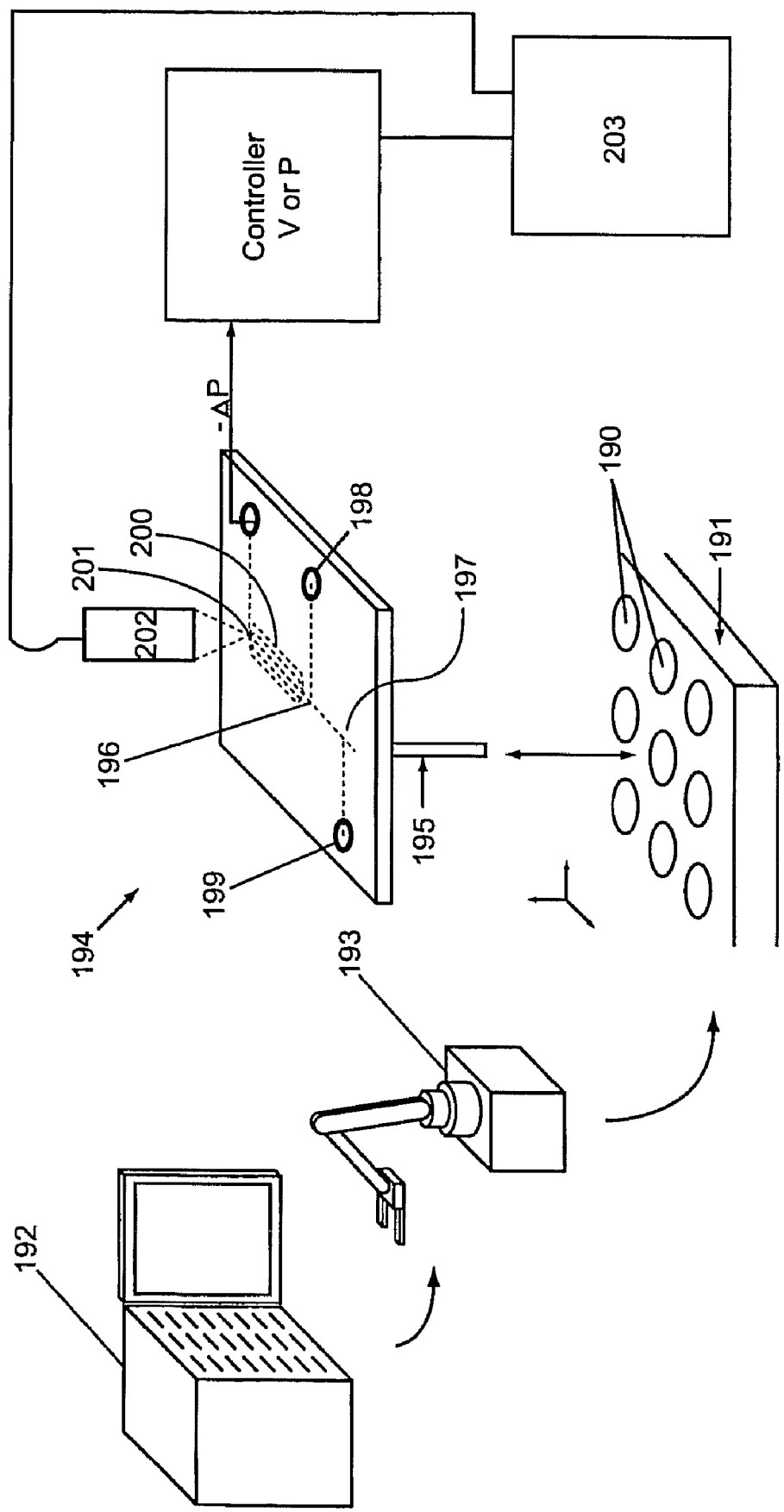
FIG. 19 shows a schematic diagram of a system of the invention for differentiating the length of nucleic acids of interest.

An exemplary system for differentiating lengths of nucleic acids, as shown in FIG. 19, can function as follows. Samples 190 in wells of microtiter plates 191 can be held in storage module 192 until retrieval by retrieval module 193 and delivery for sampling by microfluidic device 194. Samples are aspirated up a capillary sipper tube 195 to microchannels 196 or microchambers of the microfluidic device where integral dilution module 197 (e.g., a dilution channel) appropriately dilutes the sample with reagents 198 and buffers 199 to constitute an amplification reaction mixture. The reaction mixtures can be separately aliquoted into each channel in multiple amplification region 200 where low, single, and/or zero copy reaction mixtures can be exposed to amplification conditions (e.g., thermocycling). Amplified reaction mixture aliquots can flow into detection region 201 where signals from detectable markers on one or more different probes can be detected by detector 202. The detector can communicate with computer 203 to transmit detector signals for interpretation and/or correlation by system software.

Samples for nucleic acid differentiation in the systems can be any that contain natural or unnatural nucleic acids. For example, the samples can include a nucleic acid with single nucleotide polymorphism (SNP), a cancer associated nucleic acid, a nucleic acid from an infective agent, whole blood, serum, plasma, stool, urine, a vaginal secretion, ejaculatory fluid, synovial fluid, a biopsy, cerebrospinal fluid, amniotic fluid, or a forensic nucleic acid. Samples can be stored in a storage module, as described above, under environmental conditions of temperature, light, and humidity conducive to long storage life of the samples. Libraries of samples can be stored, e.g., as matrices of various liquid aliquots in multiwell plates or dry spots on slides. The samples can be located at positions in the storage module trackable with an inventory system and accessible by a sample retrieval system.

Retrieval modules can be employed in the systems of differentiating nucleic acid length, e.g., to enhance the high throughput capabilities of the system. The retrieval modules can remove designated samples from a storage module and deliver them to dilution modules or microfluidic devices for analysis. The retrieval modules can have, e.g., robotic arms with 6 degrees of freedom of movement, x-y plotted tray graspers, belt driven conveyors, and/or the like. Bar code readers or radio frequency identification systems can be incorporated into the retrieval modules to identify and track tagged samples.

Reaction mixtures for determination of nucleic acid length can be prepared to include a nucleic acid of interest, two or more polymerase primer pairs, nucleotide triphosphates, buffers, and/or two or more detectable probes. The reaction mixture constituents can be combined in any order at any suitable time or place. The reaction mixtures can be constituted outside the microfluidic device, e.g., in microwell plates using manual or automated pipettor systems. The reaction mixture can be diluted outside of the microfluidic device, e.g., by manual serial dilutions or by using an automated dilution module. The dilutions can provide a concentration of the nucleic acid of interest resulting in desired amounts of low, single, and zero copy reaction mixtures in amplification microchannels, hybridization reactions, and/or detection regions of the system. The reaction mixture can include, e.g., two or more primer pairs defining amplicons and bracketing sequences complementary to probes a given distance apart on the nucleic acid of interest. Preferred primer pairs define amplicons ranging in size from about 50 base pairs to about 3000 base pairs, or about 100 base pairs. In preferred embodiments, the primer pairs have roughly the same melting temperatures and define amplicons of about the same length. In one embodiment, the amplicons include a shorter amplicon that overlaps a longer amplicon in a region having sequences complementary to one or more probes.

In one aspect, the systems can include, e.g., solid supports to provide affinity concentrations of sample constituents for analysis, or concentration of hybridization reaction mixture constituents. Solid supports can have affinity elements, such as oligonucleotides complementary to reaction constituents (e.g., nucleic acids of interest, primers, probes, etc.), capable of specifically capturing the constituents. The solid supports can be useful in adjusting the concentration of nucleic acids of interest for input into the systems. The solid supports can immobilize constituents during amplification or hybridization steps. Probes that have been hybridized to the nucleic acids of interest and/or their associated amplicons can be captured in a detection region for detection. Although certain reaction mixture constituents can be immobilized on the solid supports while certain other constituents can flow past to be removed, the mixture can still be considered homogenous if different probes are present in the same mixture at the time of detection.

One or more probes can be present in the amplification reaction mixture and/or in the hybridization mixture to hybridize with the nucleic acid of interest or associated amplicons. In some embodiments, e.g., wherein detection of the longer amplicons indicate unfragmented nucleic acid, signals from a single probe can confirm the presence of unfragmented nucleic acid. However, in preferred embodiments, the system includes two or more probes with specificity for nucleic acid sequences separated a given distance along the nucleic acid of interest. In many cases the signal can be enhanced by providing alternate probes specific for sequences in the second strand of a double stranded nucleic acid at about each end of the given length; typically, the alternate probes hybridize near the first strand probes but are not complementary to the first strand probes in order to avoid hybridization of primers to each other. Preferred probes have significant signal changes associated with binding to target nucleic acid of interest. This can provide, e.g., a positive signal against a low background from a homogenous mixture (i.e., without the need to separate unhybridized probe from the reaction mixture). Although probes can have any of the variety of detectable markers described above, preferred probes for differentiating the length of a nucleic acid are molecular beacon (MB), TaqMan, and fluorescent resonance energy transfer (FRET) probes.

In an aspect of the invention, multiple assays can be run in a single reaction mixture (multiplexing). For example, a reaction mixture can include independently detectable probe pairs for more than one nucleic acid of interest. A reaction mixture can be constituted to include, e.g., a pair of probes complementary to sequences at the ends of a first given length of a first nucleic acid of interest, and another pair of probes complementary to sequences at the ends of a second given length of another nucleic acid of interest. The four probes can each have different detectable markers so they can be individually detected in reaction mixtures. Should a reaction mixture in the detector region coincidentally emit three probe signals, system software could unambiguously interpret this to indicate the presence of a single copy of an identifiable first nucleic acid of interest having the given length and a single fragmented copy of the other nucleic acid. One skilled in the art can envision other unambiguous signal combinations using such a multiplexing scheme.

Microfluidic devices in systems for differentiating nucleic acid lengths can include chips with reagent wells, gas, liquid and electrical contact ports, sample sippers, microchannels and microchambers, amplification microchannels, and detection regions, as described above in the Example Systems section. In preferred embodiments, the microfluidic device includes such features as a sipper, multiple amplification channels (such as shown in FIG. 1), and detection region configured for laser excitation and fluorescent detection at multiple frequencies.

Detectors in the systems can be any configured with a capability to detect two or more signals from a homogenous mixture of reaction mixture constituents. The detector can be appropriate for the type of detectable marker signal provided by the hybridized probes. The detector can include, e.g., a fluorometer, a charge coupled device, a laser, an enzyme, or an enzyme substrate, a photo multiplier tube, a spectrophotometer, scanning detector, microscope, a galvo-scanner, etc. The detectors can monitor a detection region into which amplification reaction mixtures, aliquots, hybridization reaction mixtures, or reaction mixture constituents have flowed. As hybridization actuated fluorescent probes are preferred in the methods, preferred detectors in the systems are fluorometers. Although the presence of two probes with the same detectable marker signals can be distinguished, it is preferred that the signals be different and the detector be capable of distinguishing two or more different signals coincidentally from a homogenous mixture. In a more preferred embodiment, the detector comprises a laser light excitation source directed to the detection region through optic fibers, and a photodiode array capable of simultaneously detecting two or more emission wavelengths.

A software system can be an element of the system to interpret one or more signals and/or to correlate the signals to a disease state. The software system can include, e.g., algorithms to count signals, calculate concentrations, calculate proportions, prepare standard curves, and/or evaluate correlations, e.g., to disease states. The software can interpret, e.g., coincidence of two or more signals to indicate the presence of a nucleic acid of a given length in the detection region. The software can interpret, e.g., a single signal to indicate the presence of a fragmented nucleic acid in the detection region. The software can calculate a quantity of a nucleic acid of interest by factoring in information, such as, e.g., the number of signal counts, reaction volumes, dilution or concentration factors, efficiency factors, known input values and constants, signal peak shape, and/or the like. The software can interpret peak parameters, such as a volume, width, height, length, area, and/or a ratio, of the signals detected by the detector to indicate a number of copies of the nucleic acid of interest in the sample, a number of the nucleic acids of interest having a given length, or a proportion of nucleic acids of interest having different lengths. Software systems can correlate results of one or more signal detection to disease states, e.g., by comparing a validated quantity or proportion threshold to assay results for a sample.

Computers can be an important element of systems for differentiating lengths of nucleic acids. Computers can coordinate control activities in the system, such as, e.g., sample identification, sample retrieval, sample sipping, control of microchip pressures and voltages, receipt of detector signals, and software interpretation of signals. In preferred embodiments, the computer is in communication with the signal detector to receive, store, and evaluate signals from sample or standard assays. Computers in the systems can be as described in the Computers section above. For example, systems in the present invention can include, e.g., a digital computer with data sets and instruction sets entered into a software system to practice the methods of determining lengths described herein. The computer can be, e.g., a PC (Intel x86 or Pentium chip-compatible with DOS®, OS2®, WINDOWS® operating systems) a MACINTOSH®, Power PC, or SUN® work station (compatible with a LINUX or UNIX operating system) or other commercially available computer which is known to one of skill. The computer can be, e.g., a simple logic device, such as an integrated circuit or processor with memory, integrated into the system. Software for interpretation of detector signals is available, or can easily be constructed by one of skill using a standard programming language such as Visualbasic, Fortran, Basic, Java, or the like.

While the foregoing invention has been described in some detail for purposes of clarity and understanding, it will be clear to one skilled in the art, from a reading of this disclosure, that various changes in form and detail can be made without departing from the true scope of the invention. For example, many of the techniques and apparatus described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of determining fragmentation status of a nucleic acid of interest in a sample at the start of the method, the method comprising:
    contacting the nucleic acid of interest in a reaction mixture with two or more different probes complementary to sites separated by a point of potential fragmentation, wherein the probes each comprise a detectable marker;
    flowing the nucleic acid of interest into a detection region;
    detecting detectable marker signals from the probes; and
    determining fragmentation status of the nucleic acid of interest, wherein coincident detection of signals from two or more of the different probes indicates the nucleic acid of interest was not fragmented between the probes at the start of the method and has at least a given length, and wherein detecting a signal from only one of the different probes indicates the nucleic acid of interest was fragmented.

2. The method of claim 1, wherein the reaction mixture comprises a single copy of the nucleic acid of interest.

3. The method of claim 1, wherein the two or more probes each comprise detectable markers with different signals.

4. The method of claim 1, wherein at least one of the probes comprise a fluorescent resonant energy transfer (FRET) detectable marker or a molecular beacon (MB) marker.

5. The method of claim 1, further comprising correlating one or more lengths of one or more nucleic acids of interest to a disease state by identifying a ratio or quantitative threshold of lengths associated with the disease state.

6. The method of claim 1, further comprising:
    contacting the nucleic acid of interest with a first primer pair;
    contacting the nucleic acid of interest with a second primer pair comprising at least one primer-complementary to a sequence of the nucleic acid of interest or its-complement outside of a sequence defined by the first primer pair; and
    amplifying the nucleic acid of interest in the reaction mixture contained in a microchannel or microchamber with primer extensions initiated at primers to produce first amplicons defined by the first primer pair or second amplicons defined by the second primer pair; wherein at least a first probe is complementary to a sequence of the first amplicons and at least a second probe is complementary to a sequence of the second amplicons; whereby a sensitivity of said detecting is increased.

7. The method of claim 6, wherein one primer pair comprises control primers defining amplicons of 100 base pairs or less in length and another primer pair comprises test primers defining longer amplicons ranging in length from about 100 base pairs to about 3000 base pairs.

8. The method of claim 6, wherein a region of the nucleic acid of interest defined by the first primer pair does not overlap with a region of the nucleic acid of interest defined by the second primer pair.

9. The method of claim 6, wherein at least one of the probes is-complementary to an amplicon sequence defined by one primer pair but not complementary to an amplicon sequence defined by another primer pair.

10. The method of claim 6, further comprising:
    contacting the nucleic acid of interest with one or more additional primer pairs comprising at least one primer complementary to a sequence of the nucleic acid of interest or its complement outside a sequence defined by the first primer pair or second primer pair;
    whereby one or more additional amplicons are produced, and whereby coincident detection of signals from a probe specific for the one or more additional amplicons and the first or second probes indicates the nucleic acid of interest is not fragmented between sequences complementary to probes providing the signals.

11. The method of claim 6, wherein said amplifying comprises: a polymerase chain reaction (PCR), reverse-transcriptase PCR (RT-PCR), ligase chain reaction (LCR), a Q-β replicase or RNA/transcription mediated techniques.

12. The method of claim 1, further comprising:
aliquotting the sample into at least 25 reaction mixtures comprising 2 or fewer copies of the nucleic acid of interest each;
individually subjecting the sample aliquots to the contacting and the detecting; and
individually counting a number of aliquots resulting in detection of a signal from one probe or individually counting a number of aliquots resulting in detection of signals from two or more probes.

13. The method of claim 12, wherein the at least 25 reaction mixtures comprise one or more reaction mixtures comprising single copies of the nucleic acid of interest.

14. The method of claim 12, wherein the at least 25 reaction mixtures comprise one or more reaction mixtures comprising zero copies of the nucleic acid of interest.

15. The method of claim 12, further comprising evaluating the number of one probe signals and two probe signals to determine a proportion of nucleic acids of interest having different lengths.

16. The method of claim 15, further comprising correlating a disease state with the proportion.

17. The method of claim 1, further comprising quantifying the nucleic acid of interest.

18. The method of claim 17, wherein said quantifying comprises counting a number of signals from one or more of the different probes.

19. The method of claim 17, wherein said quantifying comprises detecting a volume, width, height, length, area, shape, or ratio, of the one or more signals.

20. The method of claim 17, wherein said quantifying comprises comparison of a probe detectable marker signal to an internal standard signal.

21. The method of claim 17, wherein said quantifying comprises comparison of signals from two or more reaction mixtures comprising different degrees of amplification.

22. The method of claim 21, wherein the two or more reaction mixtures comprise different amplification due to: flowing through a thermocycler at different flow rates, flowing different distances into a thermocycler, remaining in a thermocycler for different amounts of time, or experiencing different numbers of amplification cycles.

23. The method of claim 1, further comprising diluting the sample to obtain one or more reaction mixtures containing a single copy of the nucleic acid of interest.

24. The method of claim 23, wherein the nucleic acid of interest is diluted to a concentration of about 1 molecule per nanoliter or less.

25. The method of claim 1, wherein the sample comprises a sample selected from the group consisting of: whole blood, serum, plasma, stool, urine, vaginal secretions, ejaculatory fluid, a cervical swab, synovial fluid, a biopsy, cerebrospinal fluid, amniotic fluid, sputum, saliva, lymph, tears, sweat, and urine.

* * * * *